(12) United States Patent
Fukuzawa et al.

(10) Patent No.: US 12,291,546 B2
(45) Date of Patent: May 6, 2025

(54) PHOSPHONIUM COMPOUND, REAGENT KIT FOR DERIVATIZATION, MASS SPECTROMETRIC METHOD, AND METHOD FOR PRODUCING PHOSPHONIUM COMPOUND

(71) Applicant: JEOL Ltd., Tokyo (JP)

(72) Inventors: Seketsu Fukuzawa, Tokyo (JP); Koji Takahashi, Tokyo (JP); Yoshiyuki Itoh, Tokyo (JP); Masaki Takiwaki, Tokyo (JP); Shugo Tsuda, Ibaraki (JP); Masayoshi Mochizuki, Ibaraki (JP); Taku Yoshiya, Ibaraki (JP)

(73) Assignee: JEOL Ltd., Tokyo (JP)

( * ) Notice: Subject to any disclaimer, the term of this patent is extended or adjusted under 35 U.S.C. 154(b) by 161 days.

(21) Appl. No.: 17/961,020

(22) Filed: Oct. 6, 2022

(65) Prior Publication Data

US 2023/0112623 A1 Apr. 13, 2023

(30) Foreign Application Priority Data

Oct. 7, 2021 (JP) .................................. 2021-165739

(51) Int. Cl.
*C07F 9/54* (2006.01)
(52) U.S. Cl.
CPC ............ *C07F 9/54* (2013.01); *C07B 2200/13* (2013.01)
(58) Field of Classification Search
CPC ............................... C07F 9/54; C07B 2200/13
USPC ......................................................... 514/77
See application file for complete search history.

(56) References Cited

PUBLICATIONS

Office Action issued in JP2021165739 on Jan. 9, 2024.
Rideout et al., Cationic drug analysis using matrix-assisted laser desorption/ionization mass spectrometry: Application to influx kinetics, multidrug resistance, and intracellular chemical change, Proceedings of the National Academy of Sciences of the United States of America, vol. 90, Nov. 1993, pp. 10226-10229.
Pavlov et al., Aminolysis and Hydrazinolysis of Esters Triphenylphosphonioacetic Acid, Zhurnal Obshchei Khimii, vol. 57, No. 9, 1987, pp. 1955-1959.
Revised Extended European Search Report issued in EP22199998.0 on May 23, 2023.
Iwasaki et al., A new strategy for ionization enhancement by derivatization for mass spectrometry, Journal of Chromatography B, 2011, No. 879, pp. 1159-1165.
Gravitte et al., Liquid chromatography-mass spectrometry applications for quantification of endogenous sex hormones, Biomedical Chromatography, 2021, 35:e5036, pp. 1-37.
Office Action issued in EP22199998.0 on Oct. 4, 2023.
Ovakimyan et al., Reactions of Phophonioalkyl Derivaties of Phenlhydrazine and Hydroxylamine, Russian Journal of General Cehmistry, vol. 75, No. 7, 2005, pp. 1069-1073, Translated from Zuhurnal Obshchei Kimii, vol. 75, No. 7, 2005, pp. 1132-1136.
Nevstad and Songstad, Solvent Properties of Dichloromethane. II. The Reactivity of Dichloromethane Toward Amines, Acta Chemica Scandinavica, B 38, No. 6, 1984, pp. 469-477.
Cheng et al., Equilibrium Acidities and Homolytic Bond Dissociation Enthalpies of the Acidic C—H Bonds in As-Subdtituted Triphenylarsonium an Related Cations, Journal of Organiz Chemistry, vol. 63, 1998, pp. 7072-7077.
Extended European Search Report issued in EP22199998.0 on Feb. 14, 2023.
Barry et al., Use of S-pentafluorophenyl tris(2,4,6-trimethoxyphenyl) phosphonium acetate bromide and (4-hydrazino-4-oxobutyl) [tris(2,4,6-trimethoxyphenyl) phosphonium bromide for the derivatization of alcohols, aldehydes and ketones for detection by liquid chromatography/electrospray mass spectrometry, Rapif Communications in Mass Spectrometry, 2003, vol. 17, pp. 484-497.
Huang et al., A Picomole-Scale Method for Charge Derivatization of Peptides for Sequence Analysis by Mass Spectrometry, Analytical Chemistry, American Chemical Society, 1997, vol. 69, pp. 137-144.
Spikmans et al., On-line on-chip post-column derivatisation reactions for pre-ionisation of analytes and cluster analysis in gradient u-liquid chromatography/electrospray mass spectrometry, Rapid Communications in Mass Spectrometry, 2002, vol. 16, pp. 1377-1388.
Kim et al., Intra-mitochondrial reaction for cancer cell imagine and anti-cancer therapy by aggregation-induced emission, Royal Society of Chemistry, 2020, vol. 10, pp. 43383-43388.

(Continued)

*Primary Examiner* — Kristin A Vajda
(74) *Attorney, Agent, or Firm* — The Webb Law Firm

(57) ABSTRACT

Provided is a phosphonium compound represented by Formula (I):

[Chemical Formula I]

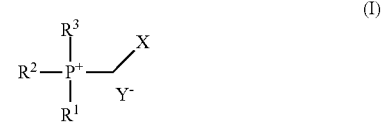

in Formula (I), $R^1$, $R^2$, and $R^3$ are independently from each other, an alkyl group or an aryl group, the alkyl group is a substituted or unsubstituted, linear or branched alkyl group having 1 to 20 carbon atoms or a substituted or unsubstituted cyclic alkyl group having 5 to 20 carbon atoms, the aryl group is a substituted or unsubstituted aryl group having 6 to 20 carbon atoms; X is a reactive group having a hydrazide group, a halide group, a pseudohalide group, or a thioester group; and $Y^-$ is an anion having a total charge of −1, or $Y^-$ is absence.

5 Claims, 68 Drawing Sheets

(56) References Cited

PUBLICATIONS

Baker et al., Irreversible Enzyme Inhibitors, CLXXVII, Active-Site-Directed Irreversible Inhibitors of Dihydrofolate, Reductase Derived From 4,6-Diamino-1,2-dihydro-2,2-dimethyl-1-(phenylalkylphenyl)-s-triazines, Journal of Medicinal Chemistry, 1970, vol. 13, No. 6, pp. 1154-1160.

Aitken et al., Flash vacuum pyrolysis of stabilised phosphorus ylides. Pary 16. Model studies for the construction of conjugated polymers., Tetrahedron, Elsevier Science Publishers, vol. 55, 1999, pp. 11039-11050.

Pavlov et al., Aminolysis and Hydrazinolysis of Triphenylphosphonioacetic Acid Esters, Journal of General Chemistry of the USSR, vol. 57, 1987, pp. 1750-1754.

Aitken et al., New reactions and reactive intermediates in the pyrolysis of cyclic phosphonium ylides, The Free Internet Journal for Organic Chemistry, 2017, pp. 293-301.

Communication issued in EP22199998.0 on Oct. 11, 2024.

Barry et al., Use of S-pentafluorophenyl tris (2,4,6-trimethoxyphenyl) phosphonium acetate bromide and (4-hydrazino-4-oxobutyl) [tris (2,4,6-trimethoxyphenyl) phosphonium bromide for the derivatization of alcohols, aldehydes and ketones for detection by liquid chromatography/electrospray mass spectrometry; Rapid Communications in Mass Spectrometry, 2003, vol. 17, pp. 484-497.

Shin et al., Fmoc-Based Synthesis of Peptide-Thioesters: Application to the Total Chemical Synthesis of Glycoprotein by Native Chemical Ligation; Journal of American Chemical Society, 1999, vol. 121, pp. 11684-11689.

[Fig. 1-1]
A: Proton (Chemical compound 1)
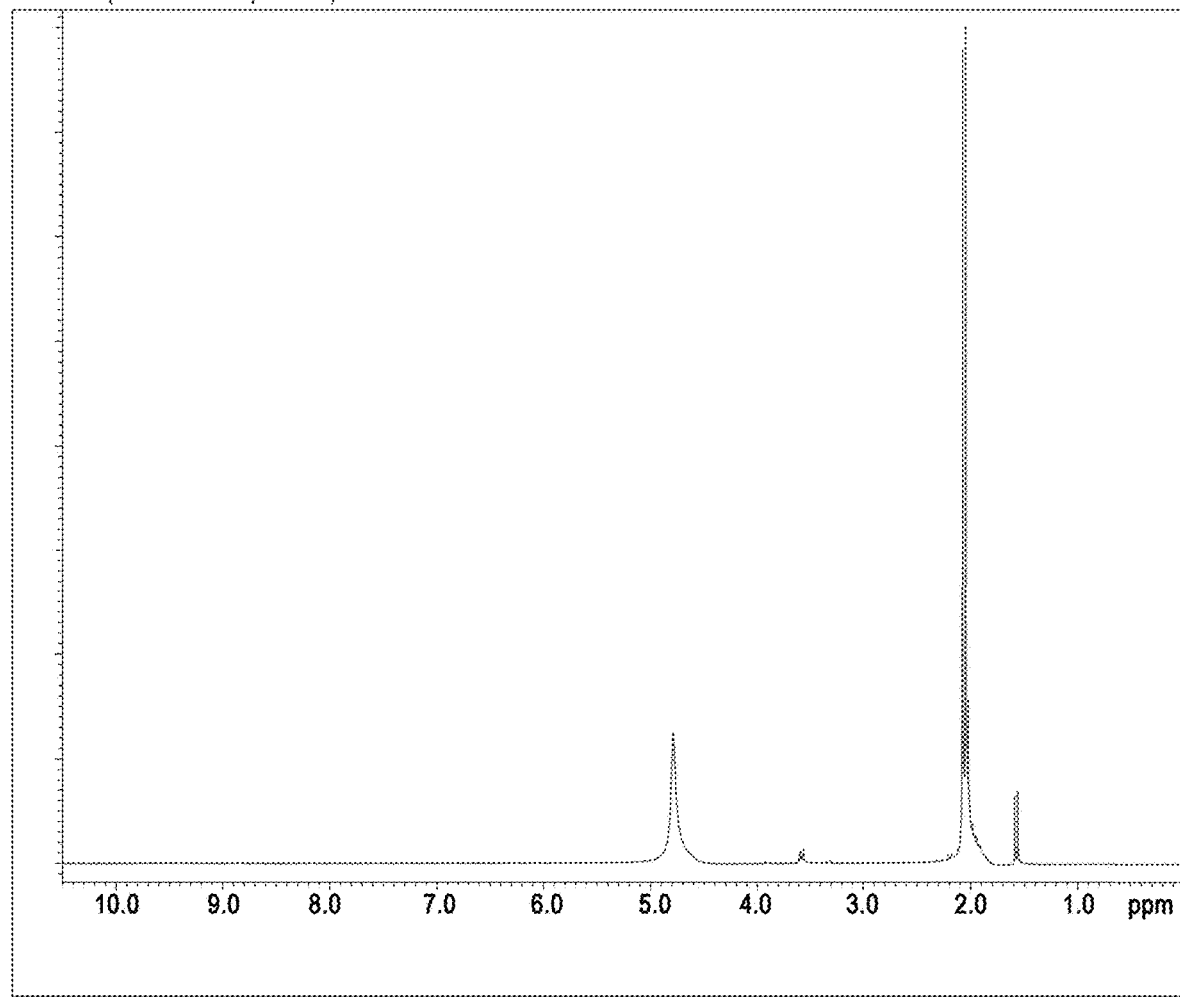

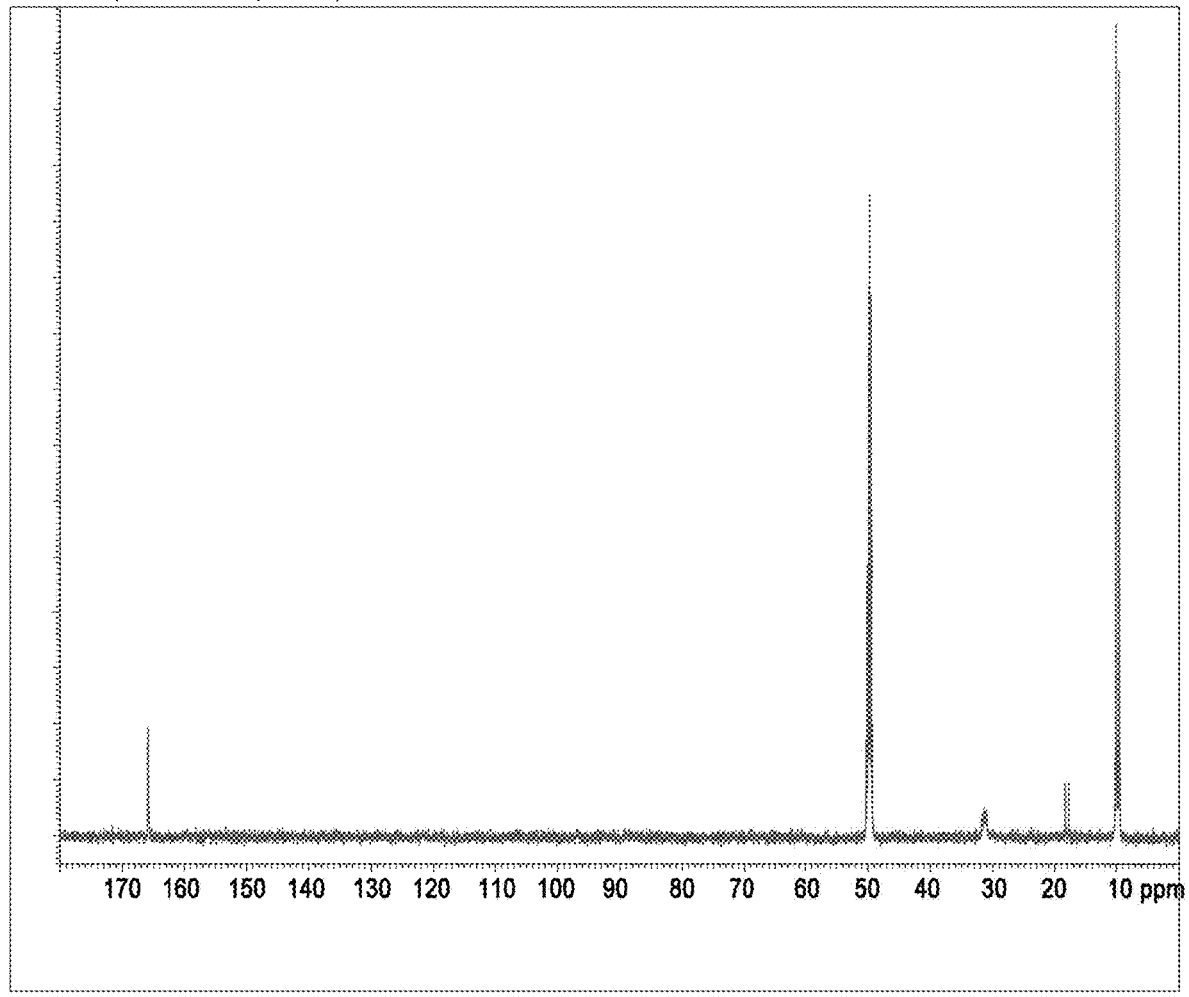

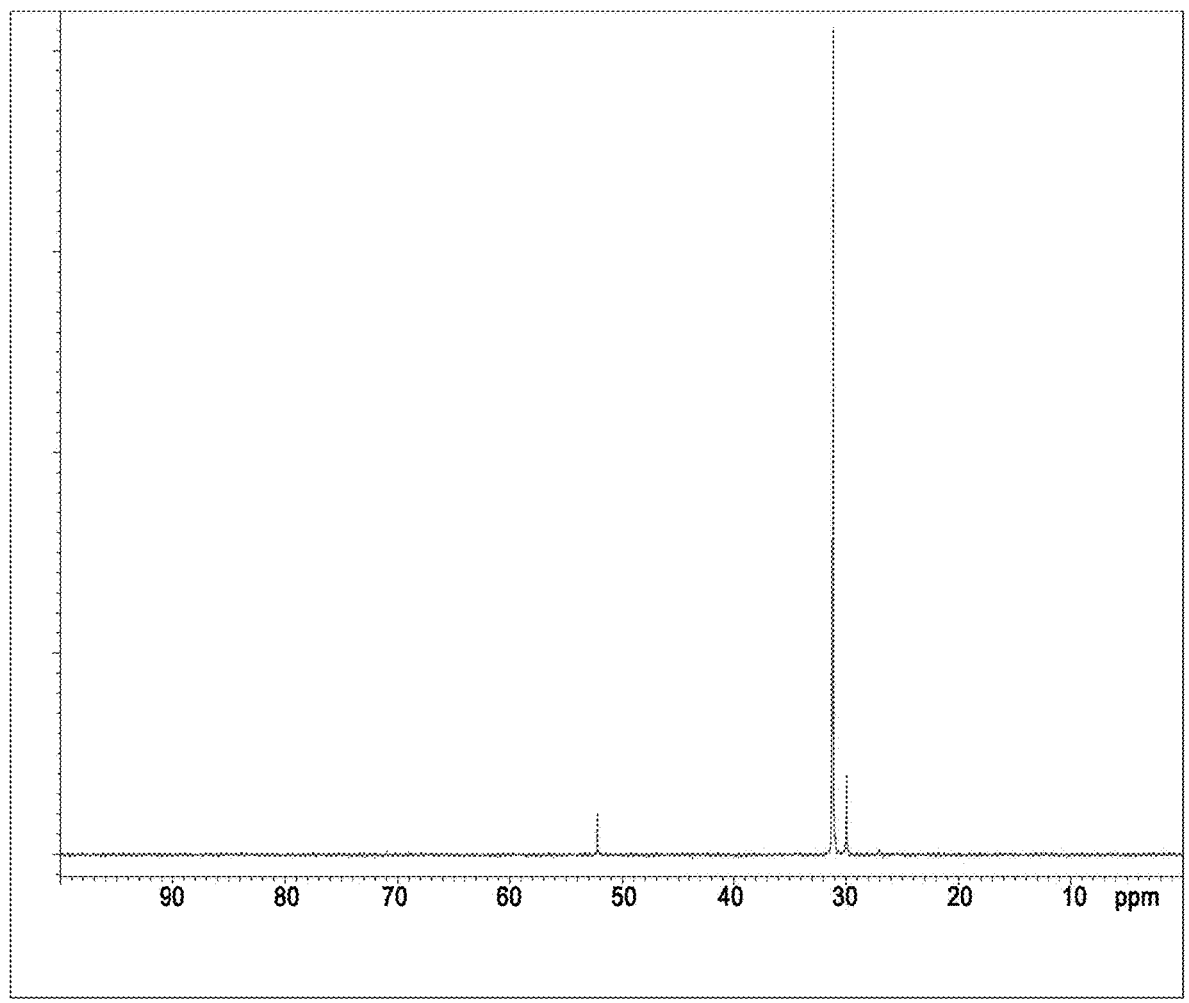
[Fig. 1-2]
C: Phosphorus (Chemical compound 1)

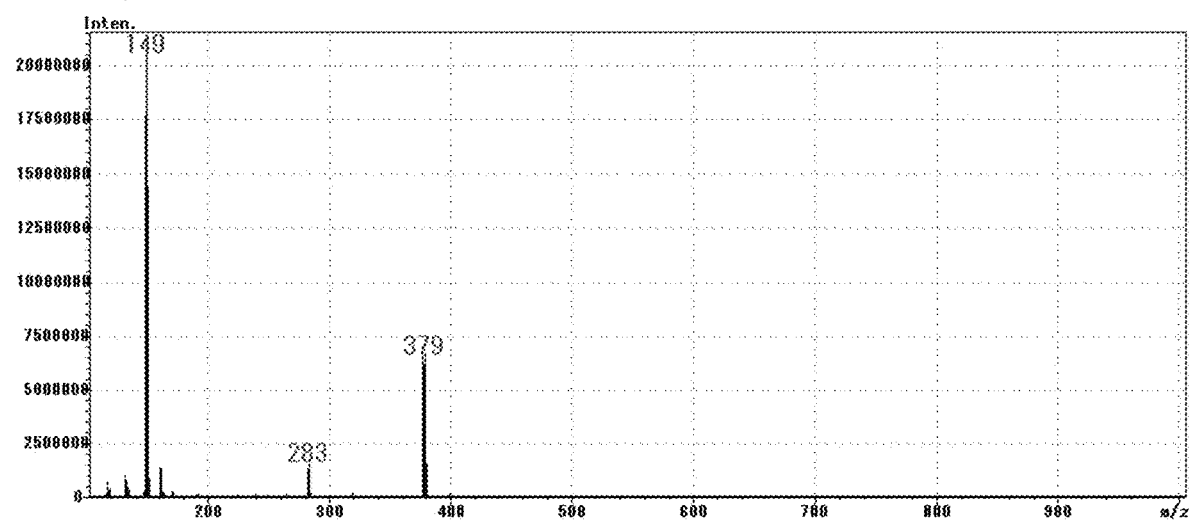
[Fig. 1-2]
D: ESI-MS (Chemical compound 1)

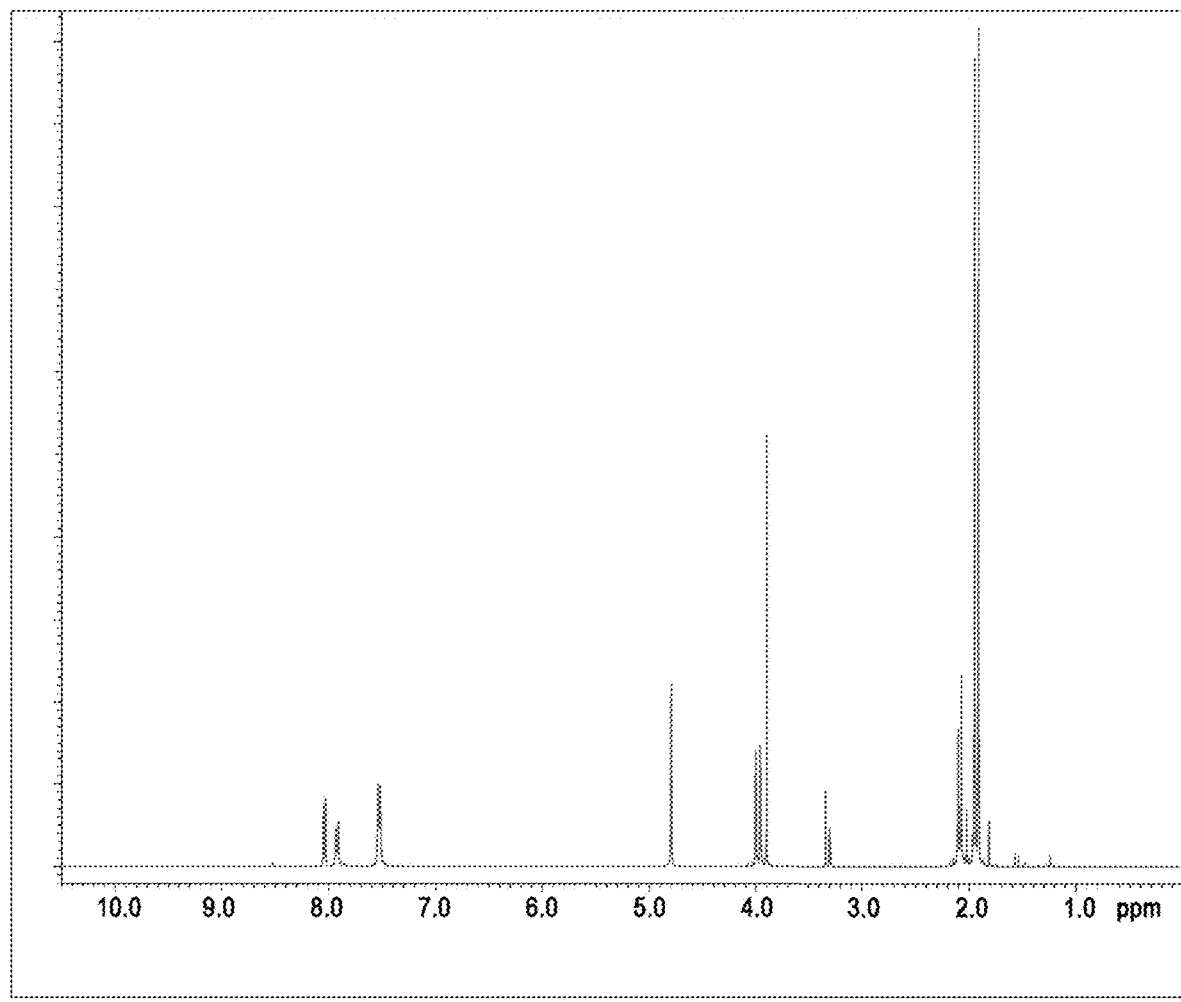
[Fig. 2-1]
A: Proton (Chemical compound 2)

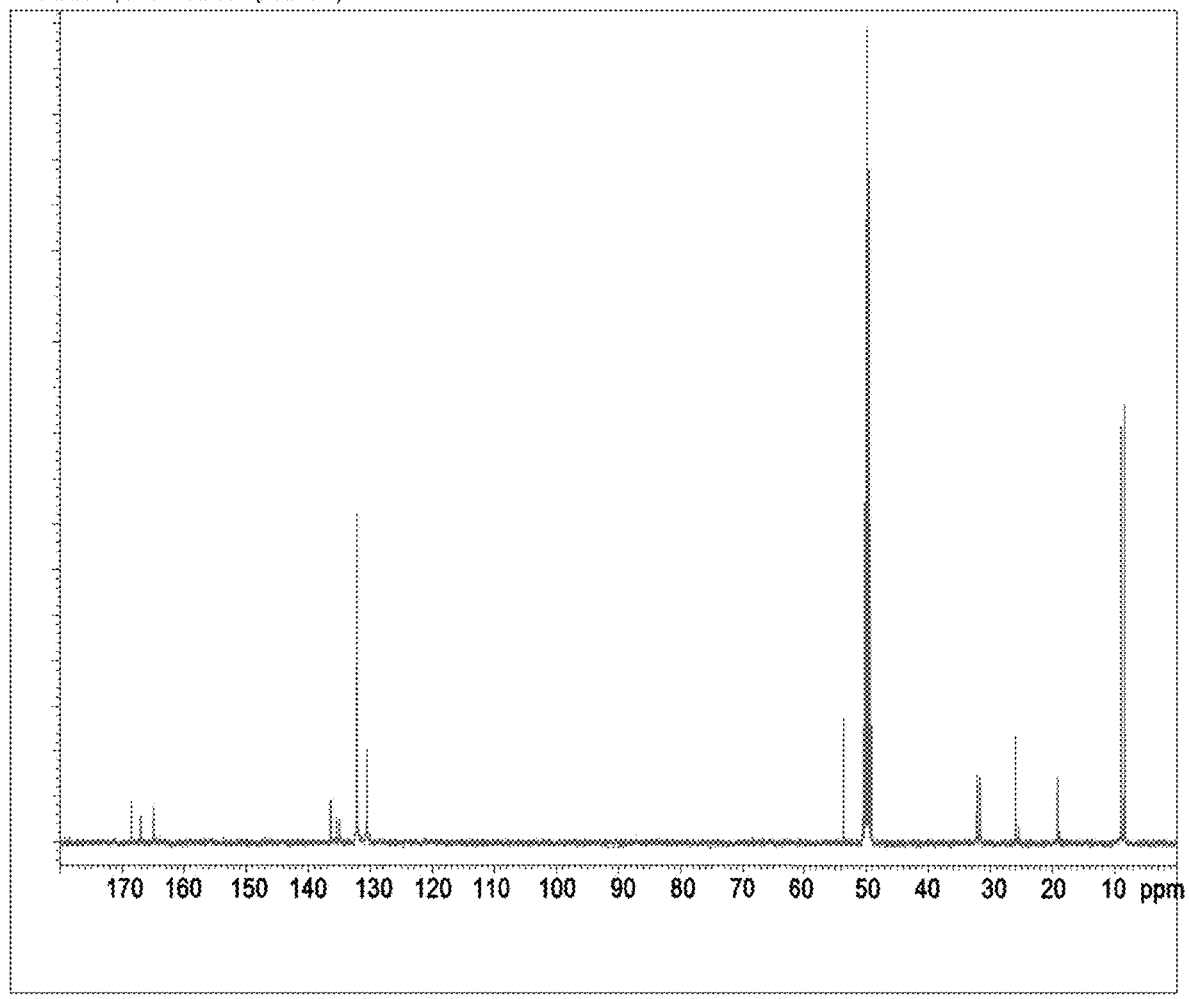
[Fig. 2-1]
B: Carbon (Chemical compound 2)

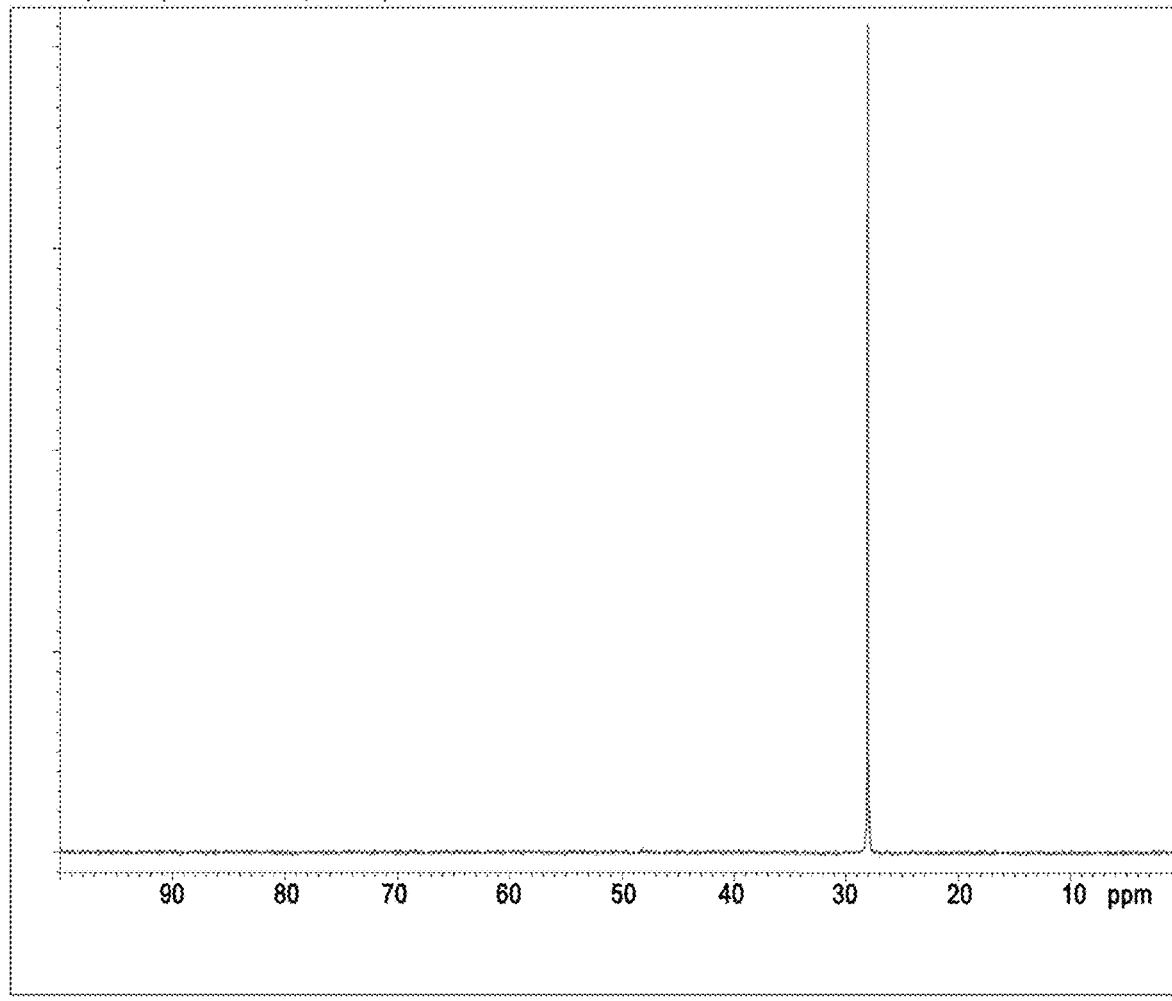

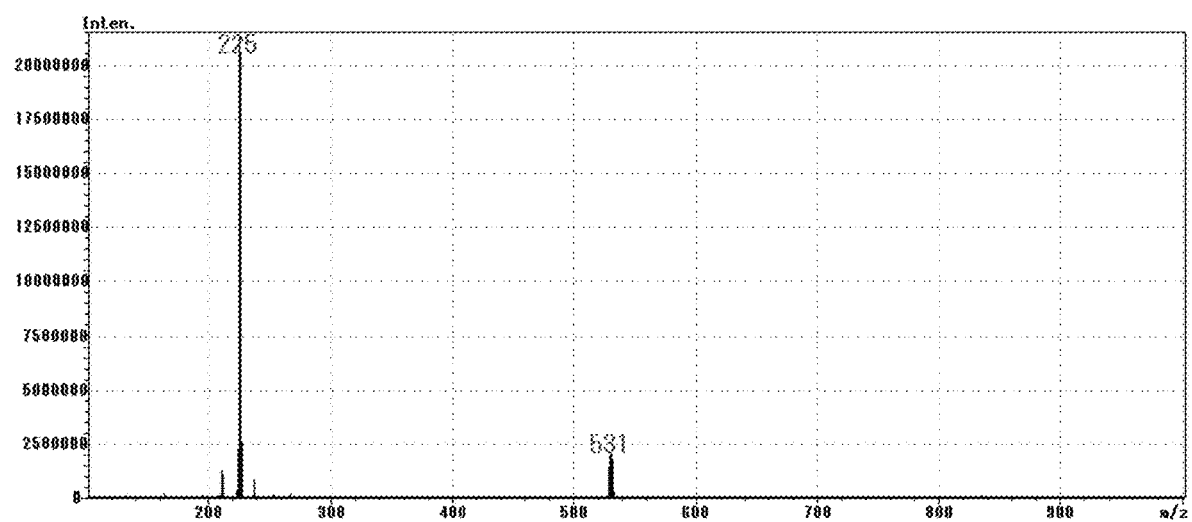

[Fig. 3-1]
A: Proton (Chemical compound 3)
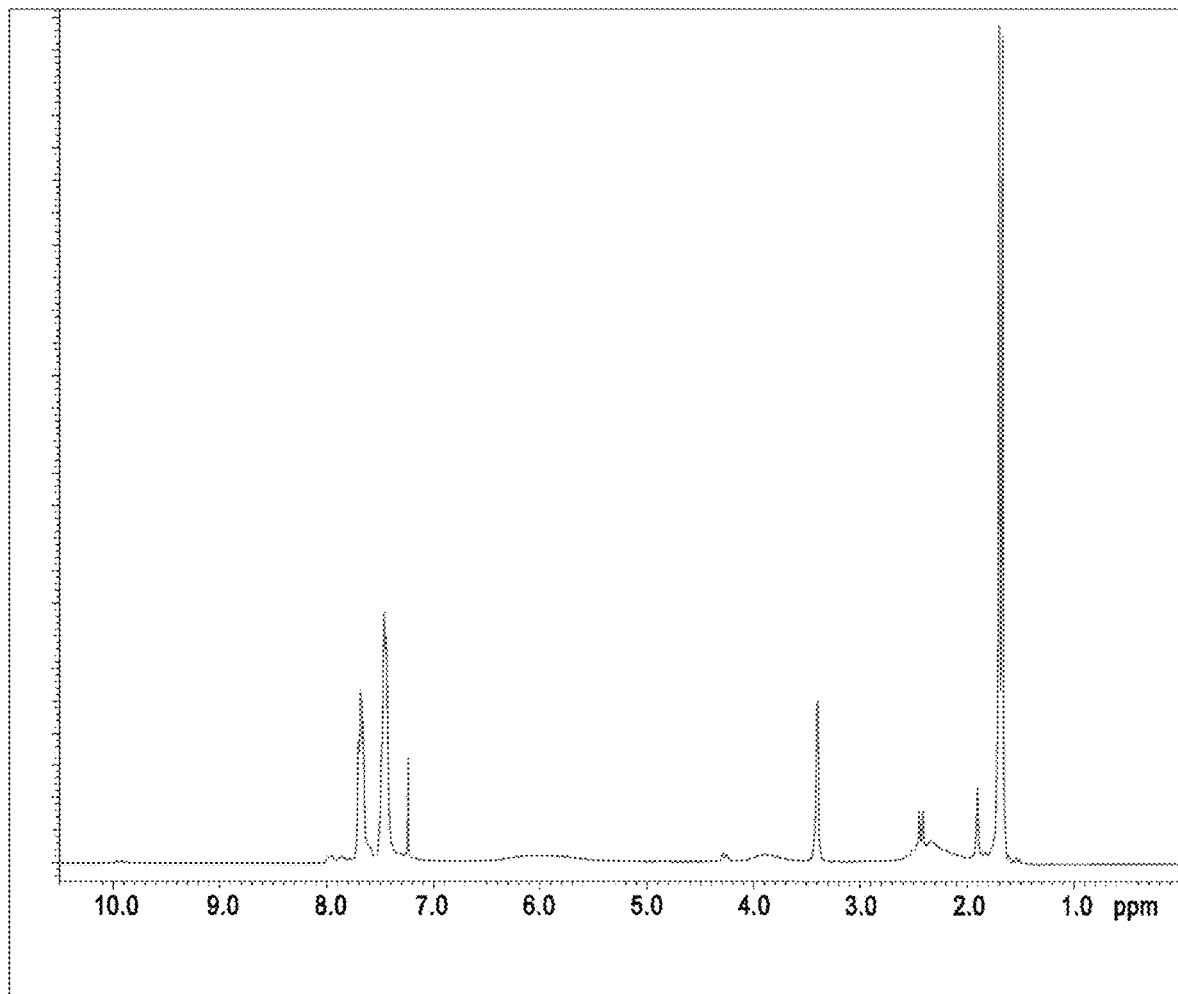

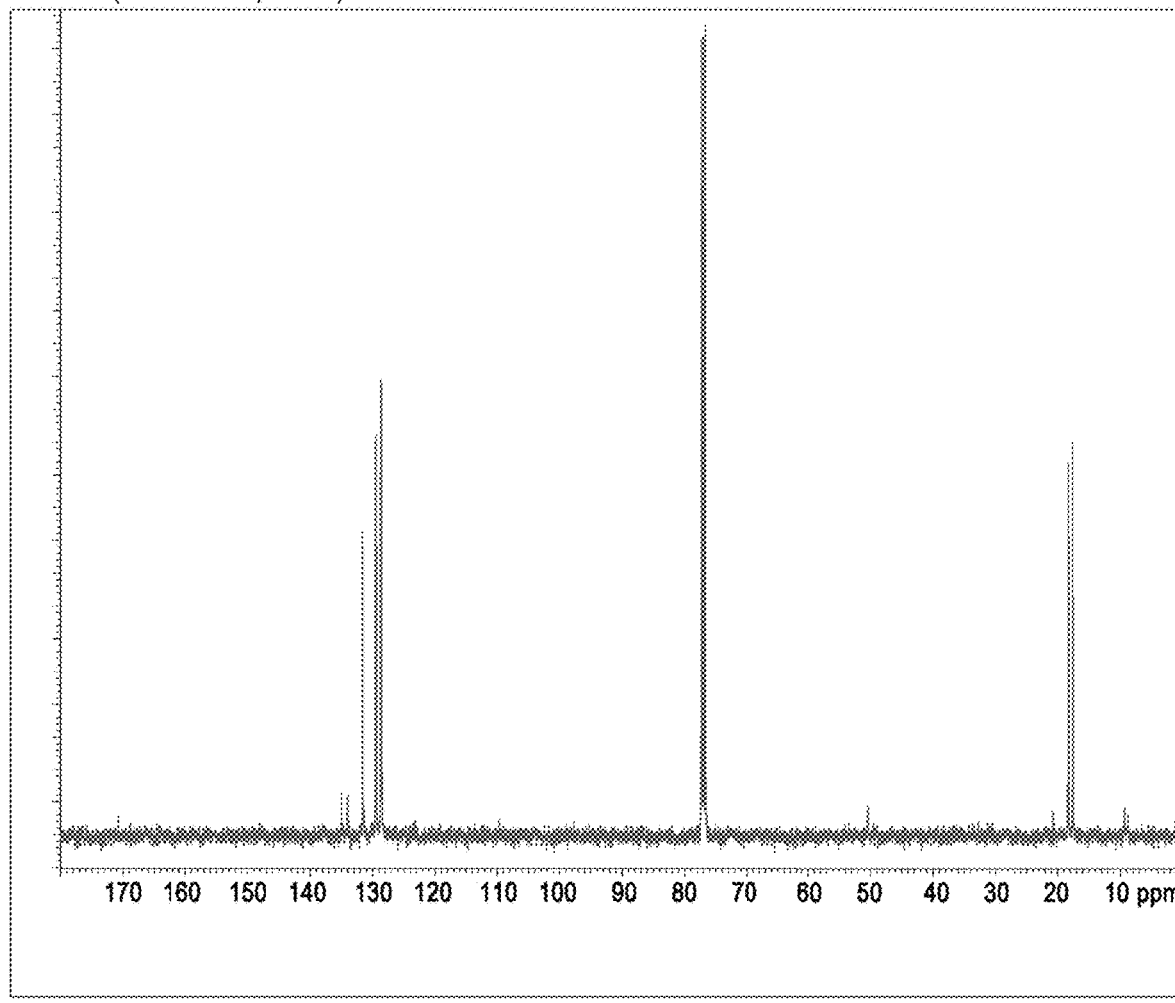

[Fig. 3-2]
C: Phosphorus (Chemical compound 3)
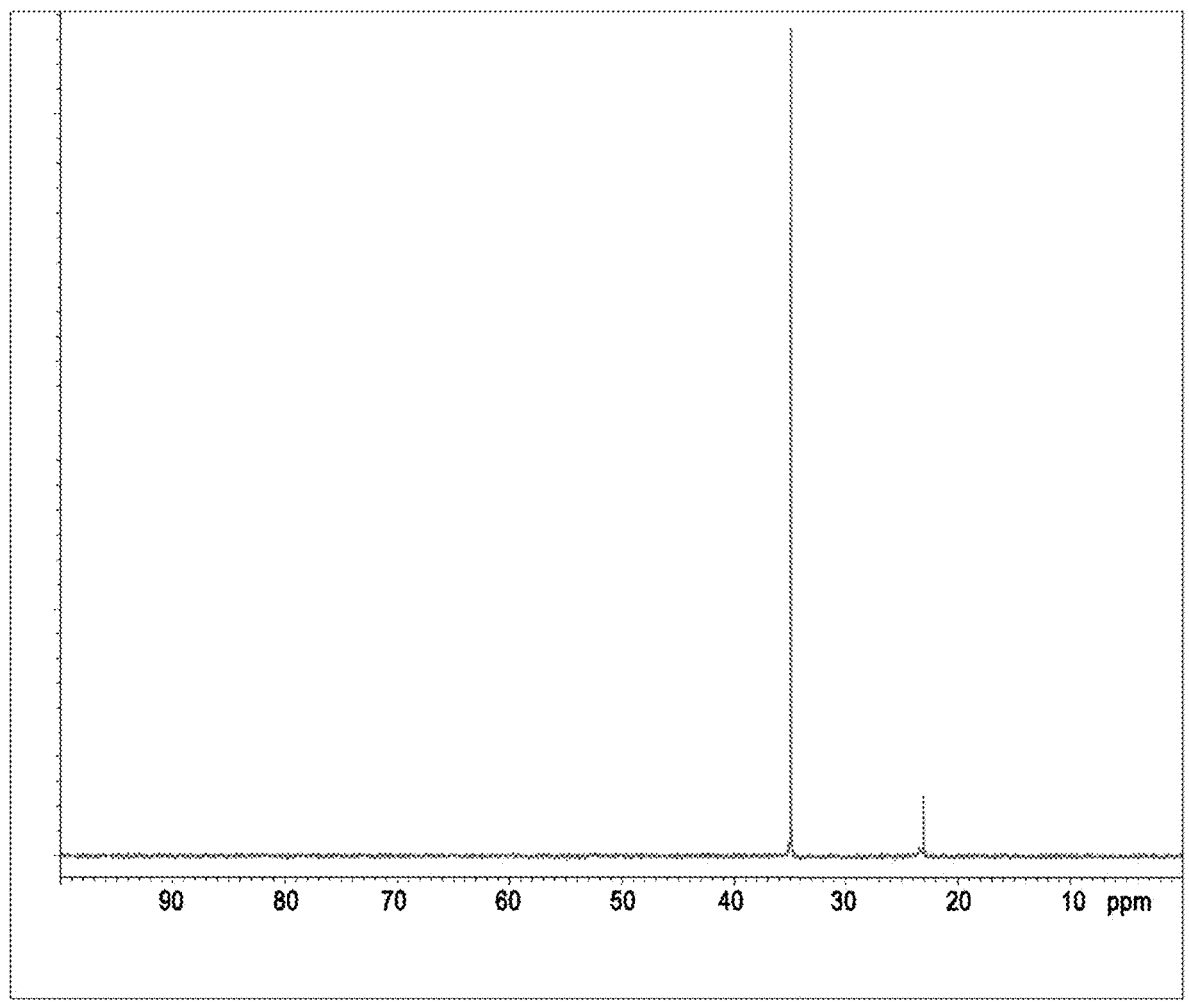

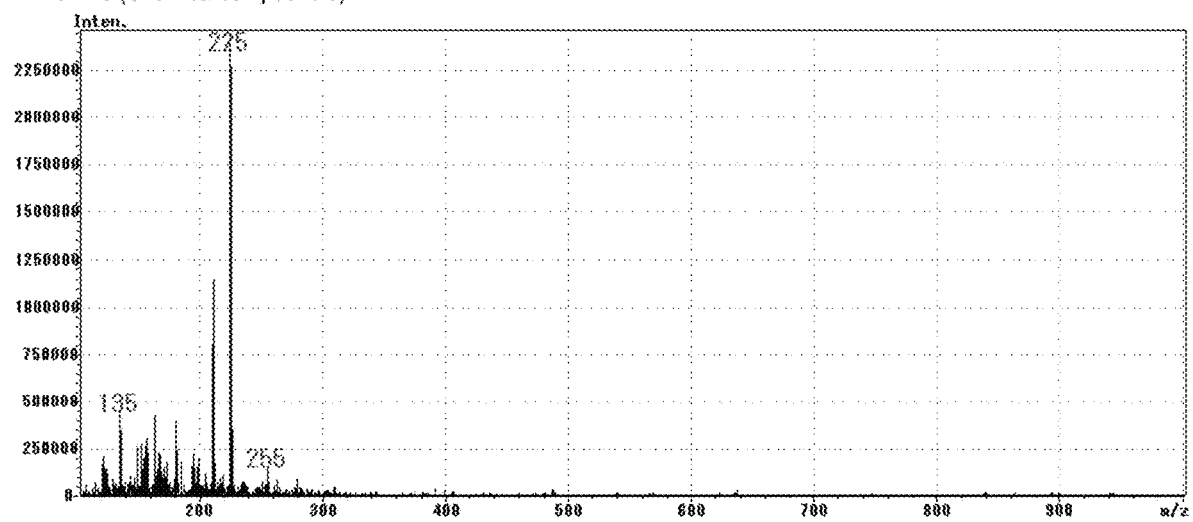
[Fig. 3-2]
D: ESI-MS (Chemical compound 3)

[Fig. 4-1]
A: Proton (Chemical compound 4)
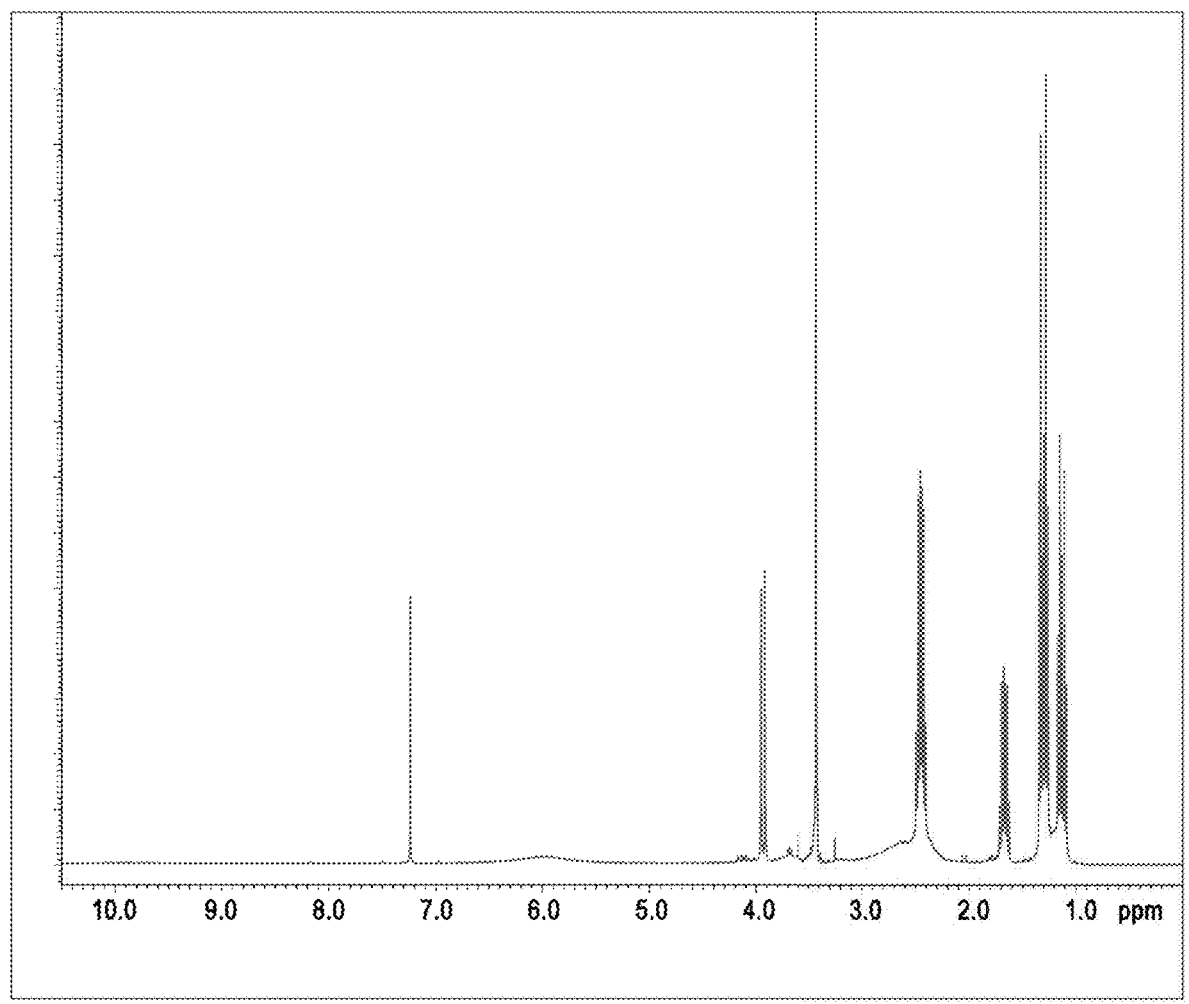

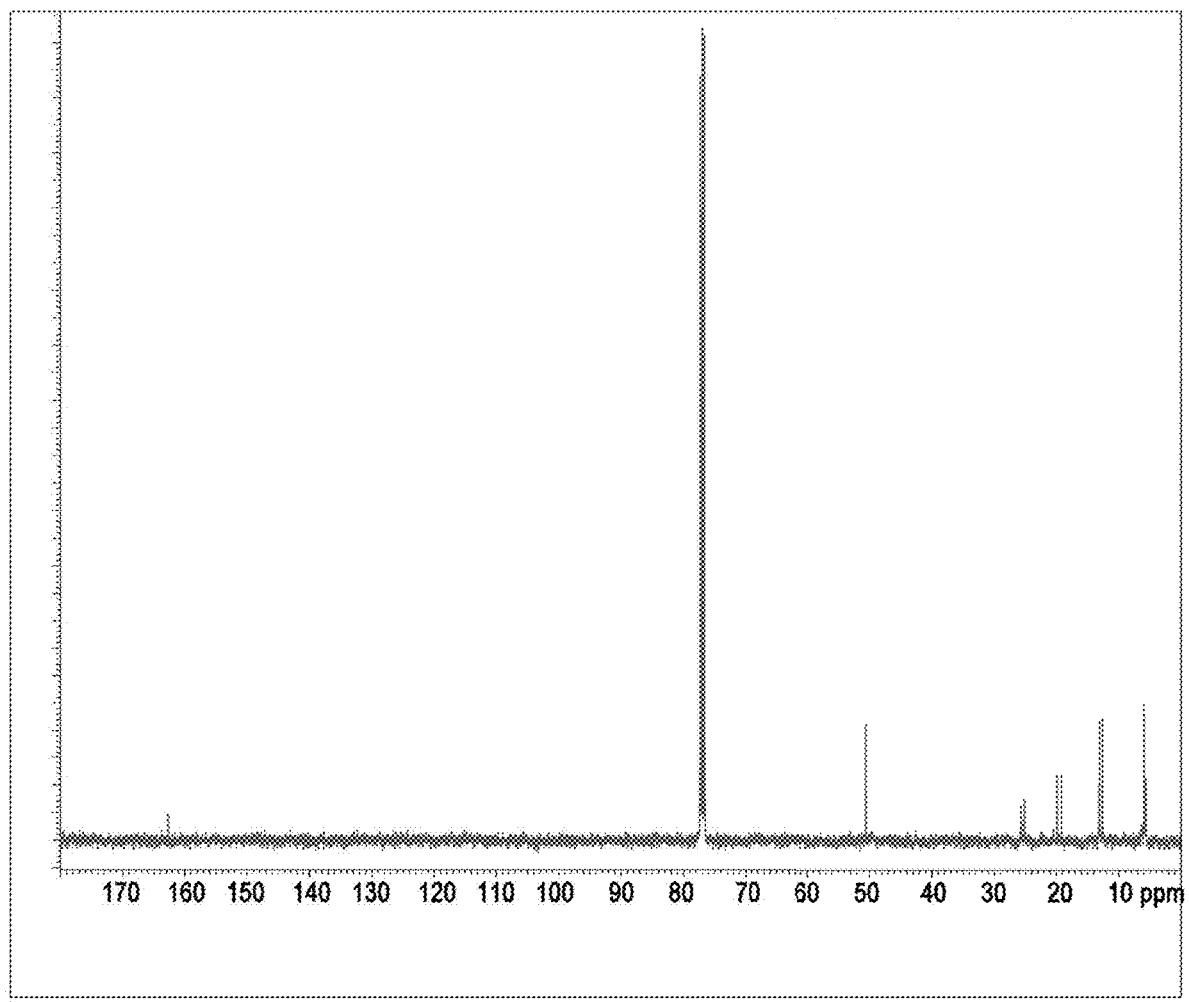
[Fig. 4-1]
B: Carbon (Chemical compound 4)

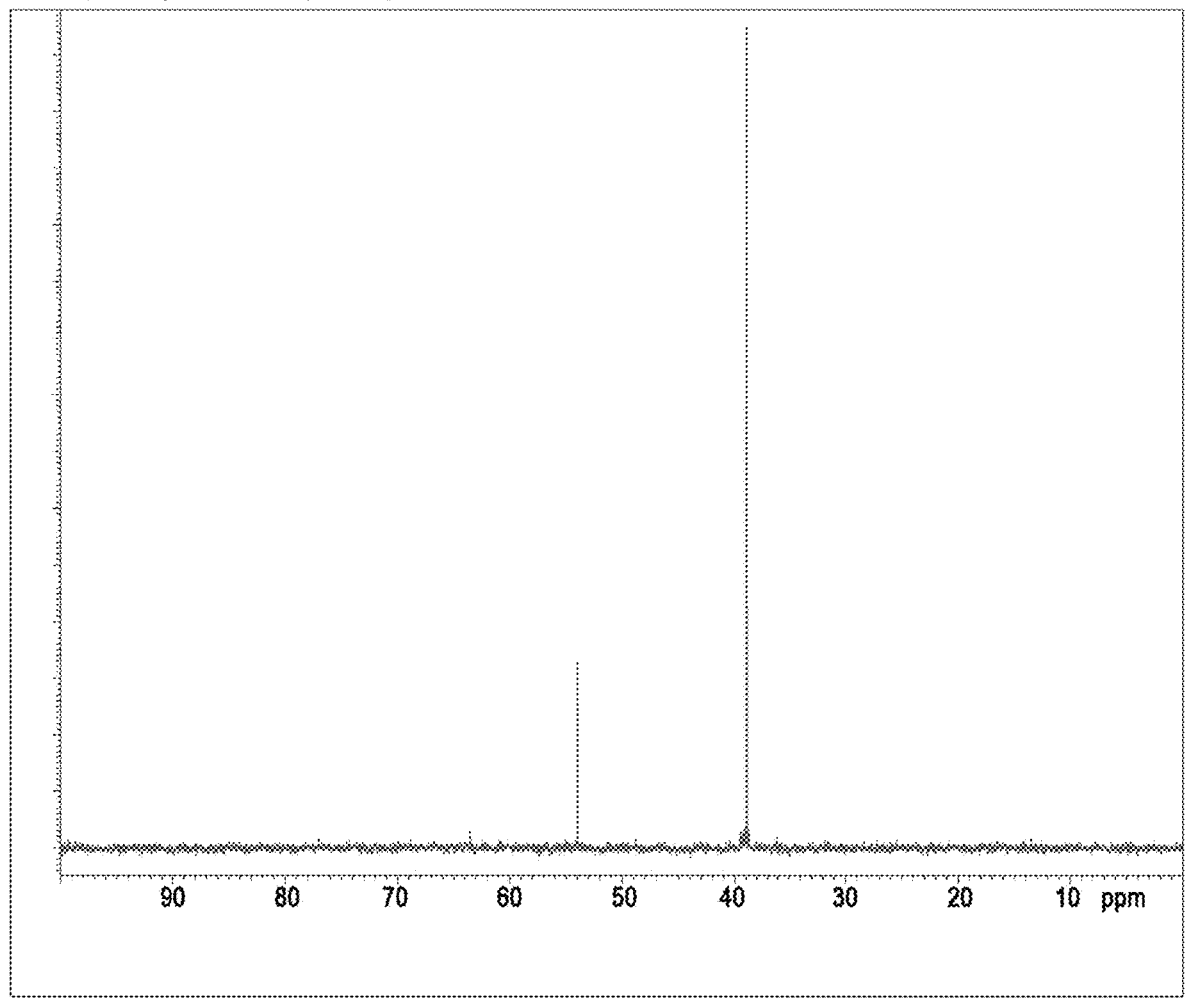

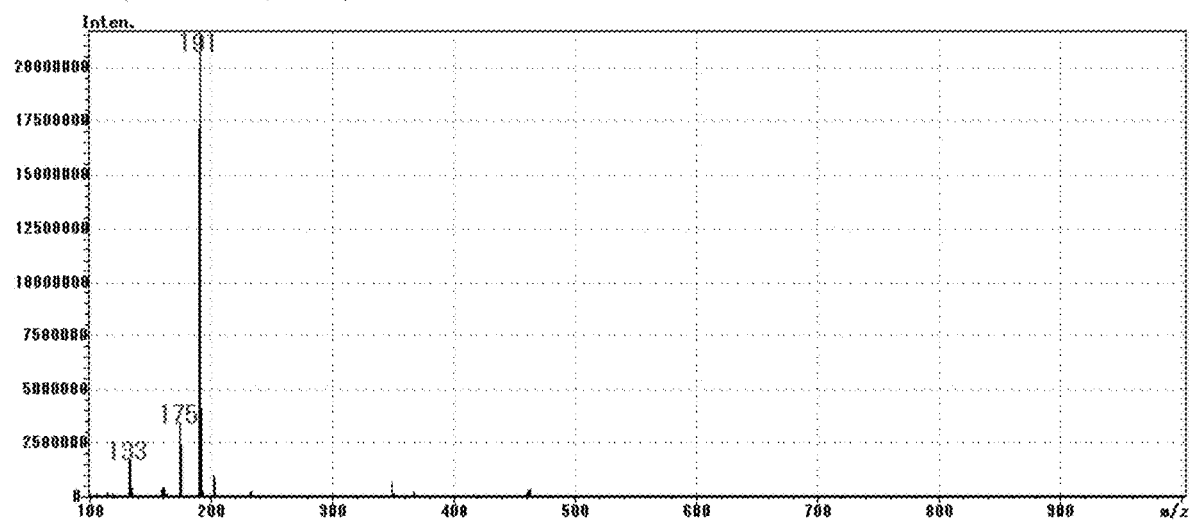
[Fig. 4-2]
D: ESI-MS (Chemical compound 4)

[Fig. 5-1]
A: Proton (Chemical compound 5)
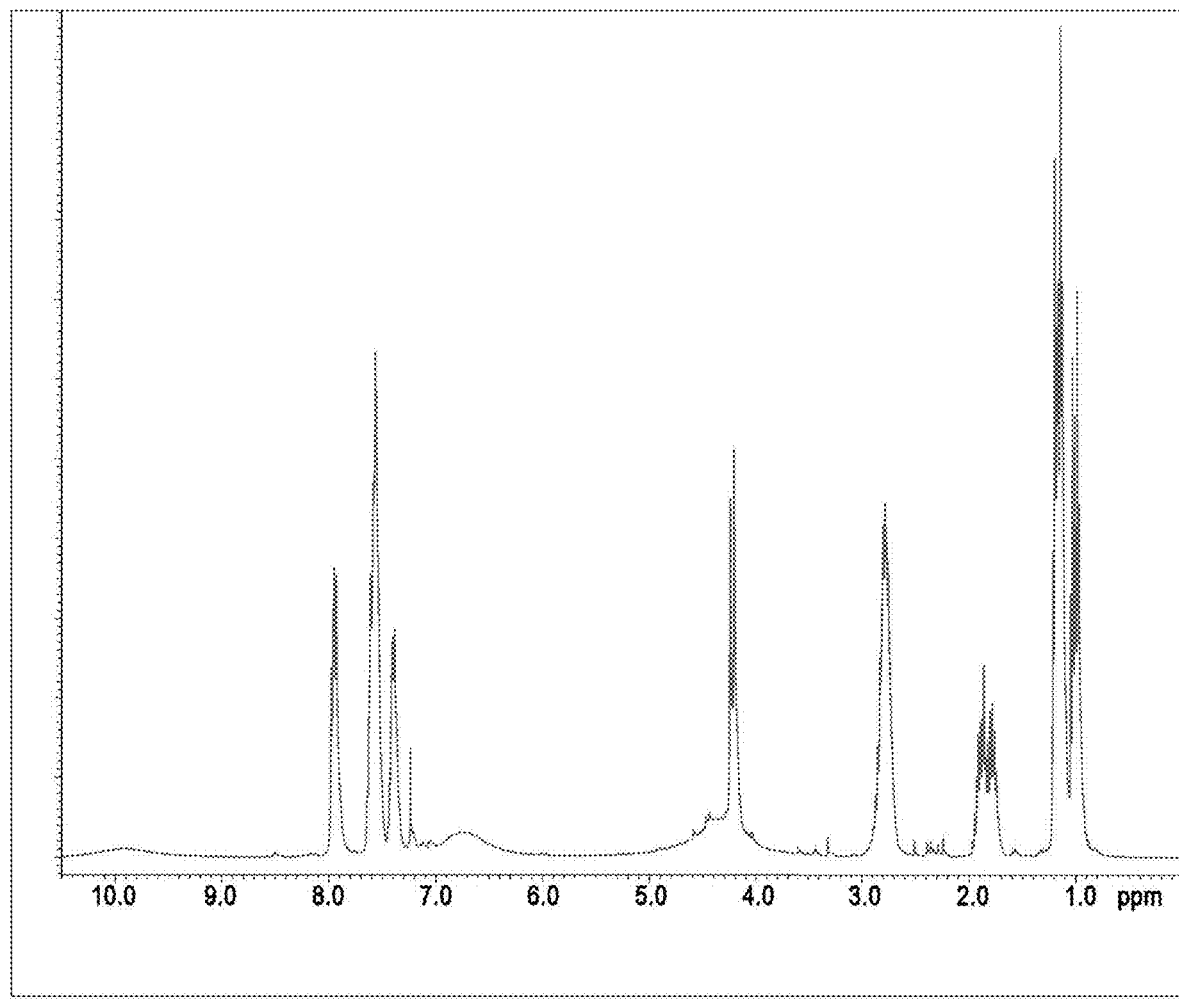

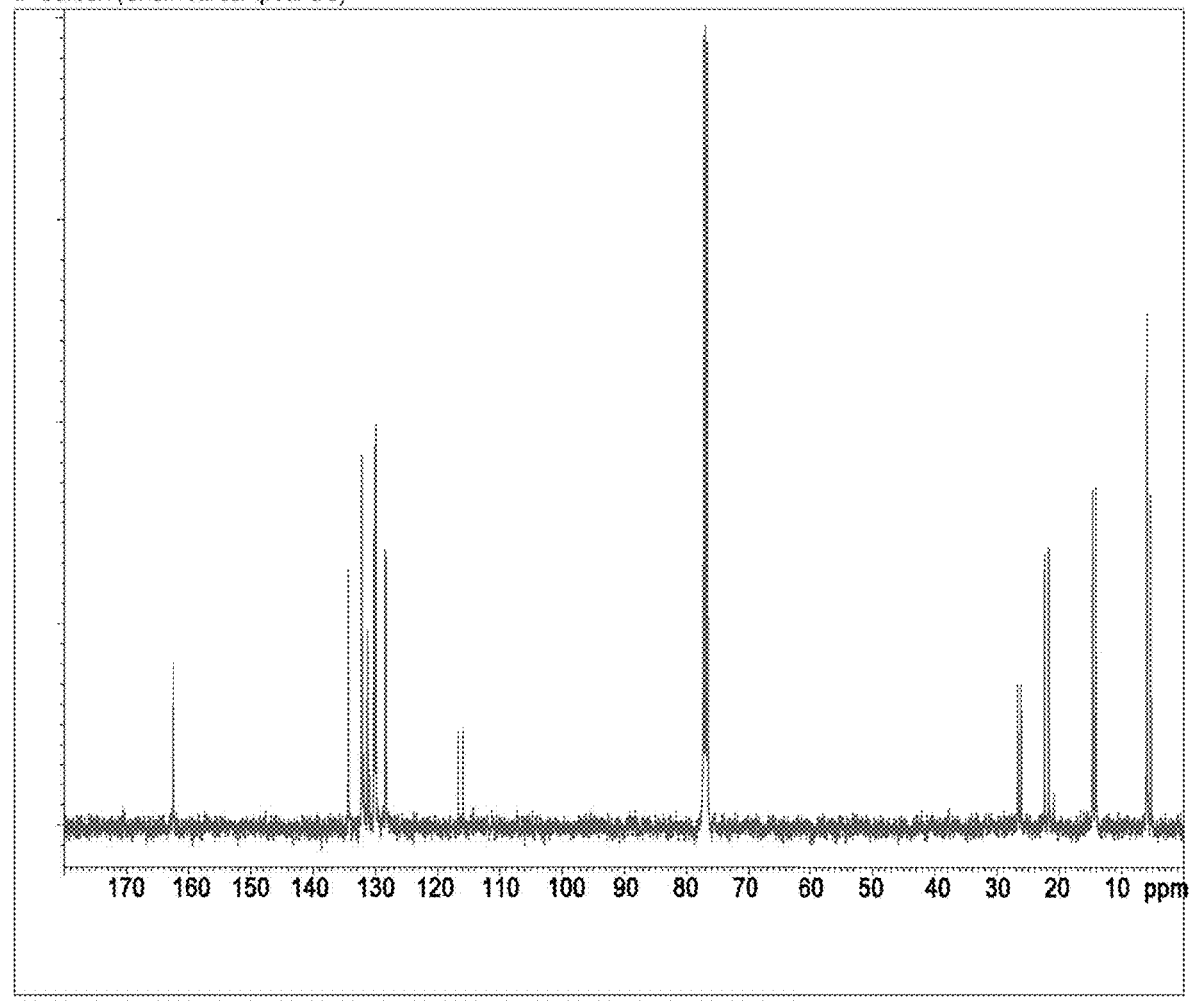

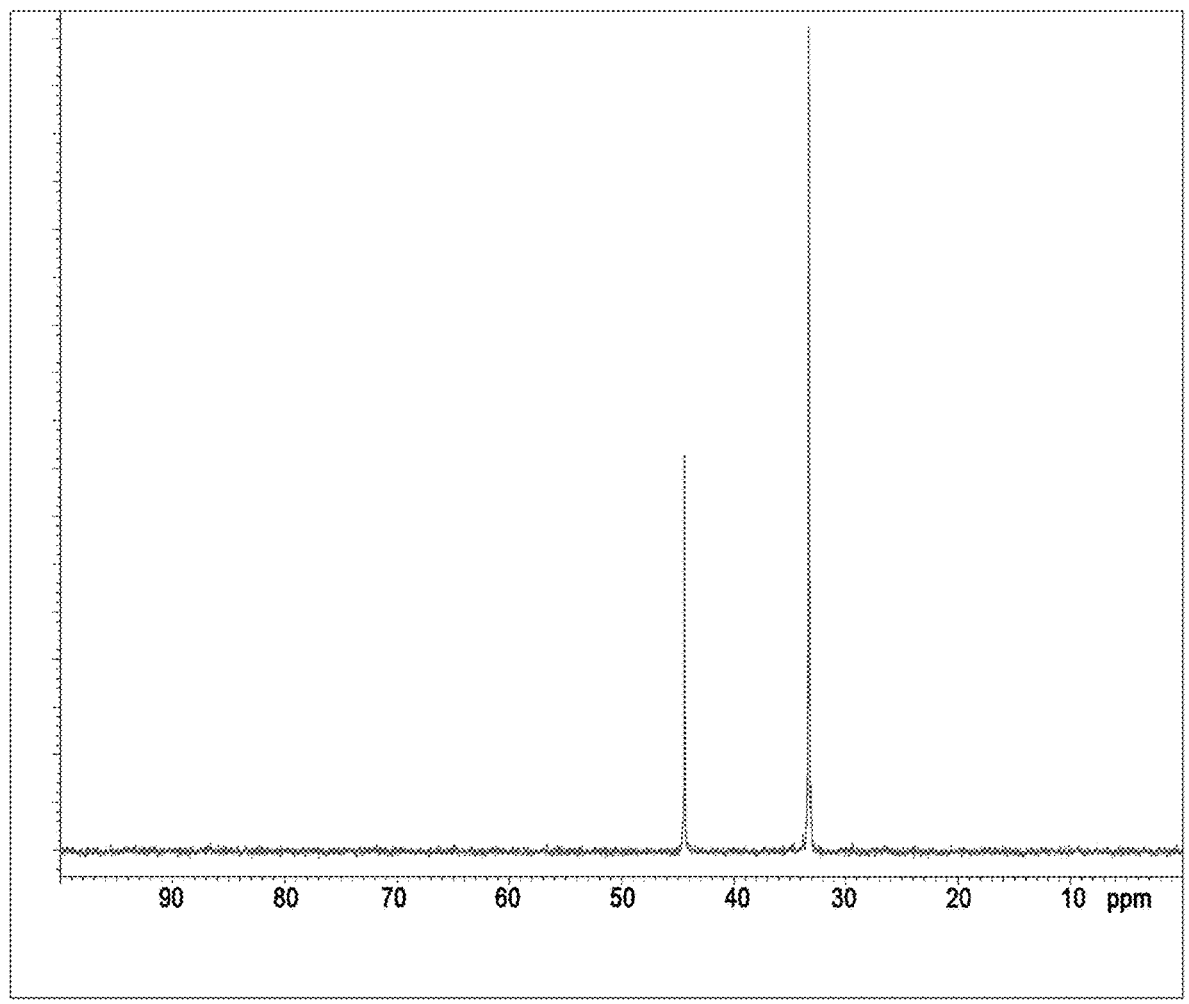

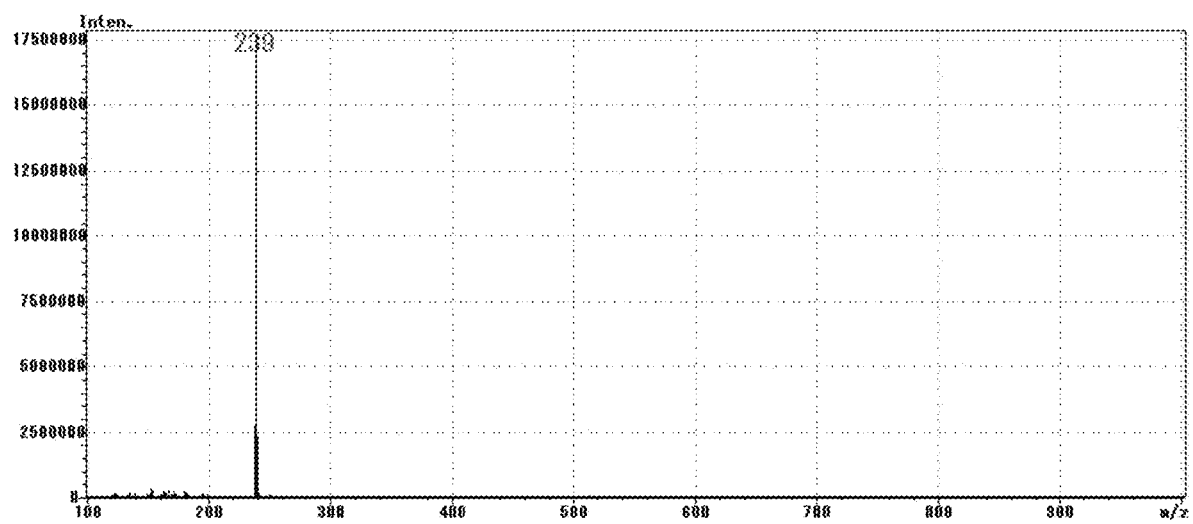
[Fig. 5-2]
D: ESI-MS (Chemical compound 4)

[Fig. 6-1]
A: Proton (Chemical compound 6)
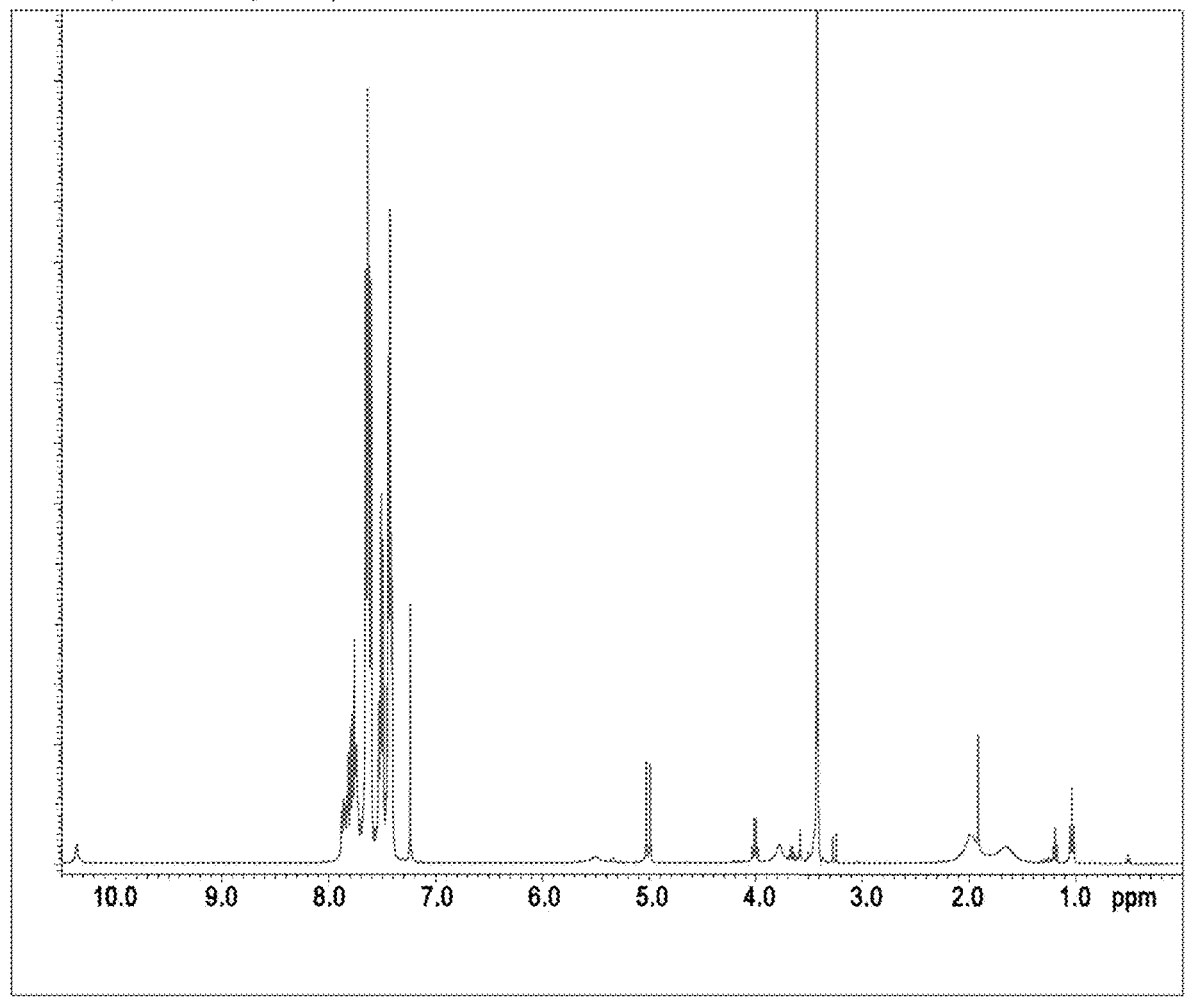

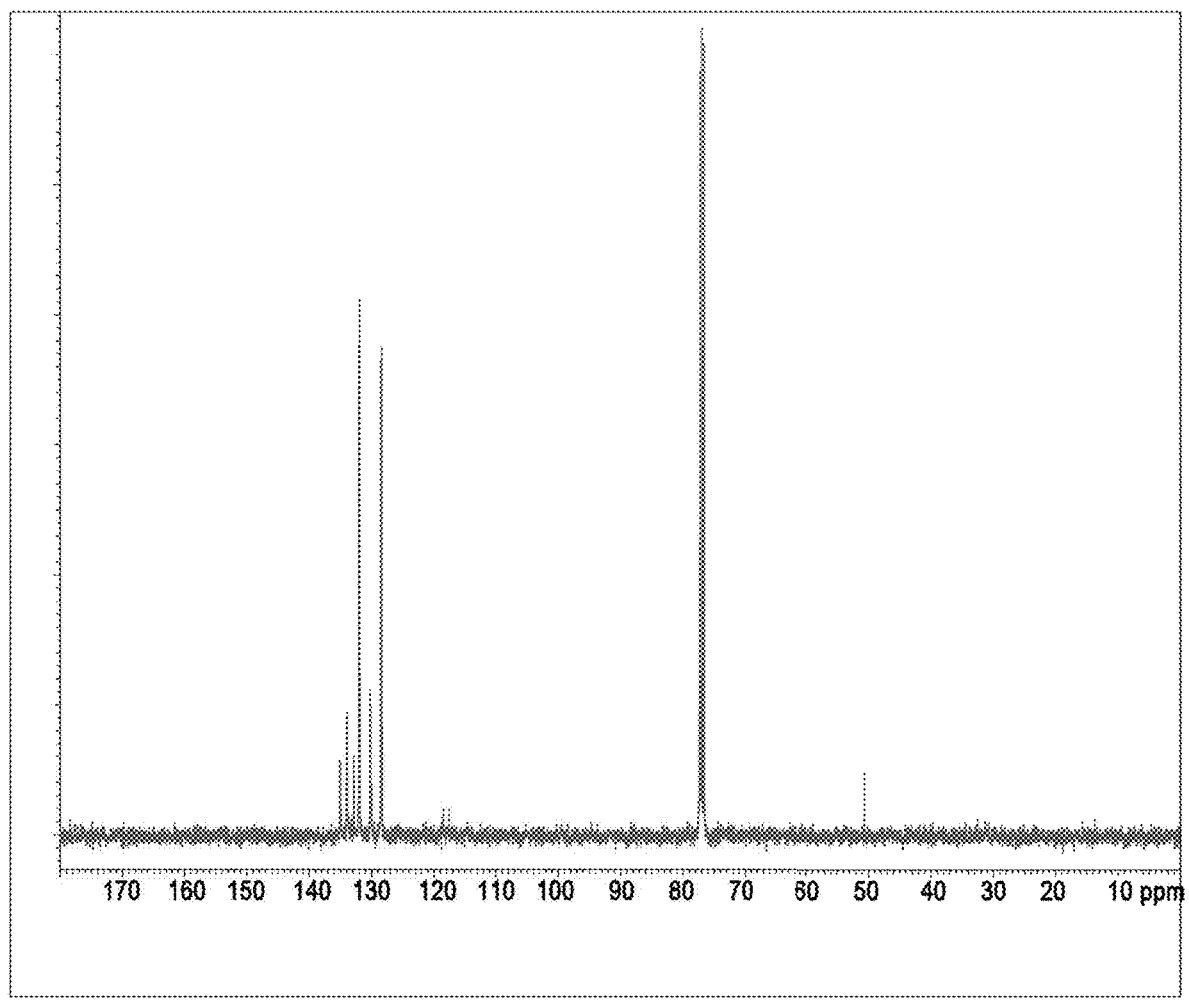
[Fig. 6-1]
B: Carbon (Chemical compound 6)

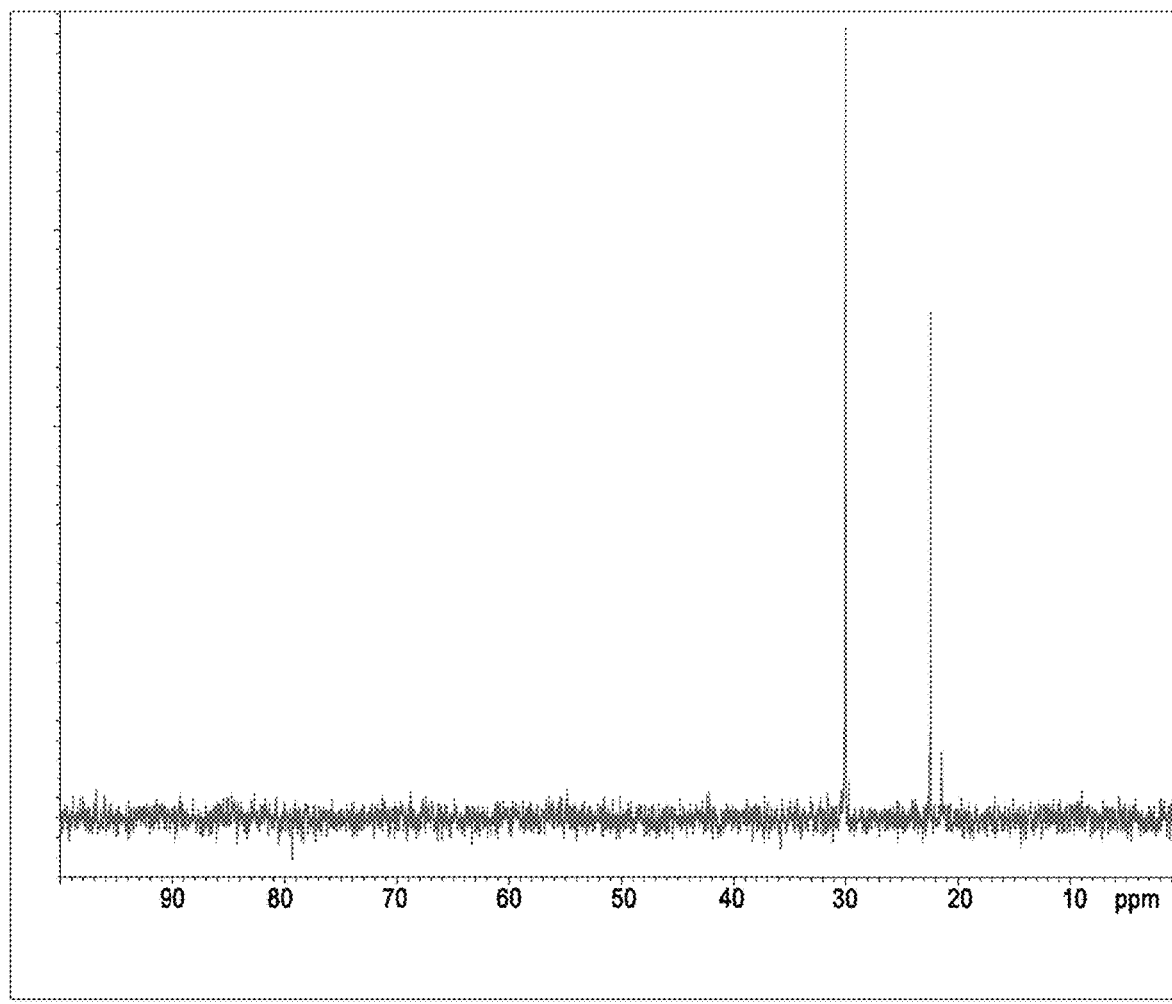

[Fig. 6-2]
D: ESI-MS (Chemical compound 6)
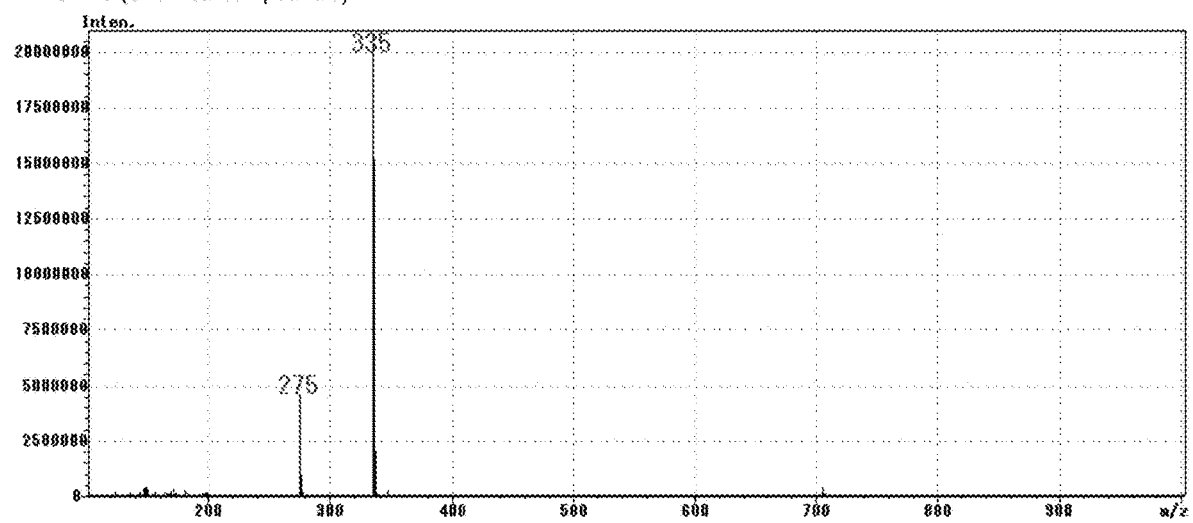

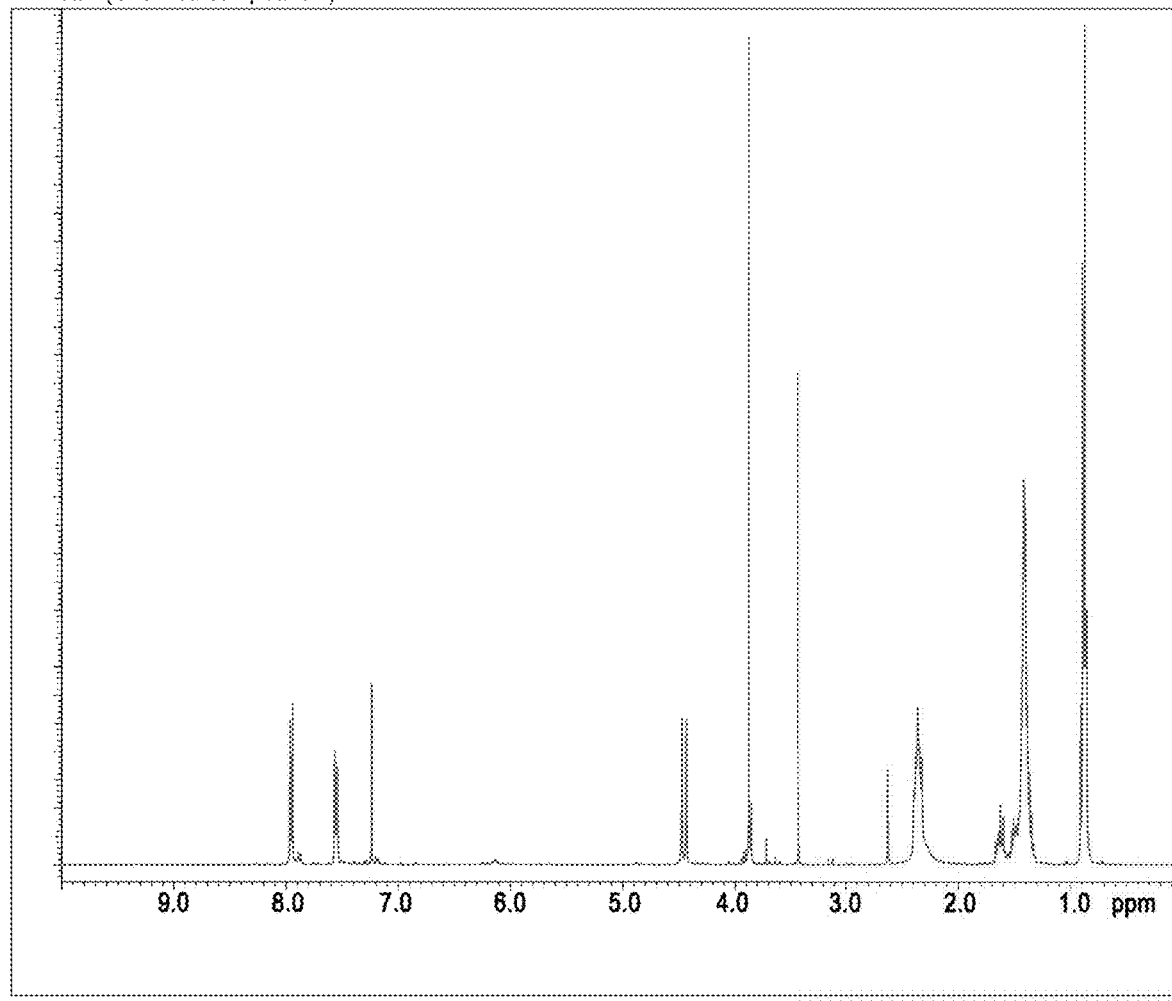

[Fig. 7-1]
B: Carbon (Chemical compound 7)
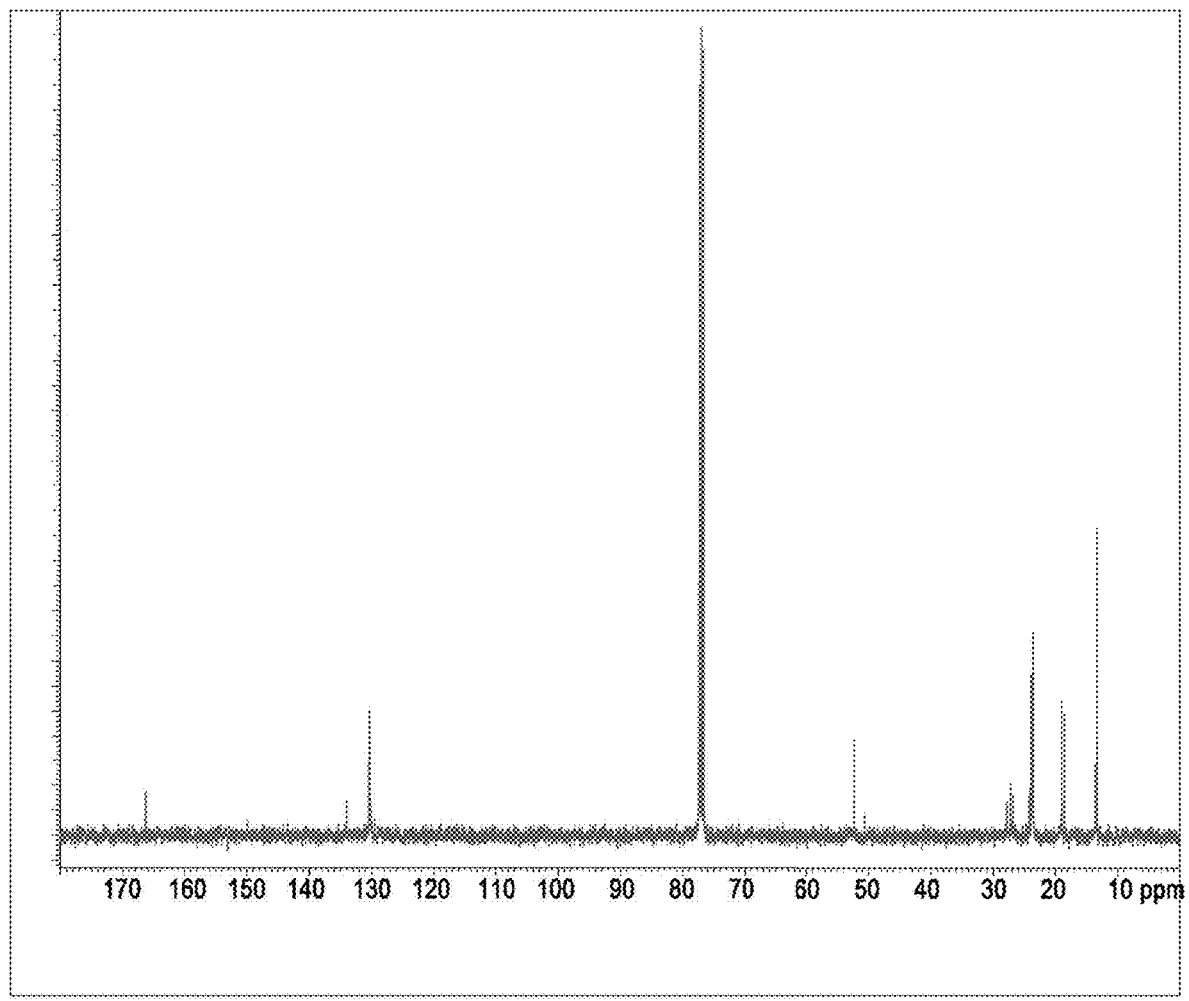

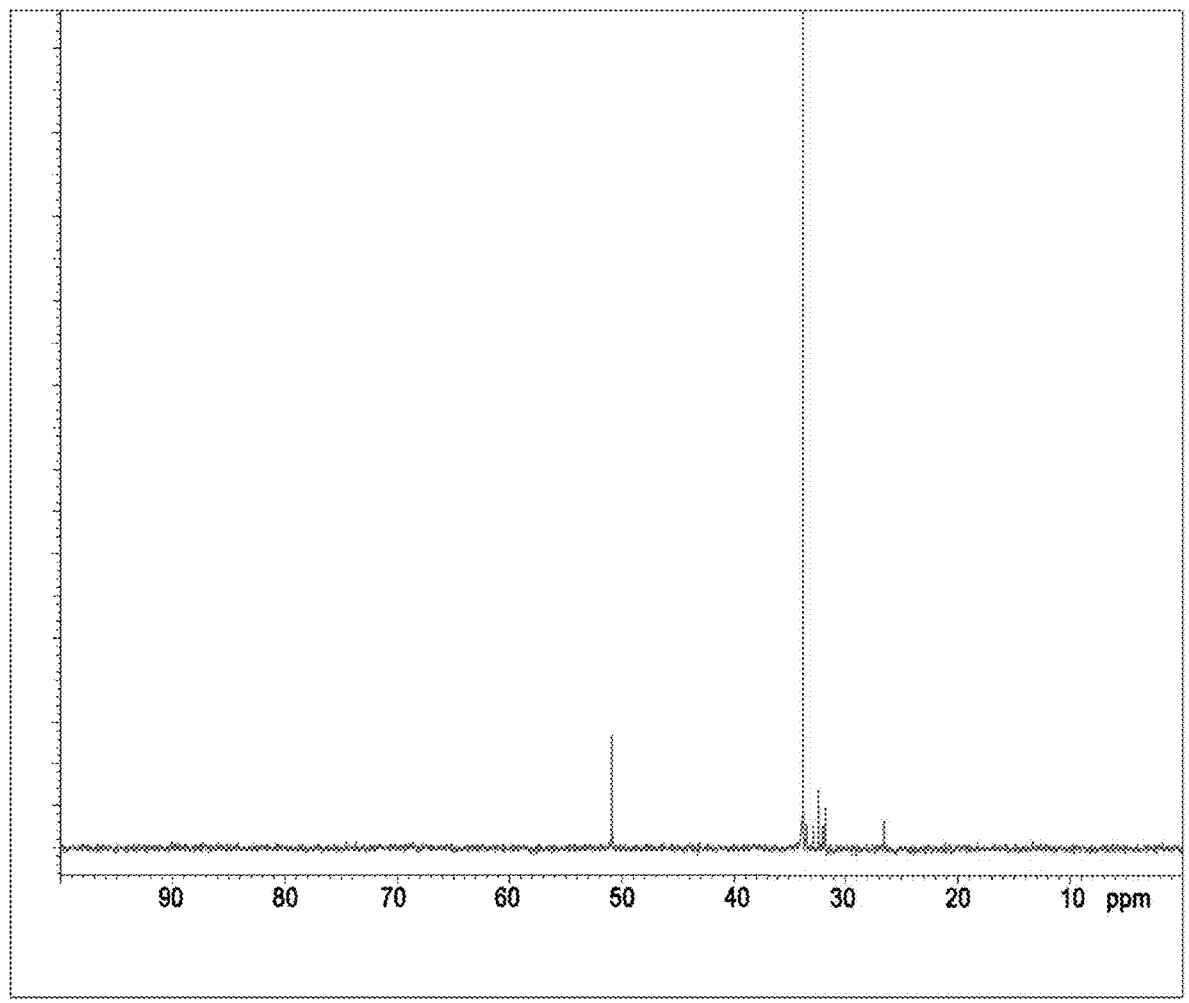

[Fig. 7-2]
D: ESI-MS (Chemical compound 7)
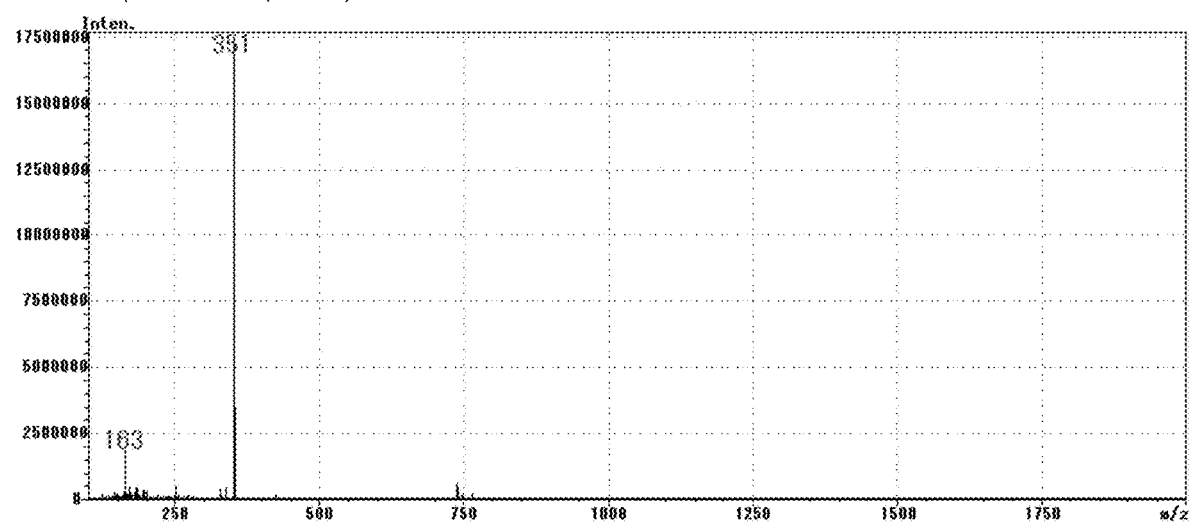

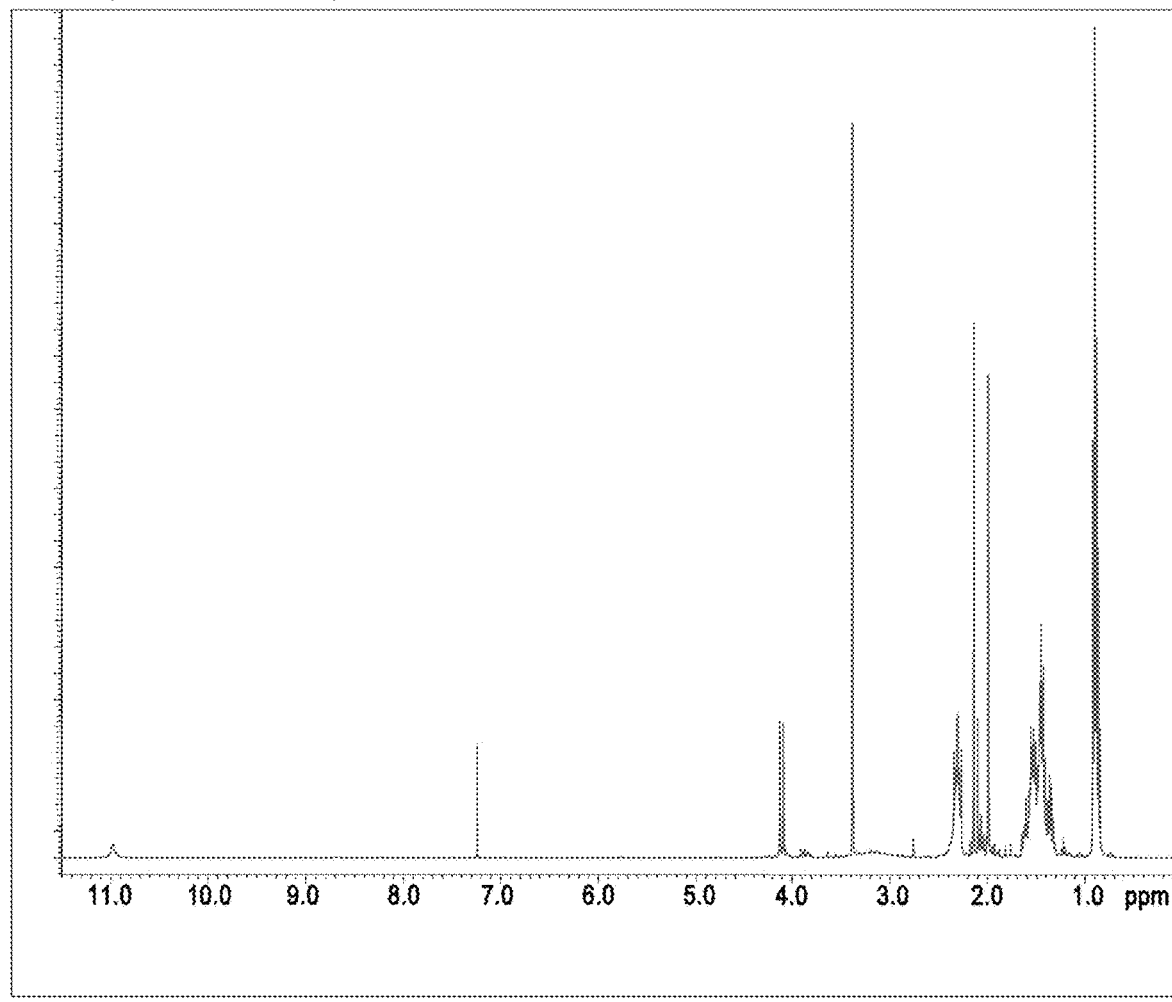
[Fig. 8-1]
A: Proton (Chemical compound 8)

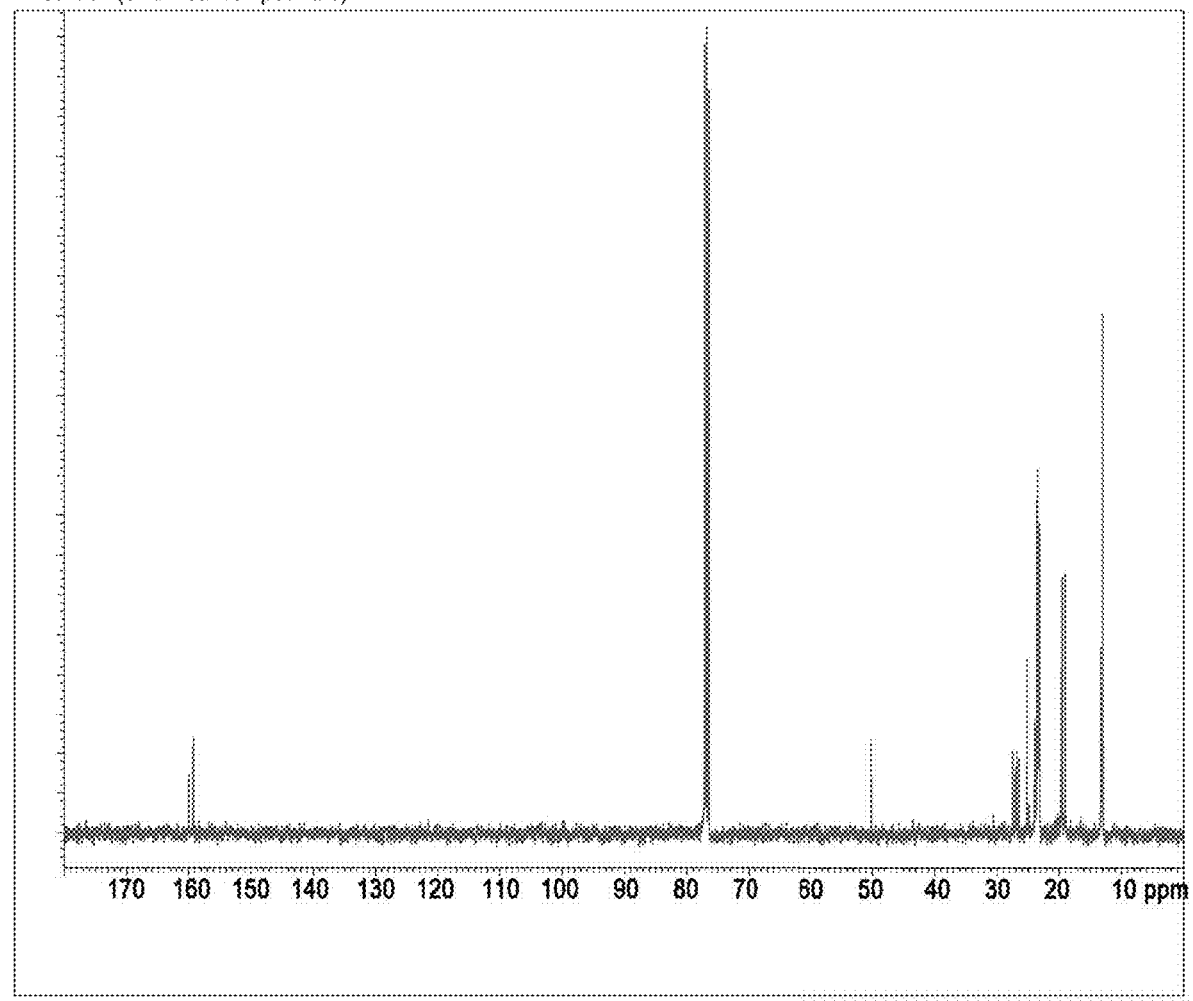
[Fig. 8-1]
B: Carbon (Chemical compound 8)

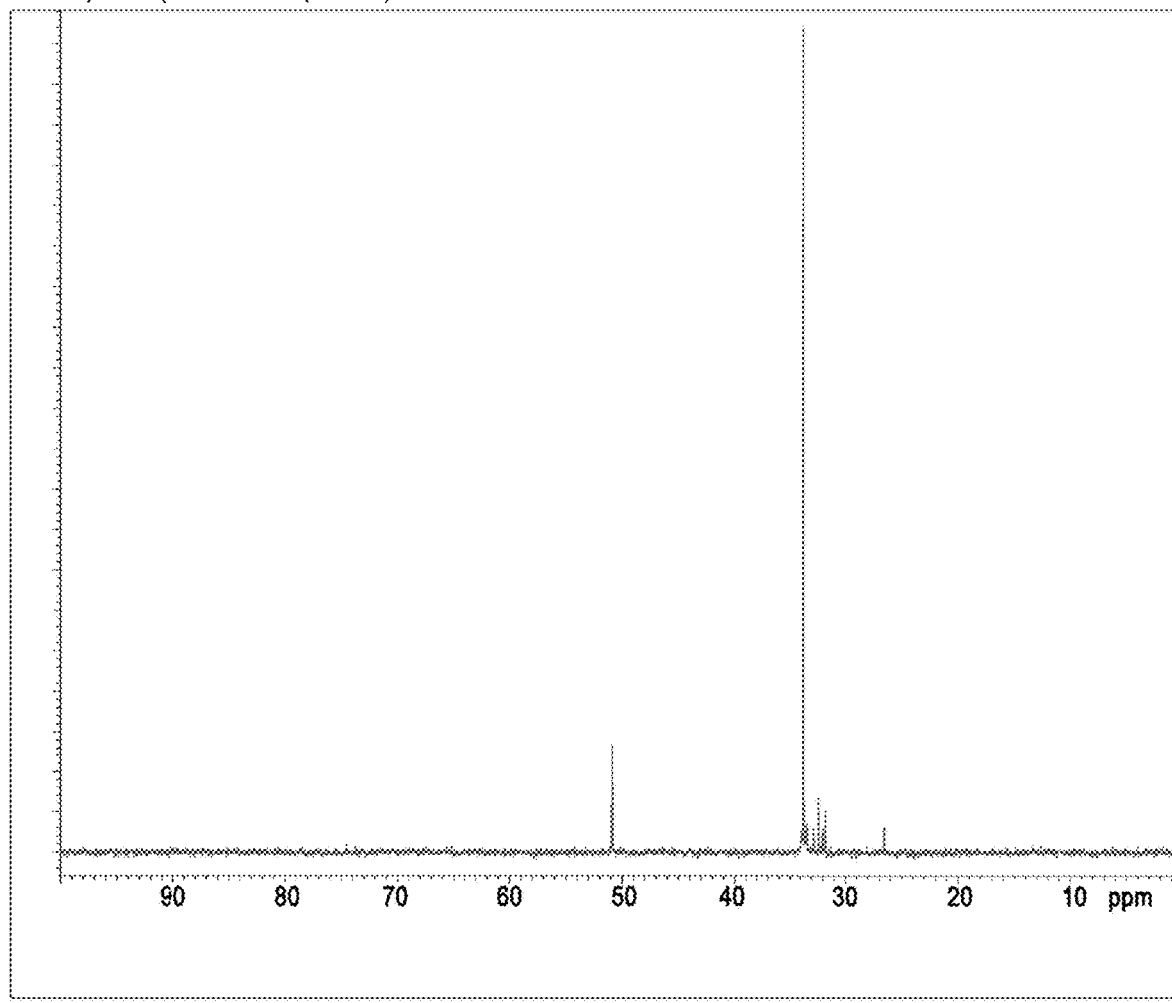
[Fig. 8-2]
C: Phosphorus (Chemical compound 8)

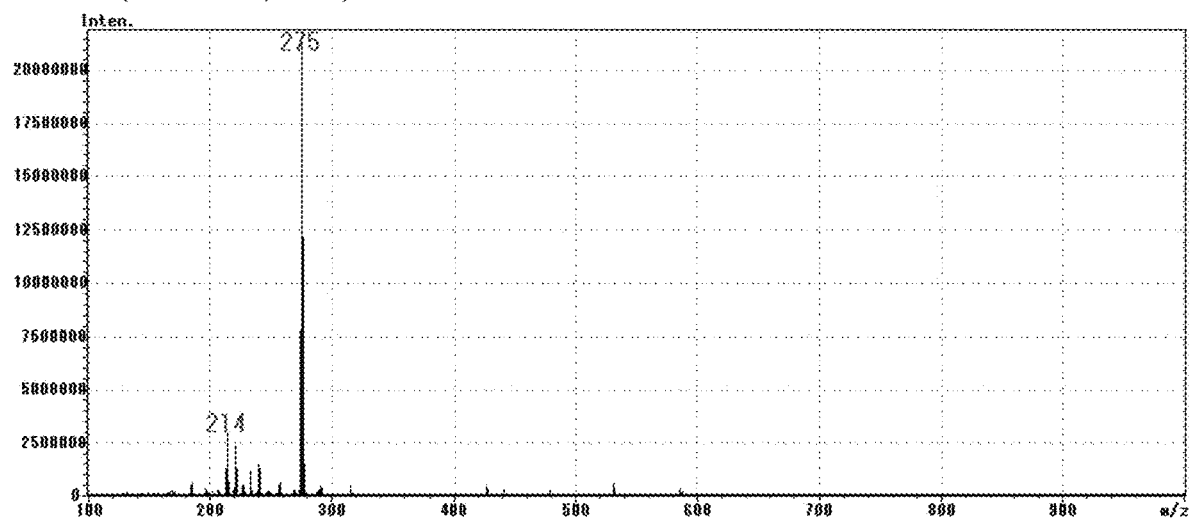
[Fig. 8-2]
D: ESI-MS (Chemical compound 8)

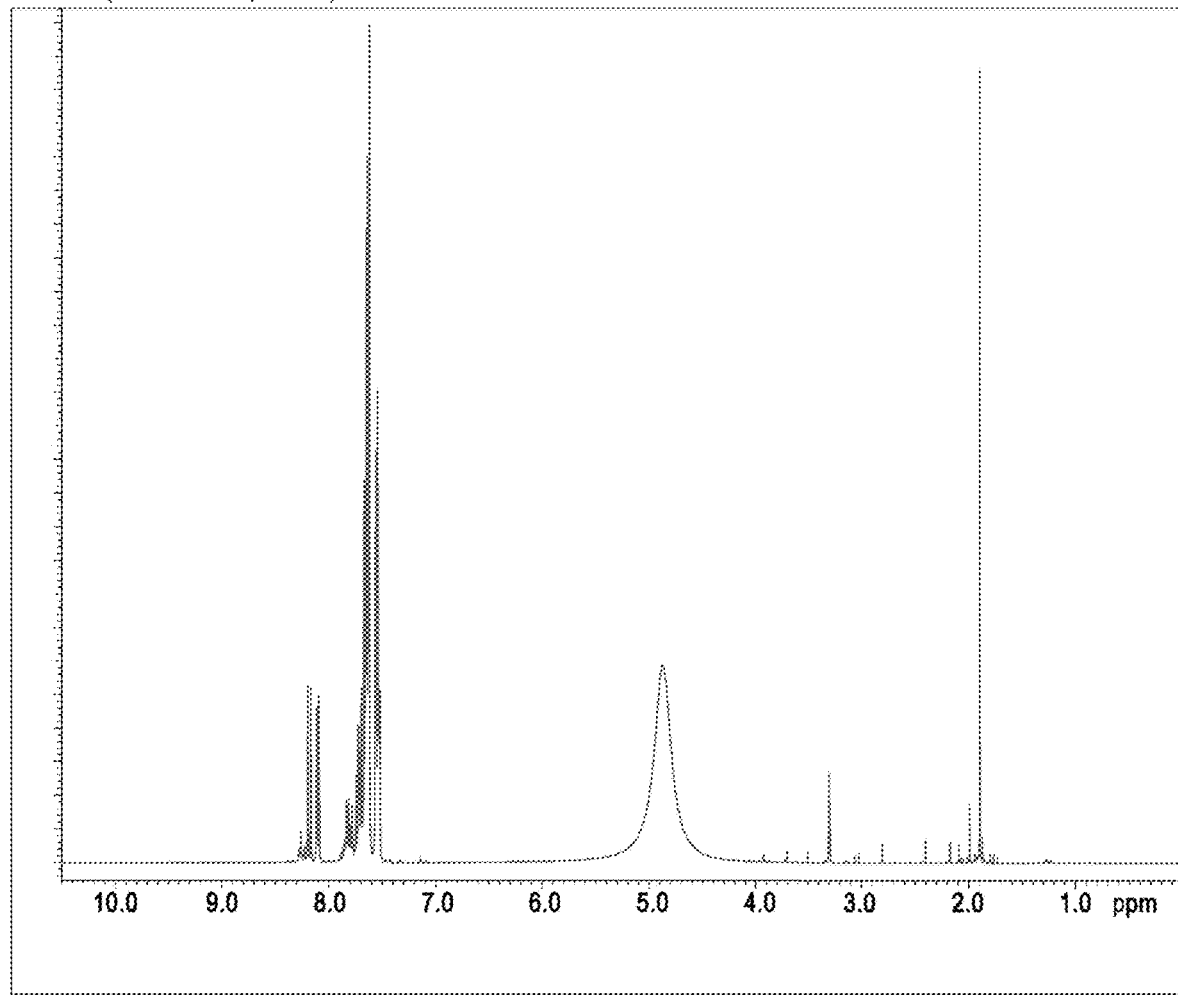

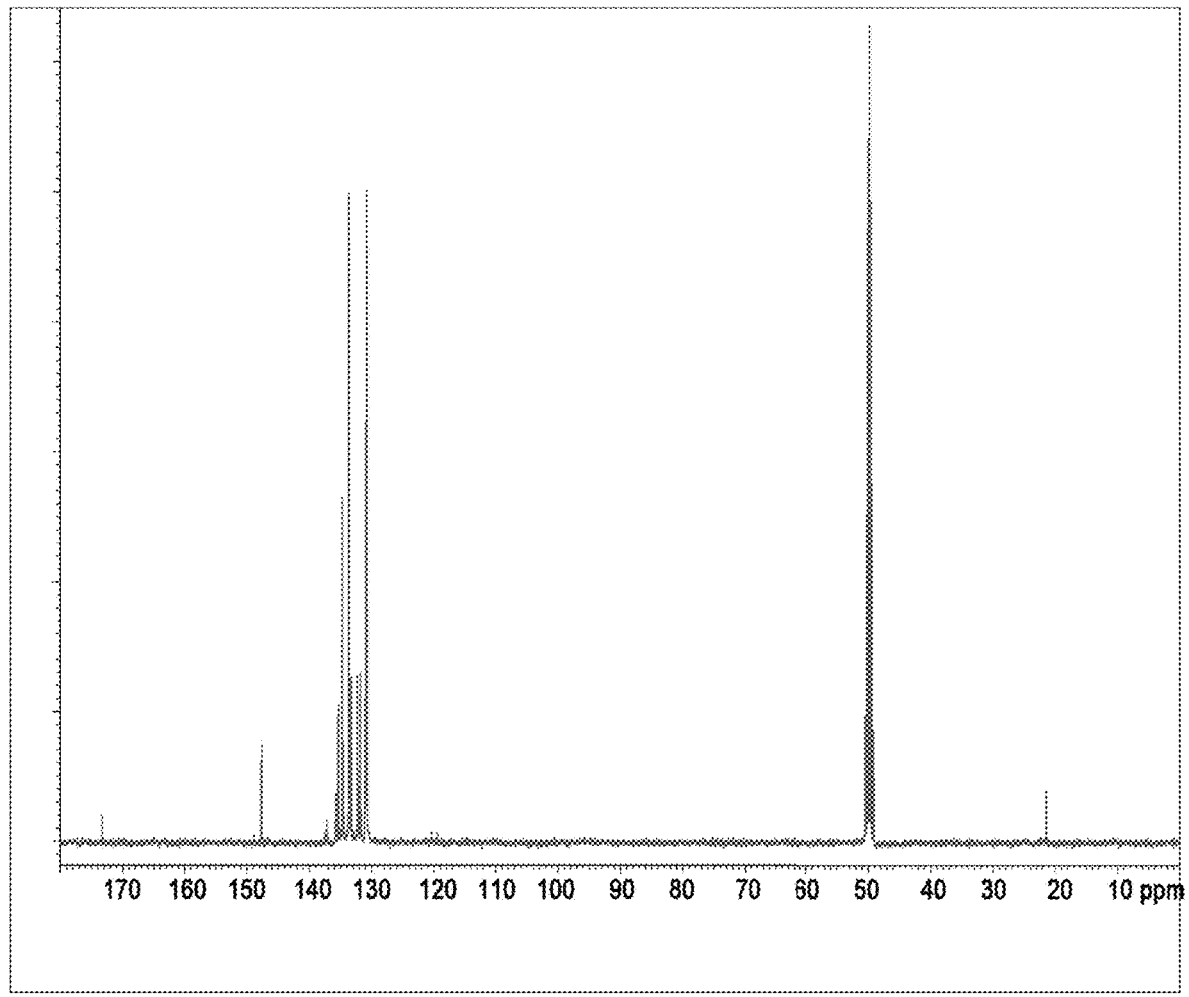
[Fig. 9-1]
B: Carbon (Chemical compound 9)

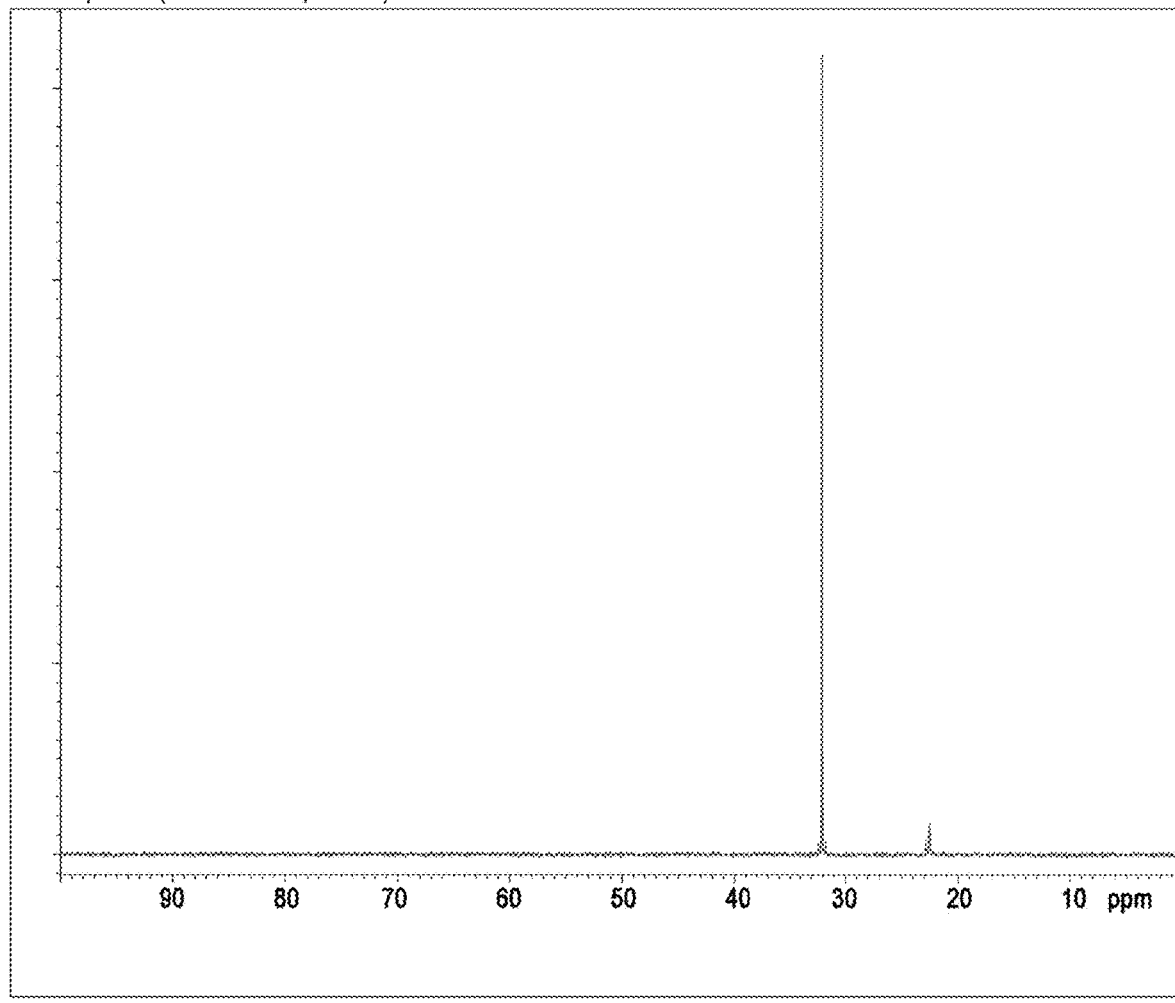

[Fig. 9-2]
D: ESI-MS (Chemical compound 9)
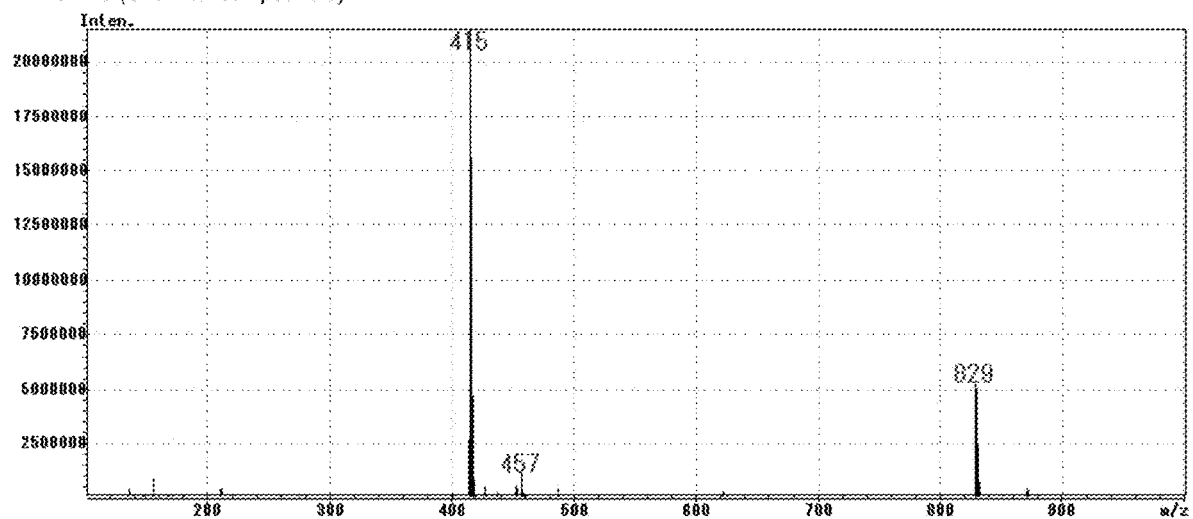

[Fig. 10]
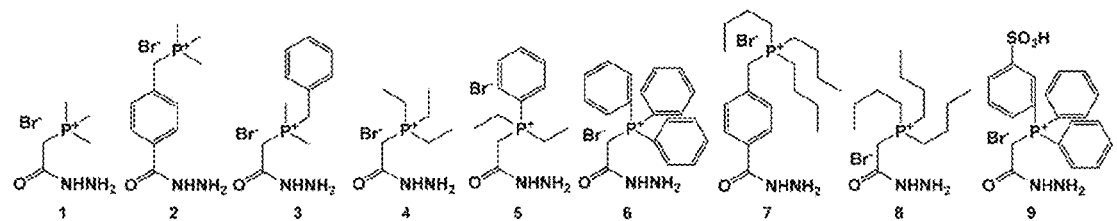
[Fig. 11]
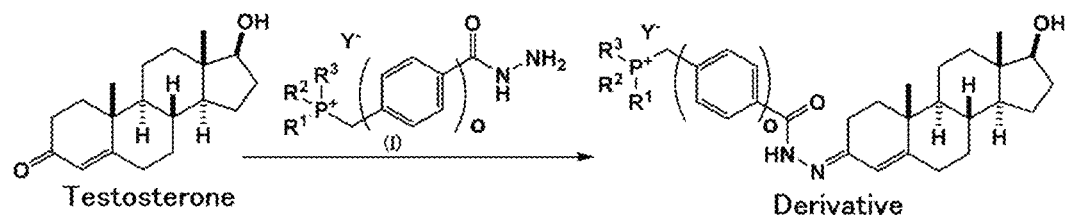
[Fig. 12]
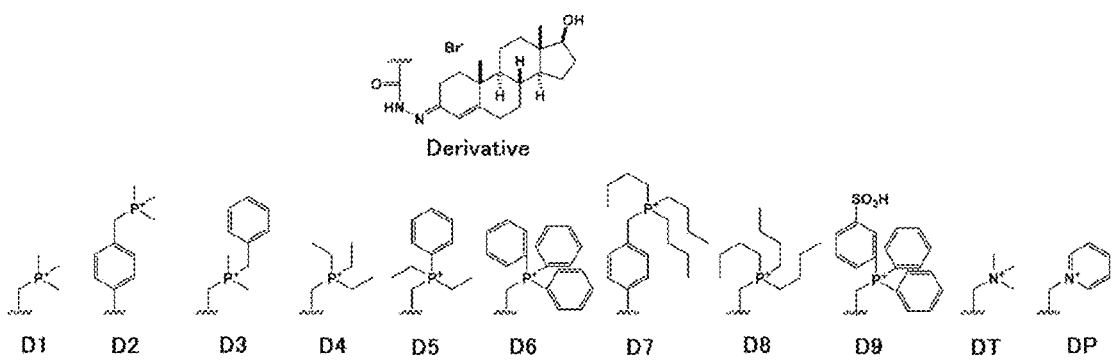

[Fig. 13]
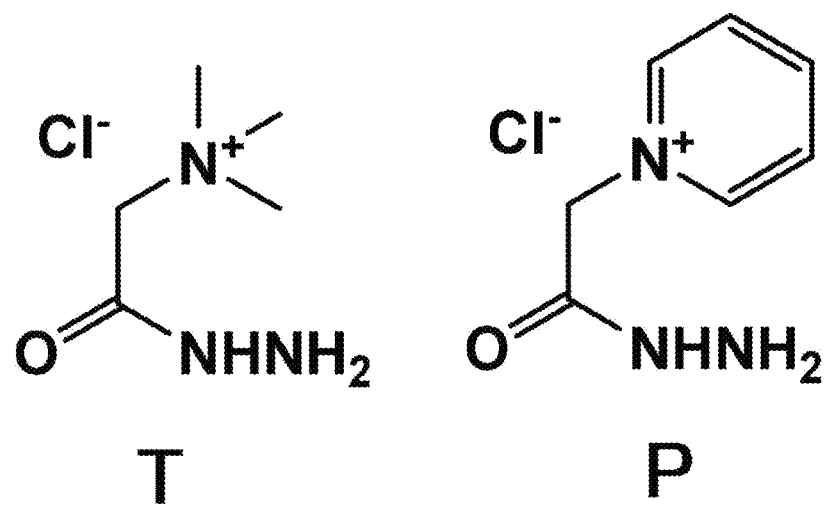

[Fig. 14-1]
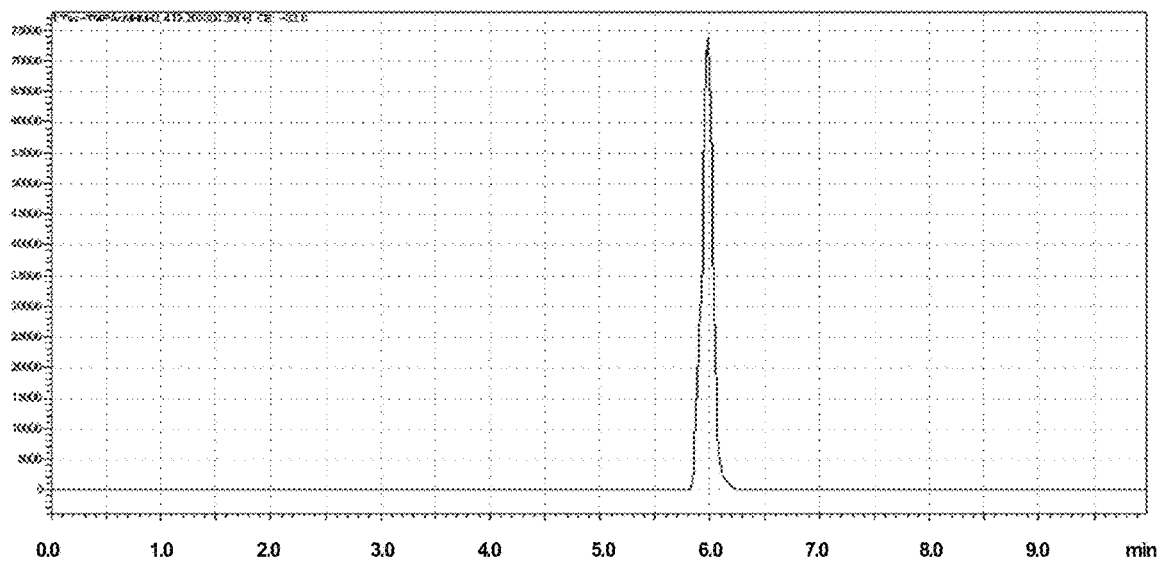
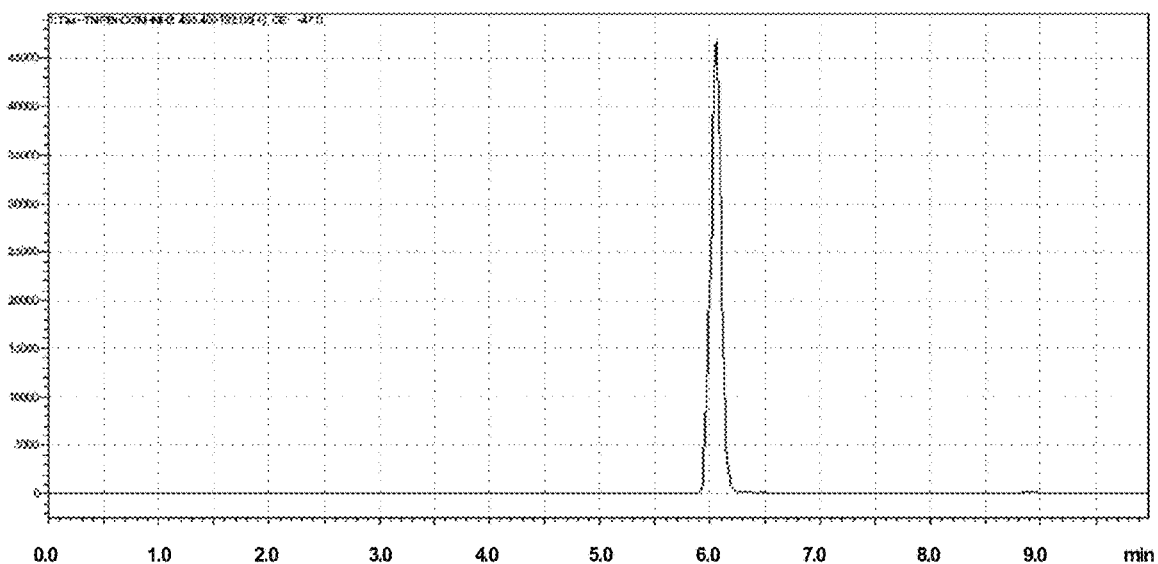

[Fig. 14-2]
C: D3
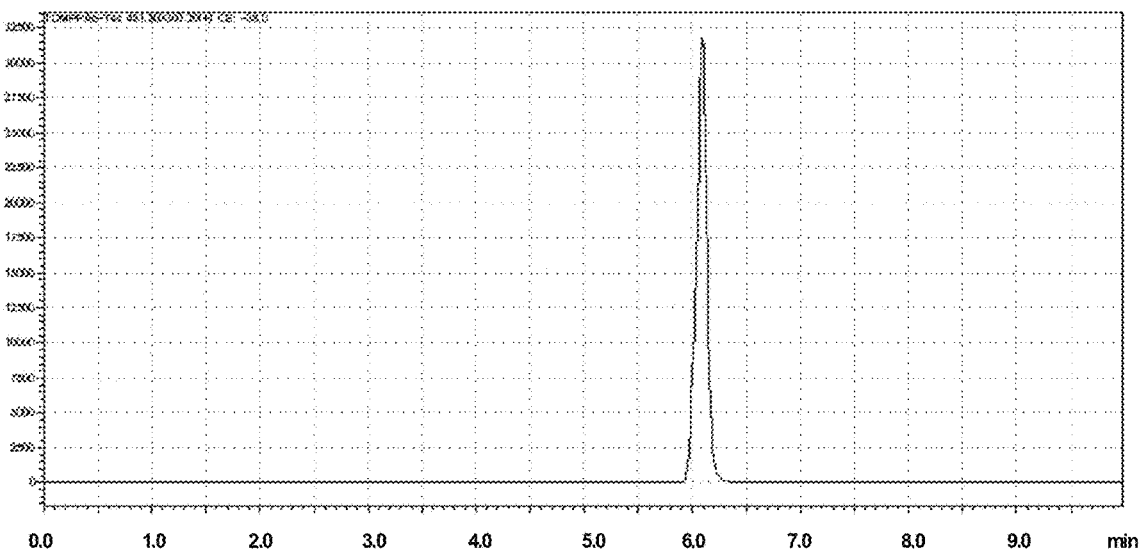
D: D4
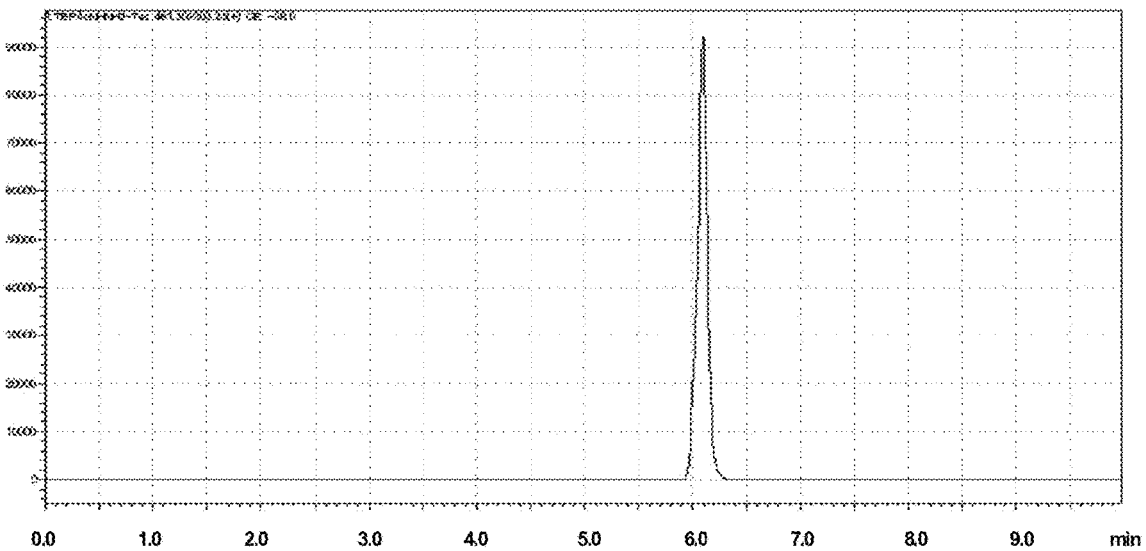

[Fig. 14-3]
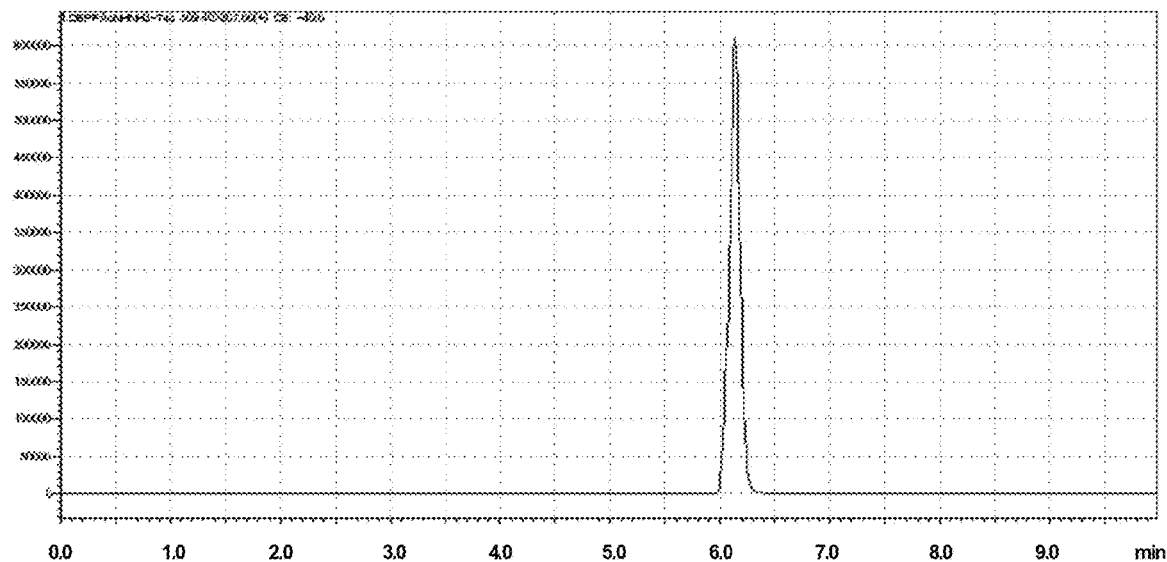
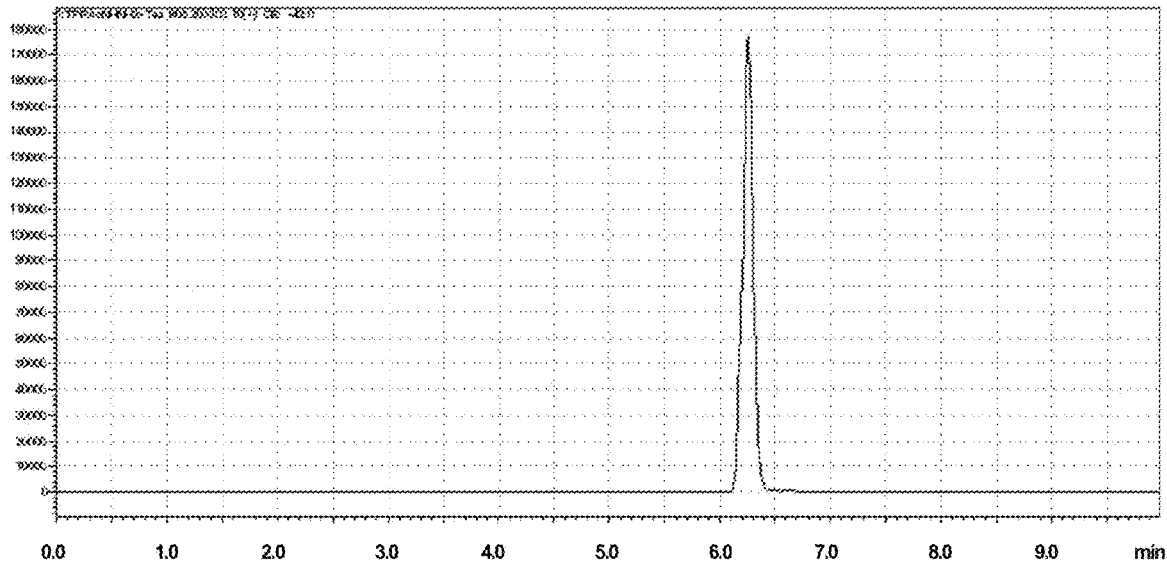

[Fig. 14-4]
G: D7
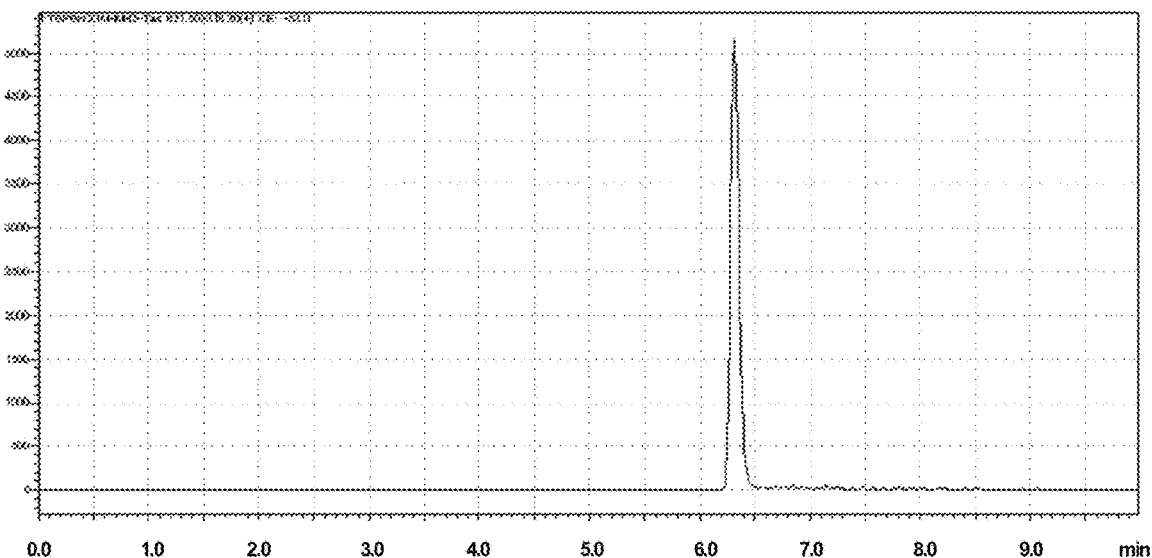
H: D8
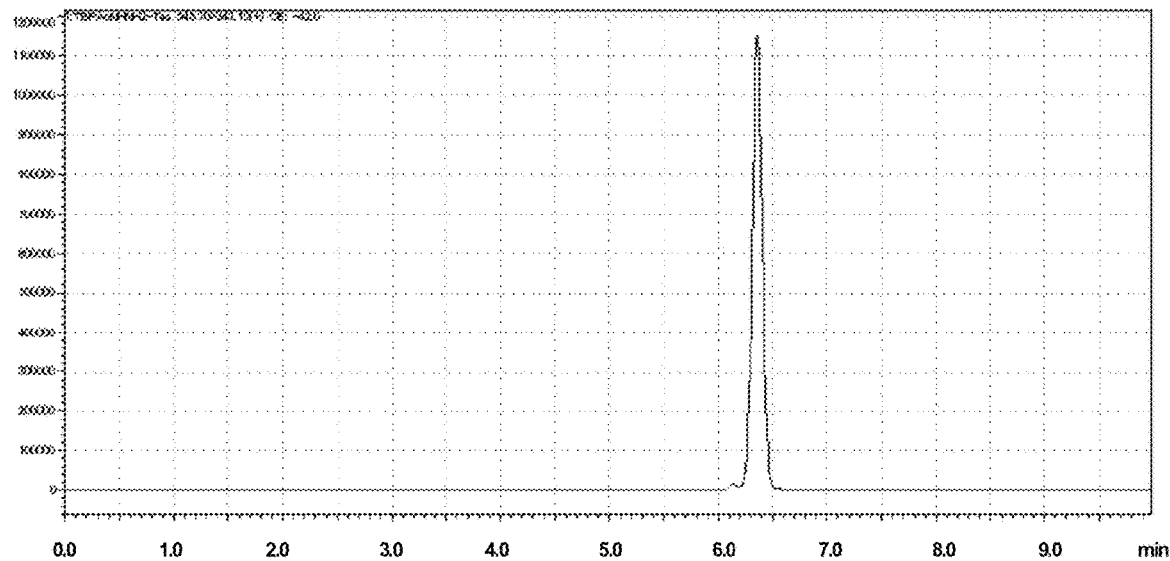

[Fig. 14-5]
I: D9
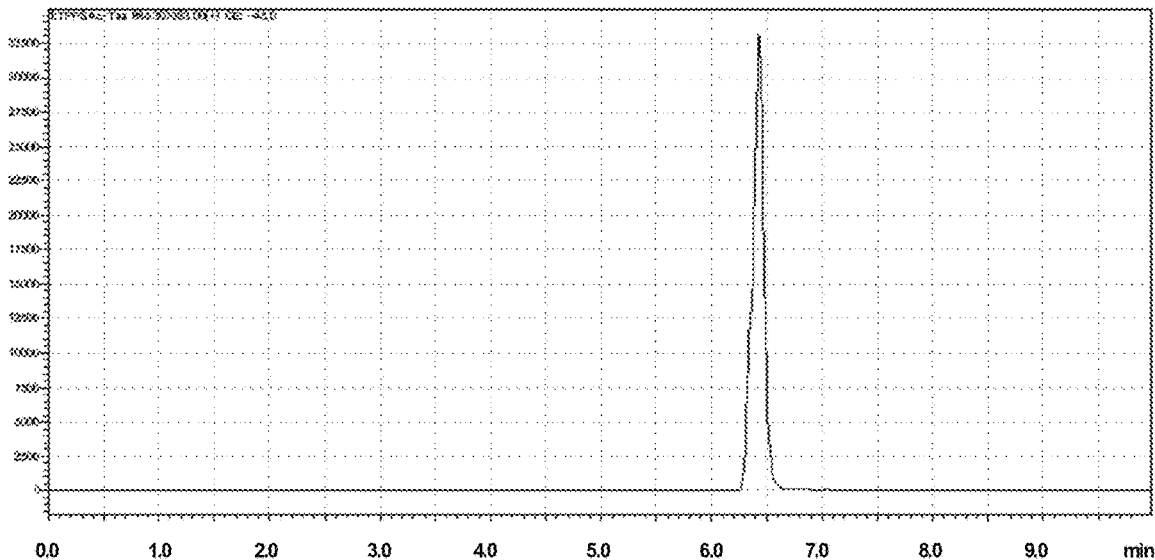
J: DT
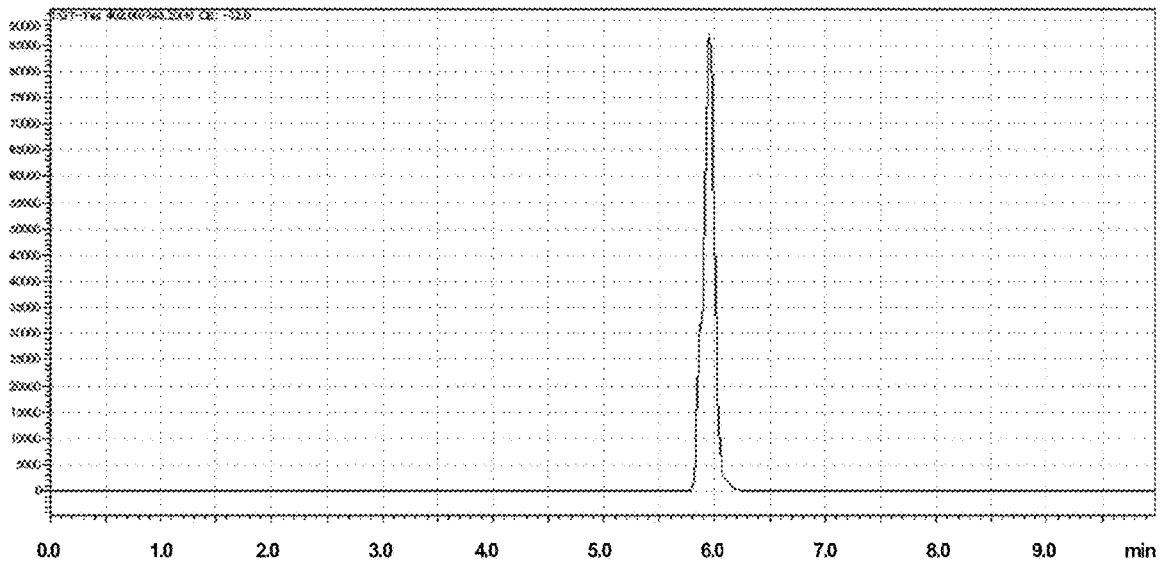

[Fig. 14-6]
K: DP
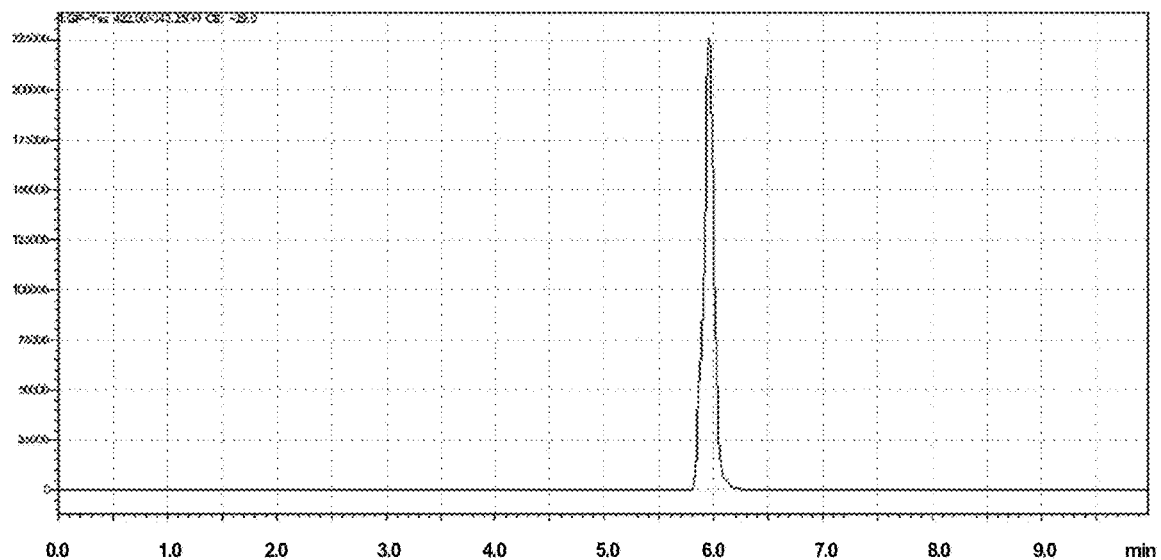
L: Not Derivatized
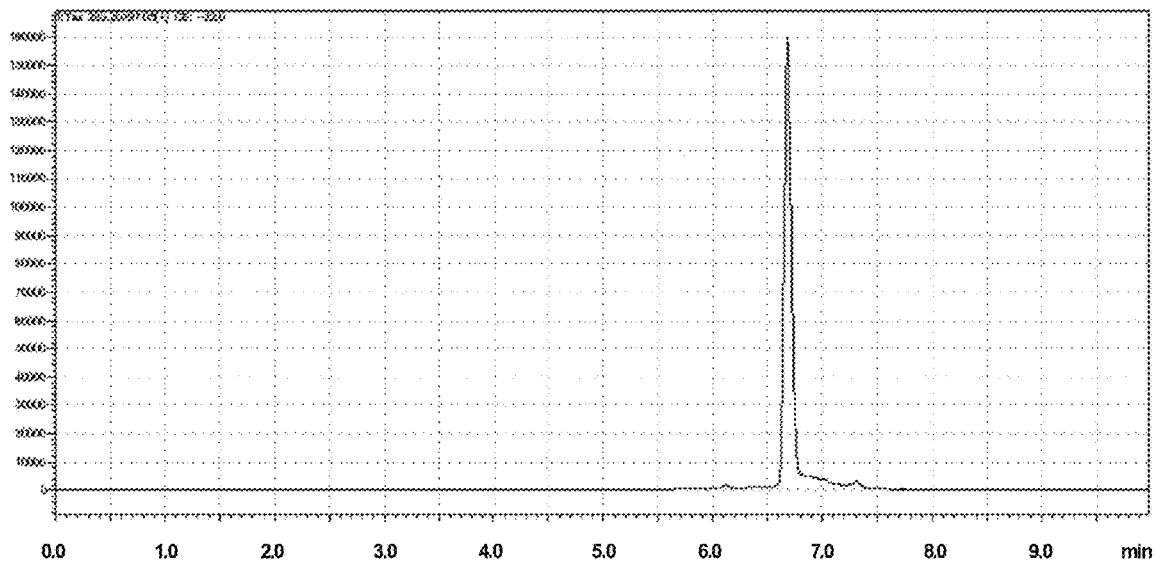

[Fig. 15-1]
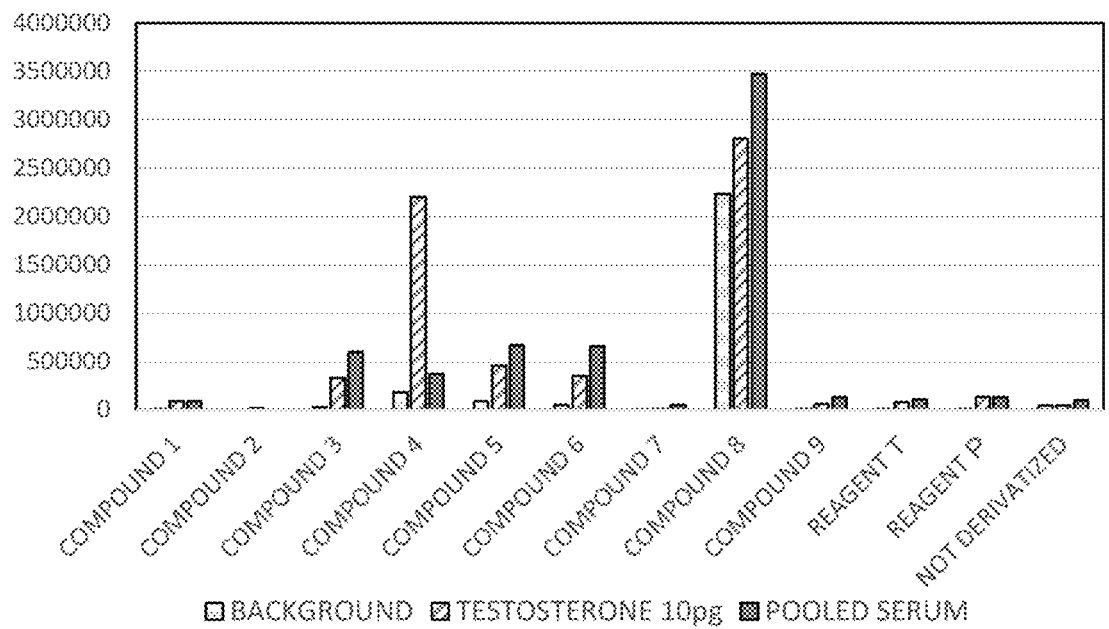
[Fig. 15-2]
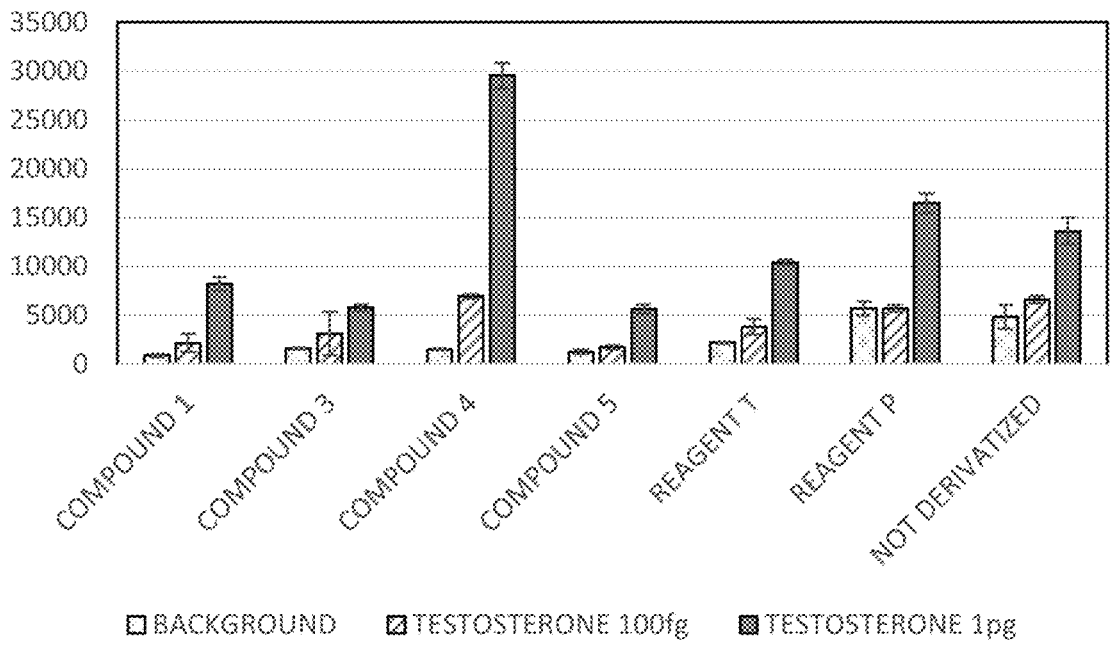

[Fig. 16]
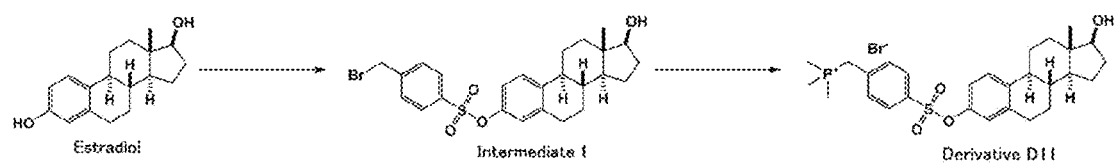

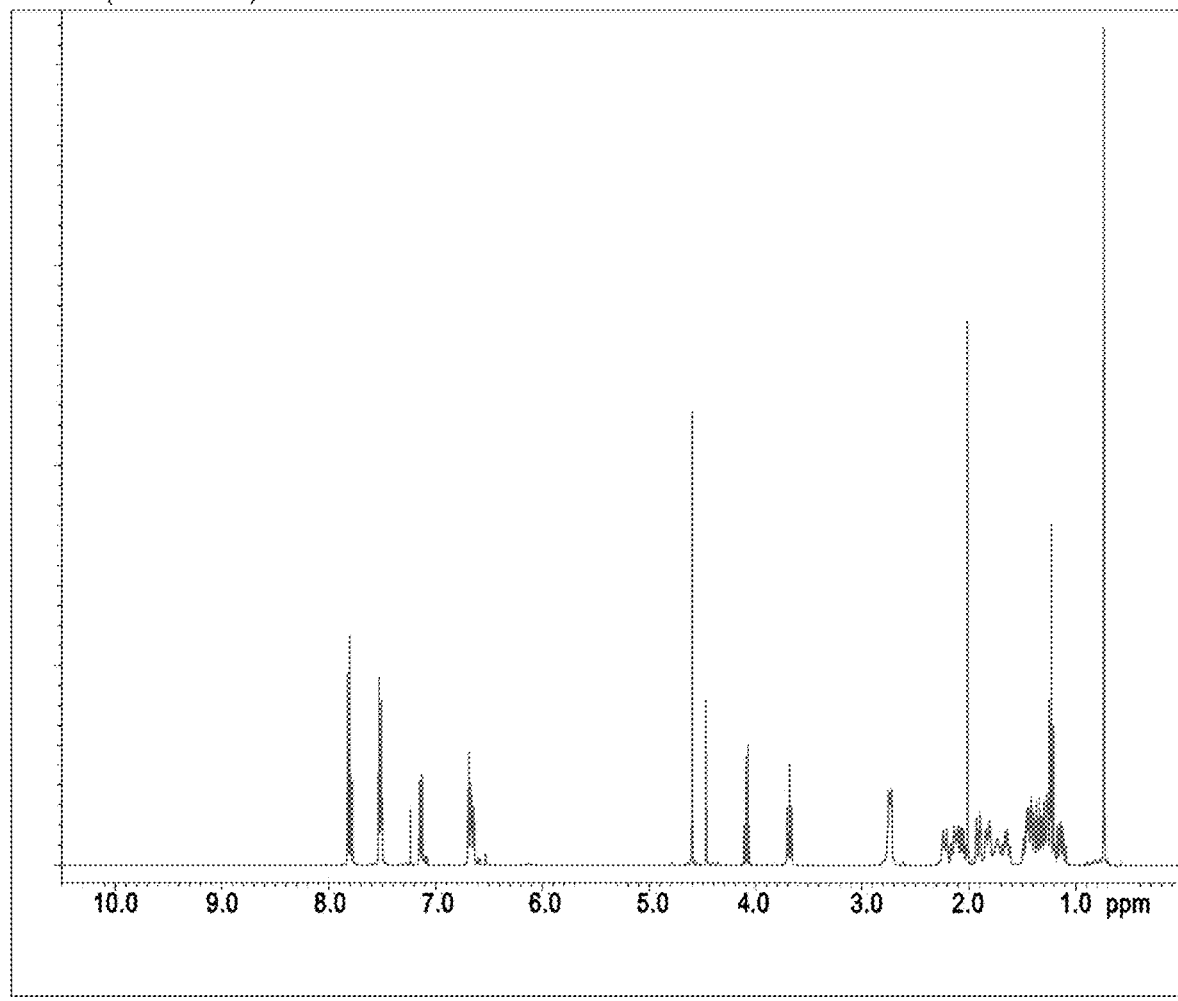
[Fig. 17]
A: Proton (Intermediate 1)

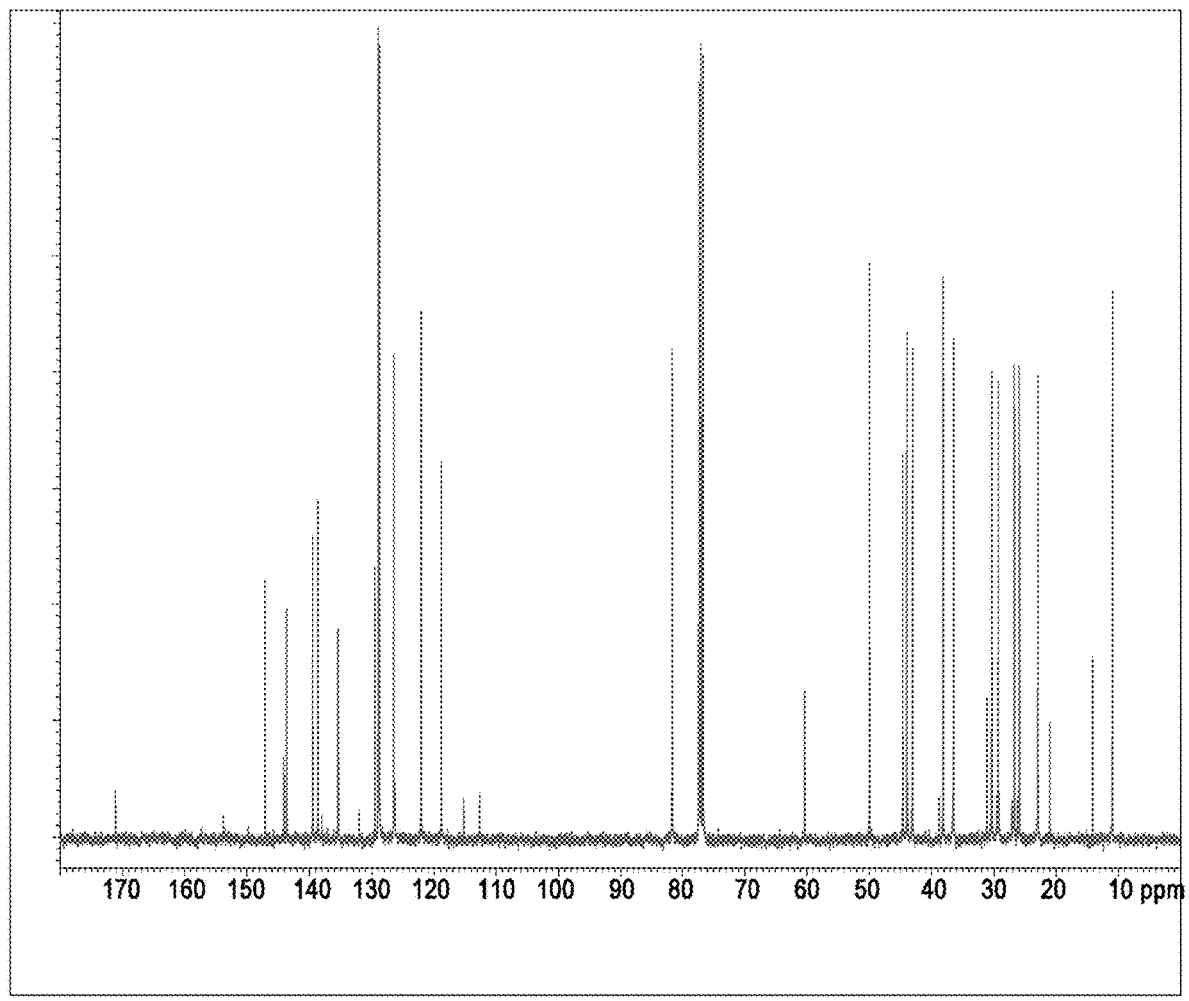
[Fig. 17]
B: Carbon (Intermediate 1)

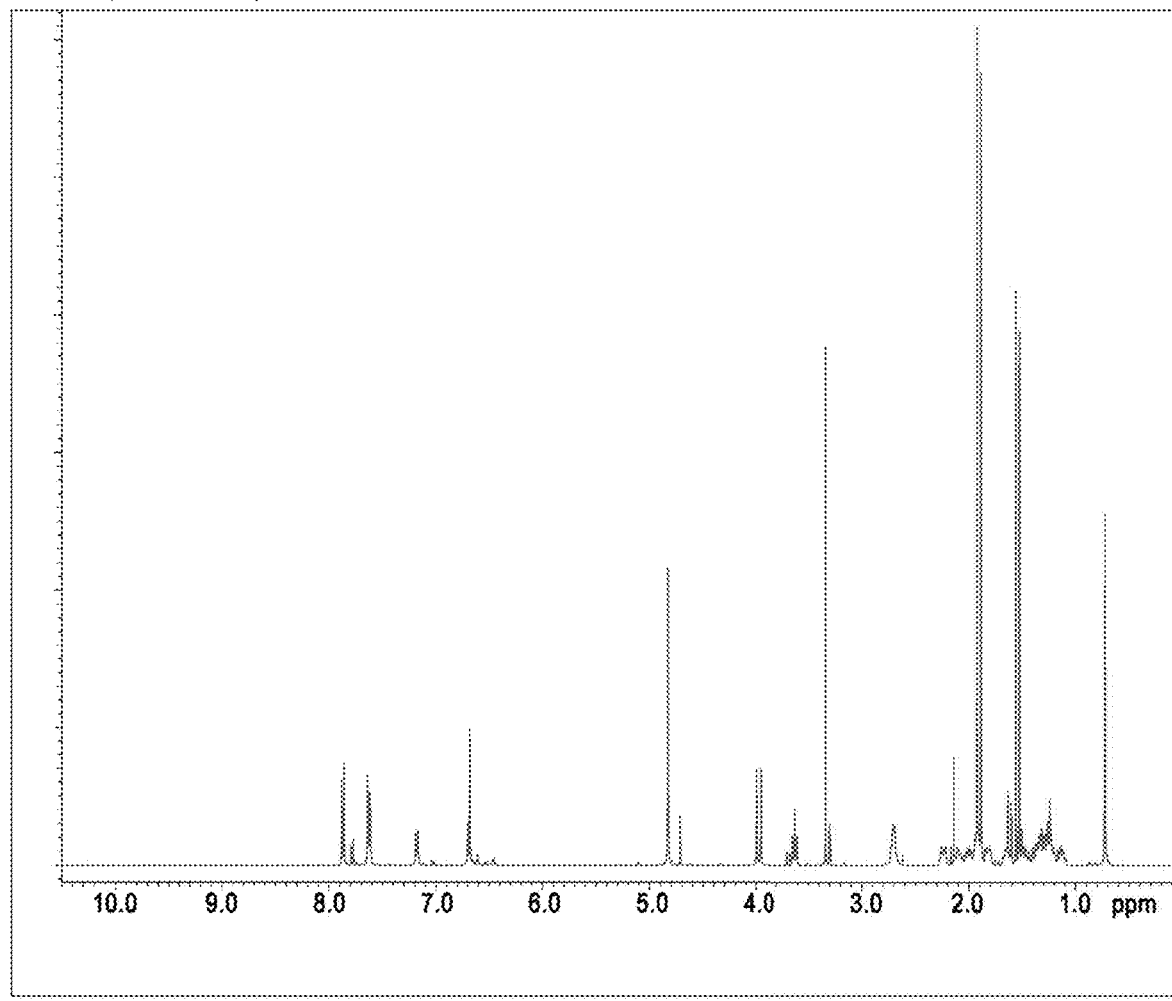
[Fig. 18-1]
A: Proton (Derivative D11)

[Fig. 18-1]
B: Carbon (Derivative D11)
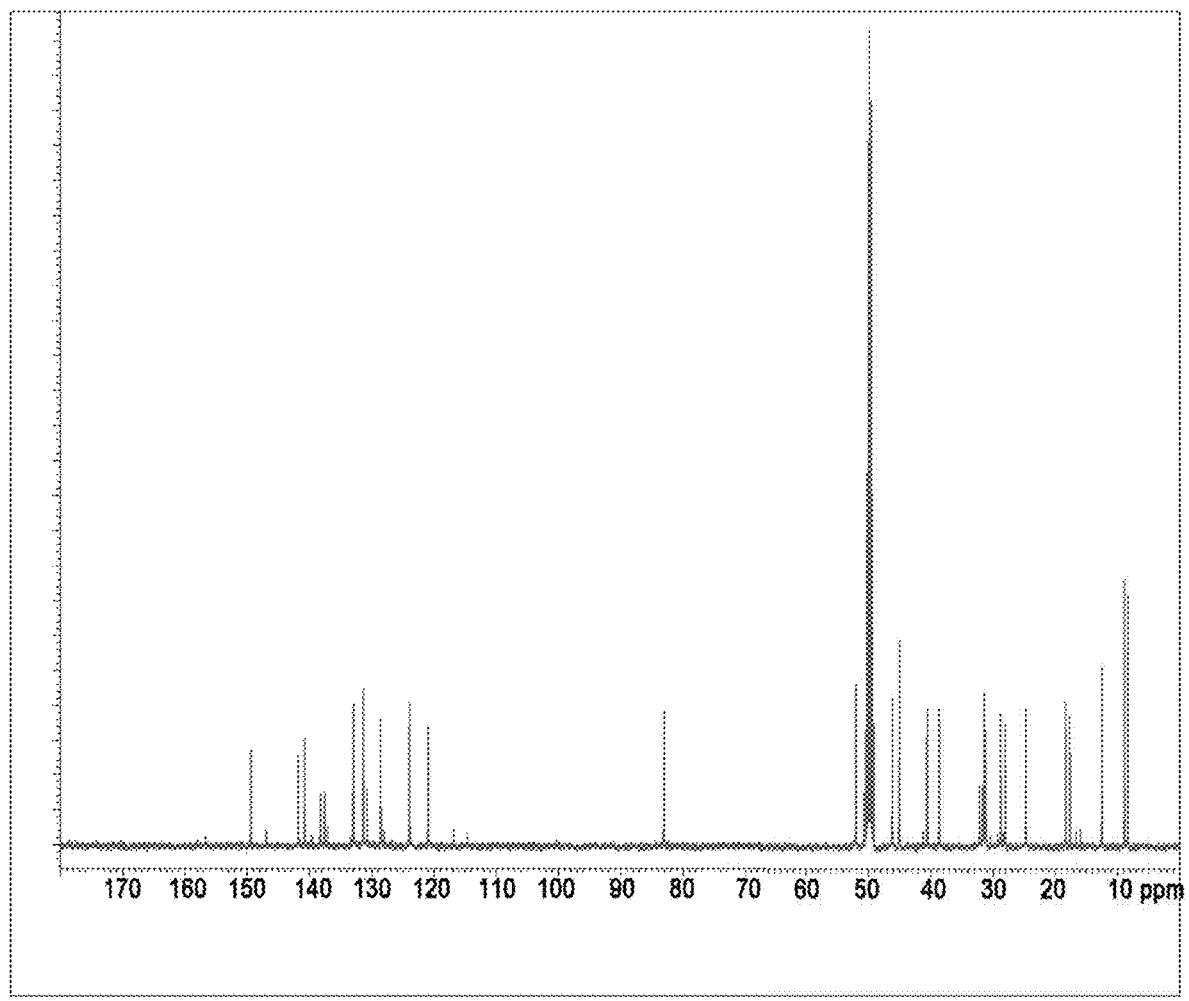

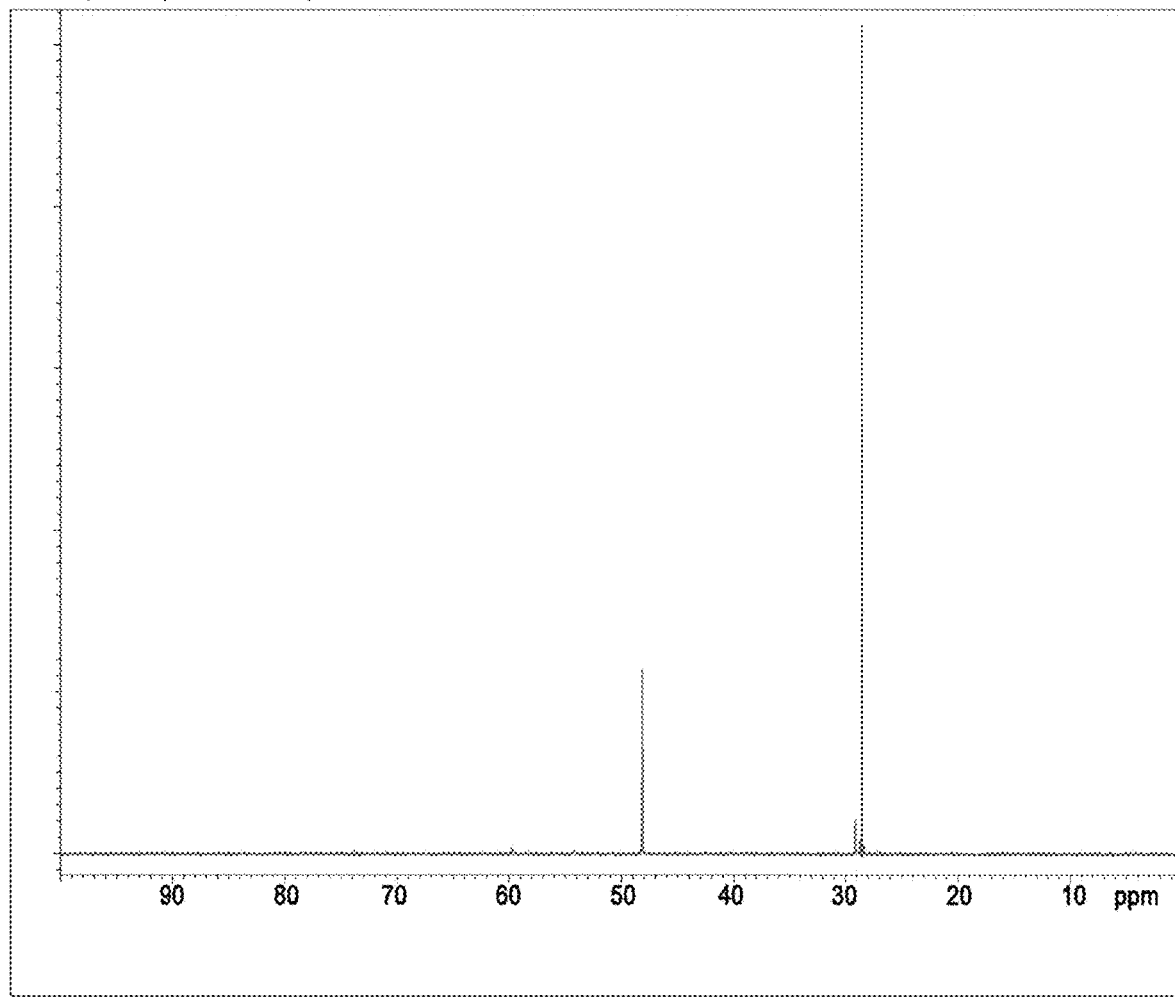

[Fig. 18-2]
D: ESI-MS (Derivative D11)
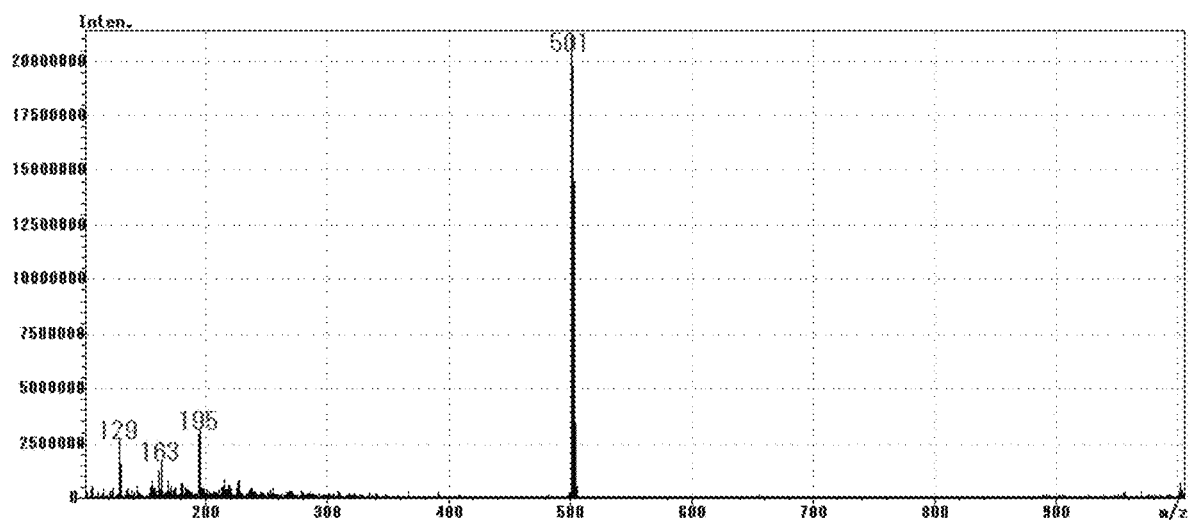

[Fig. 19]
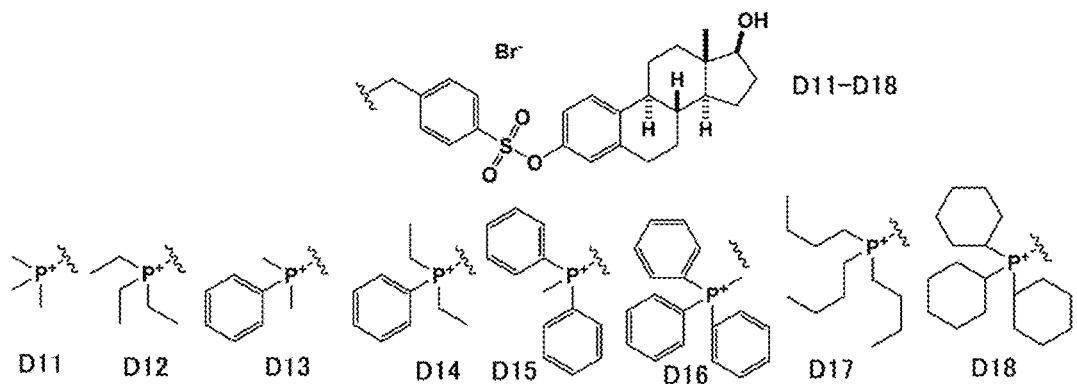
[Fig. 20]
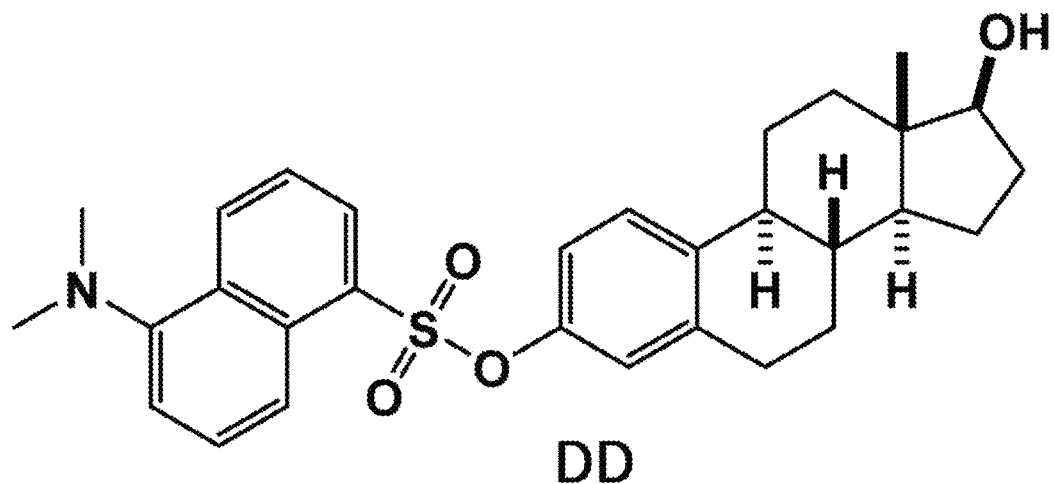
[Fig. 21]
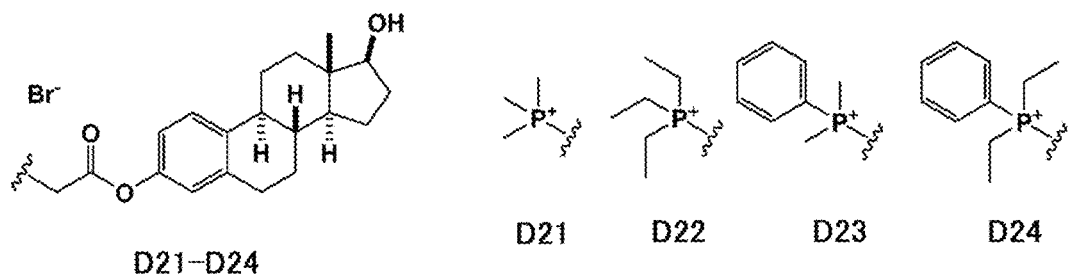

[Fig. 22-1]
A: D11
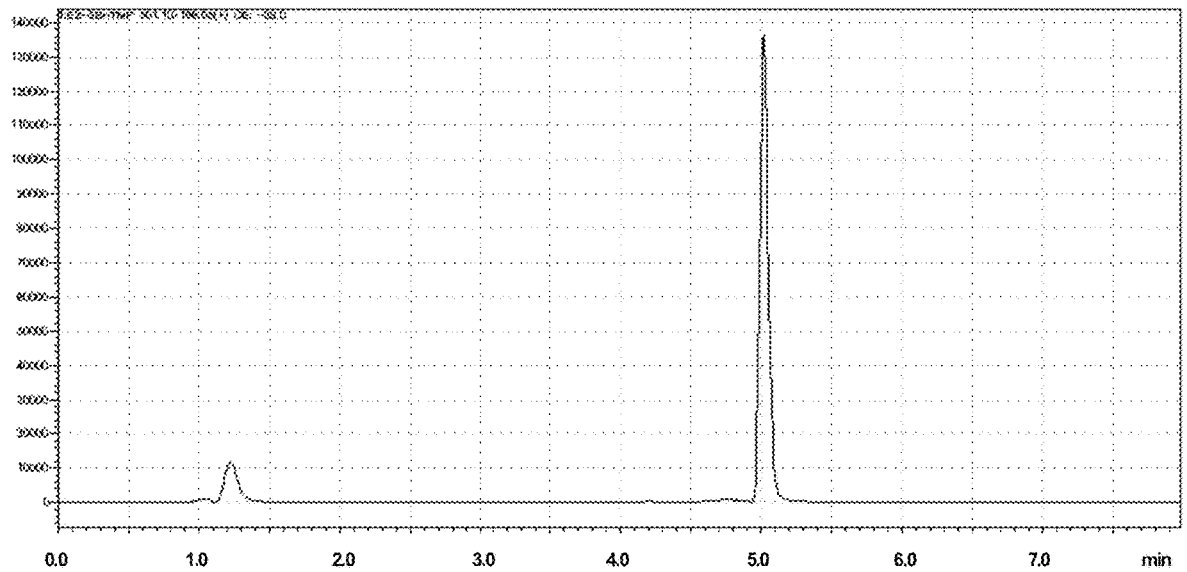
B: D12
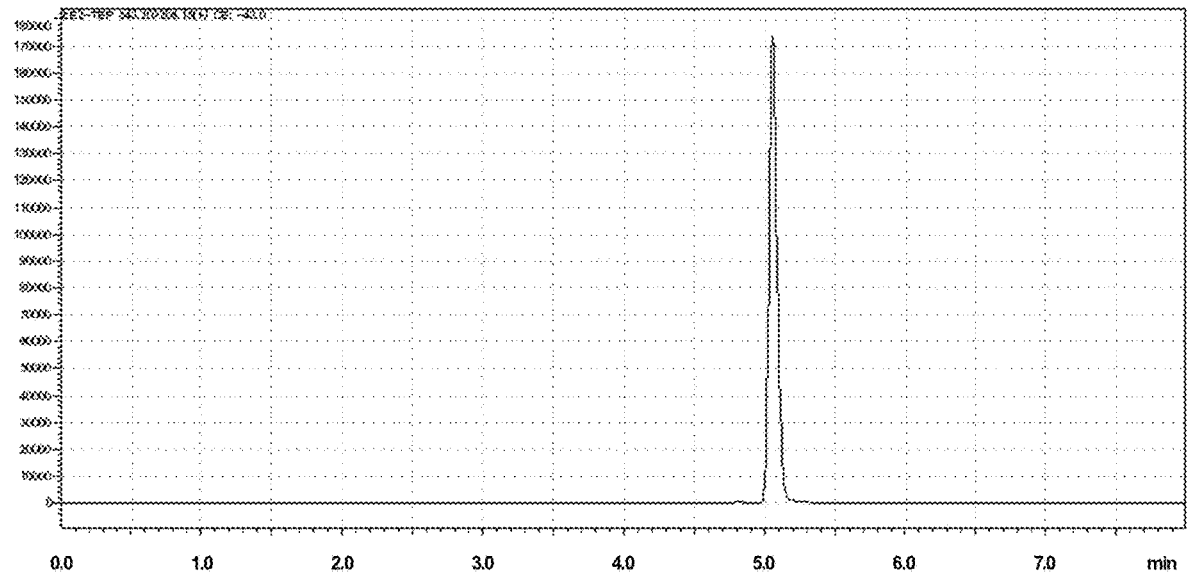

[Fig. 22-2]
C: D13
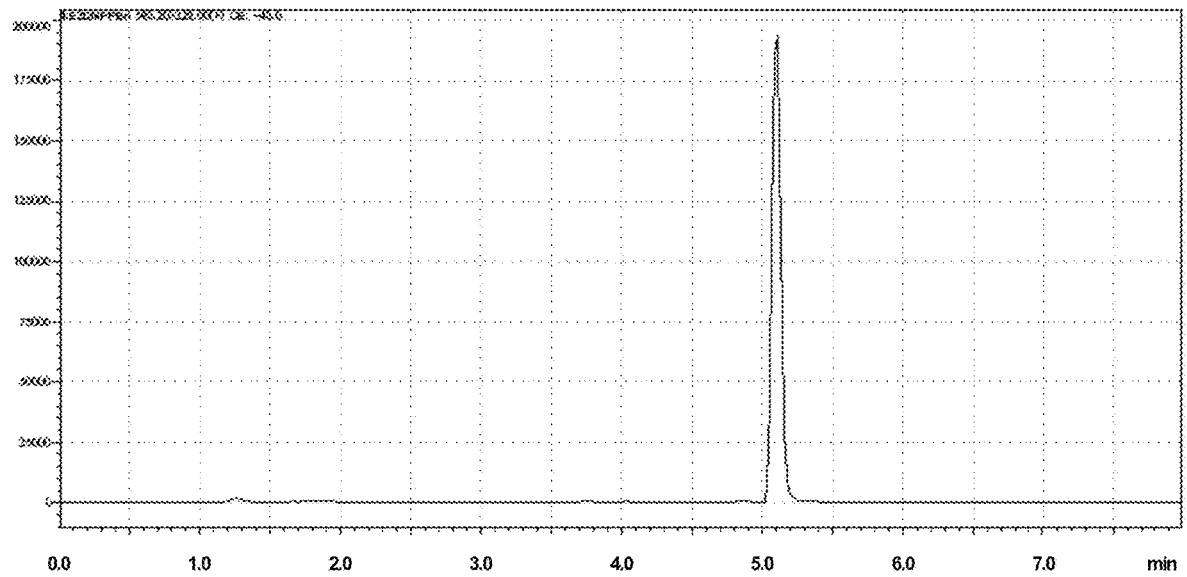
D: D14
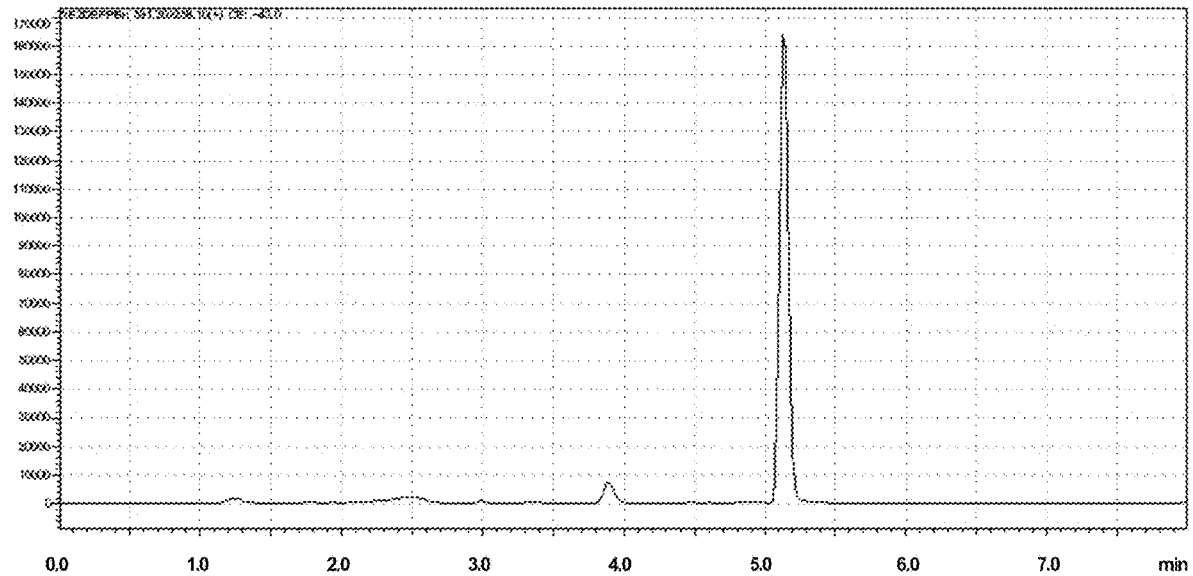

[Fig. 22-3]
E: D15
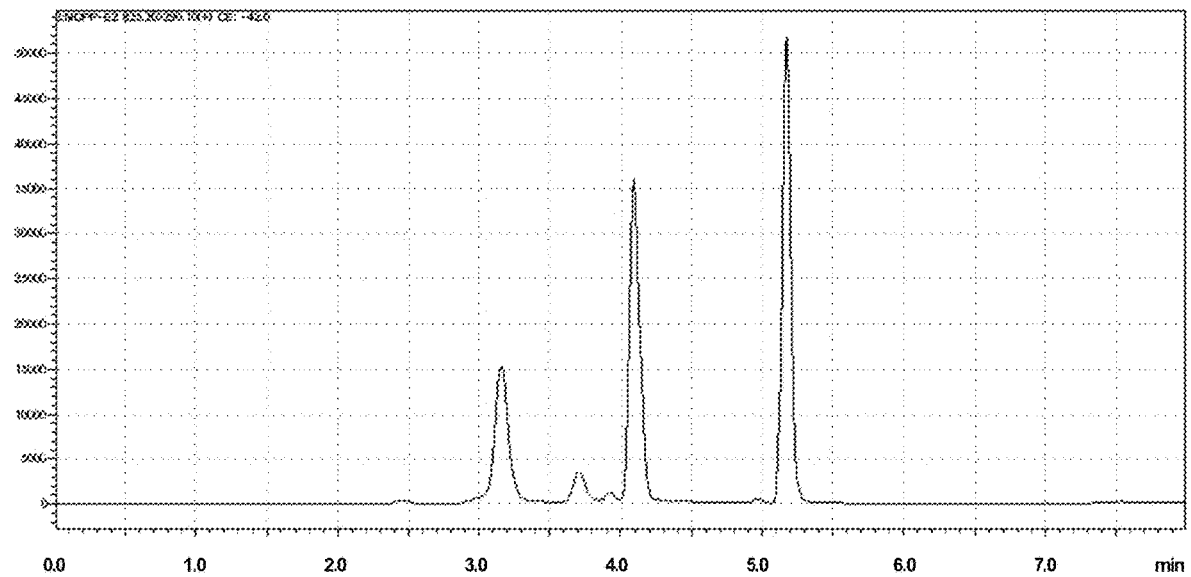
F: D16
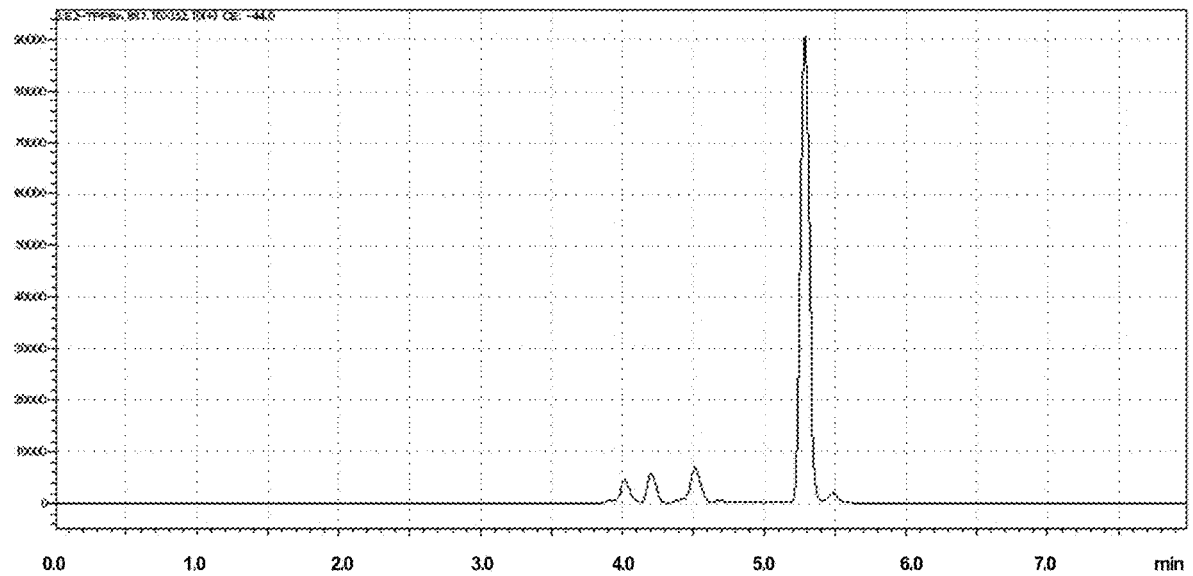

[Fig. 22-4]
G: D17
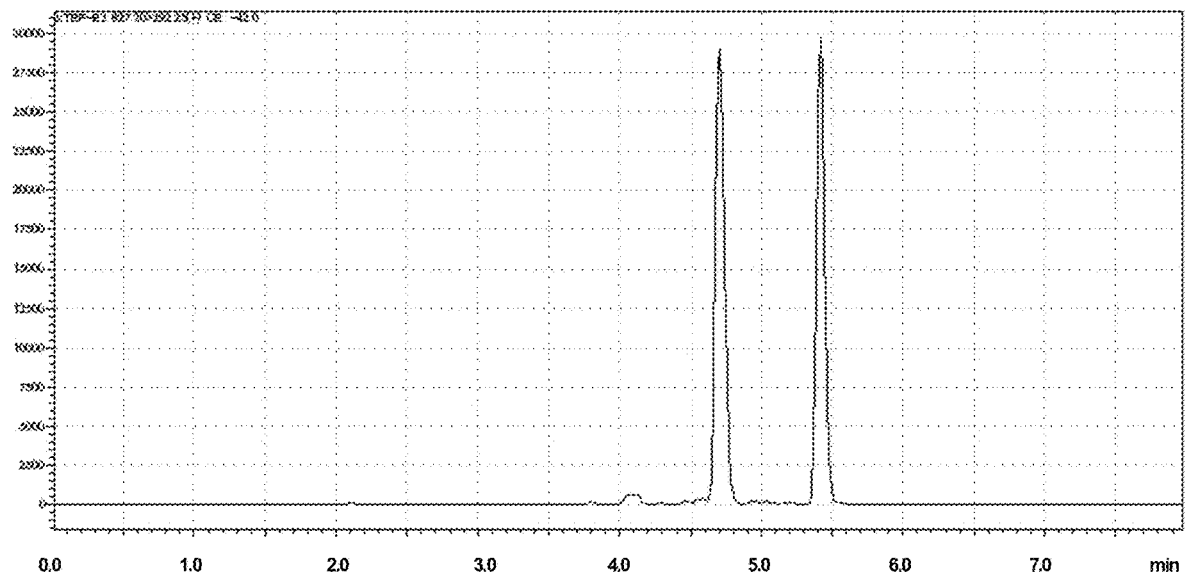
H: D18
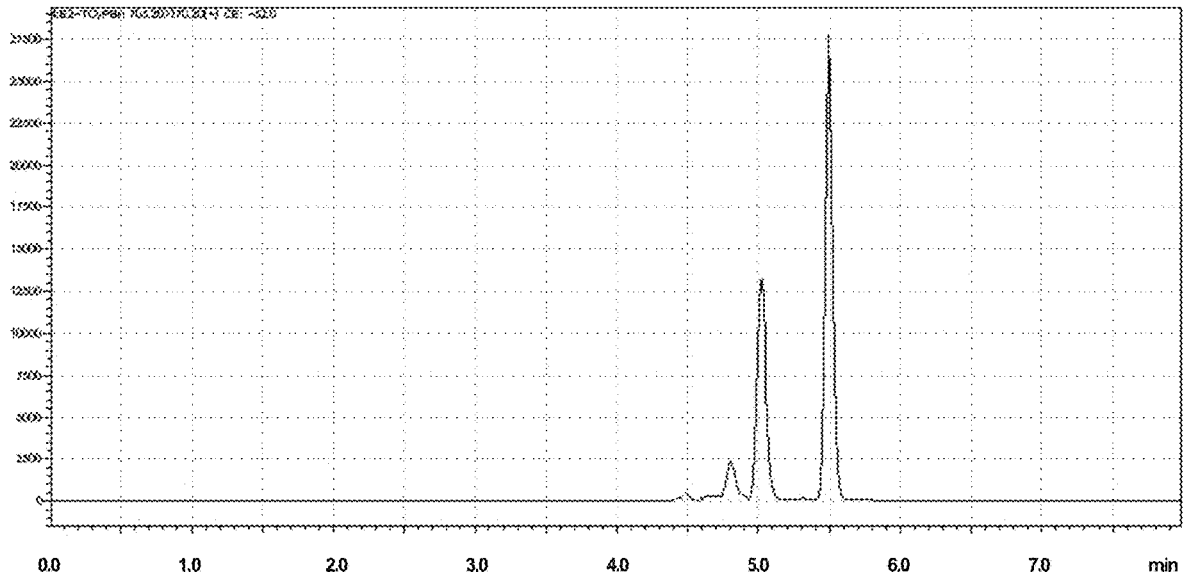

[Fig. 22-5]
I: DD
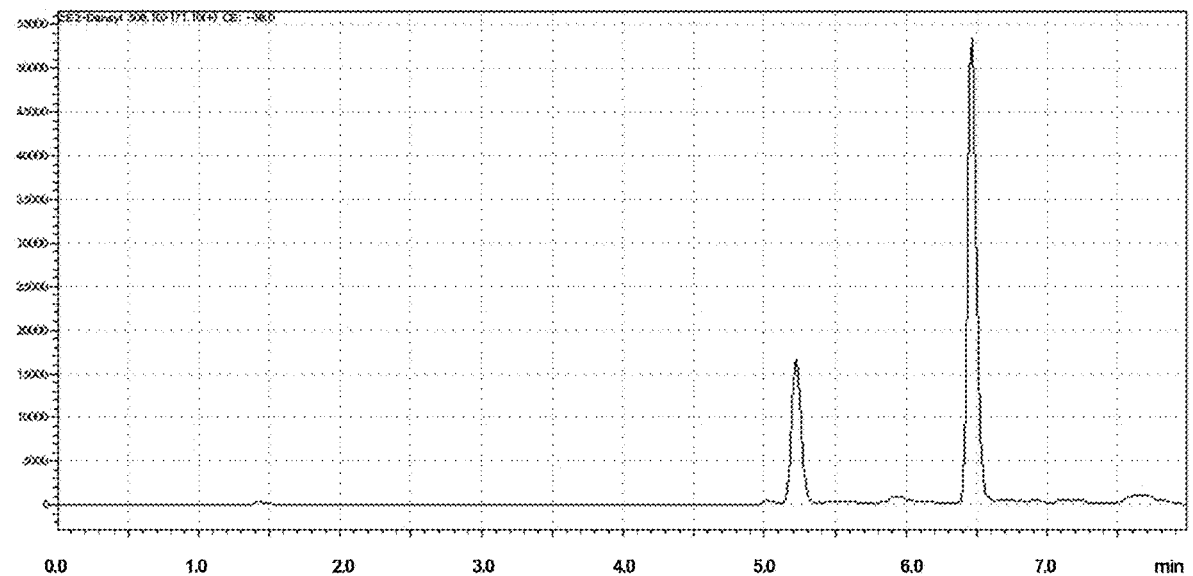
J: D21
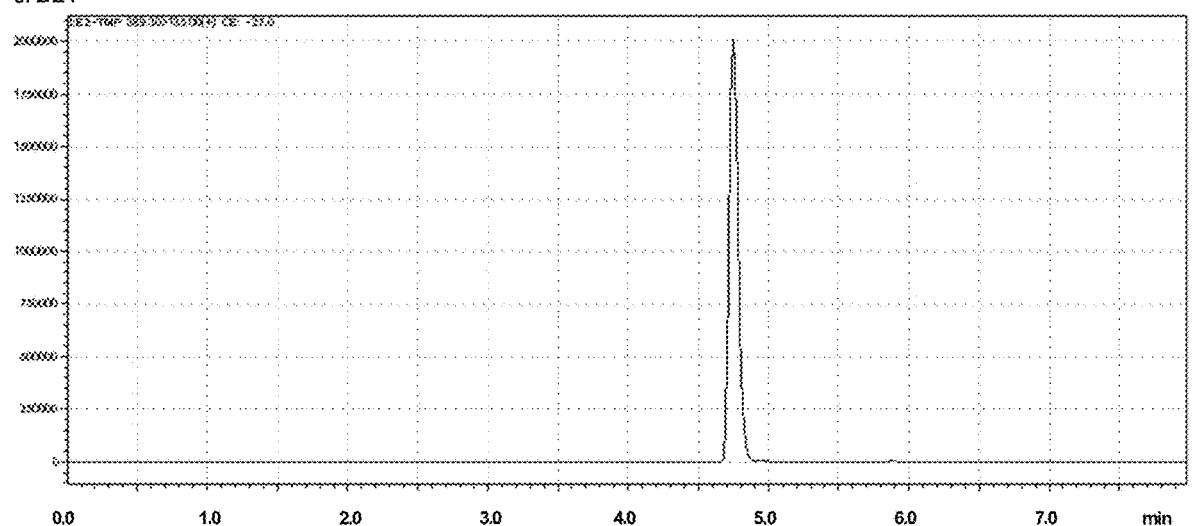

[Fig. 22-6]
K: D22
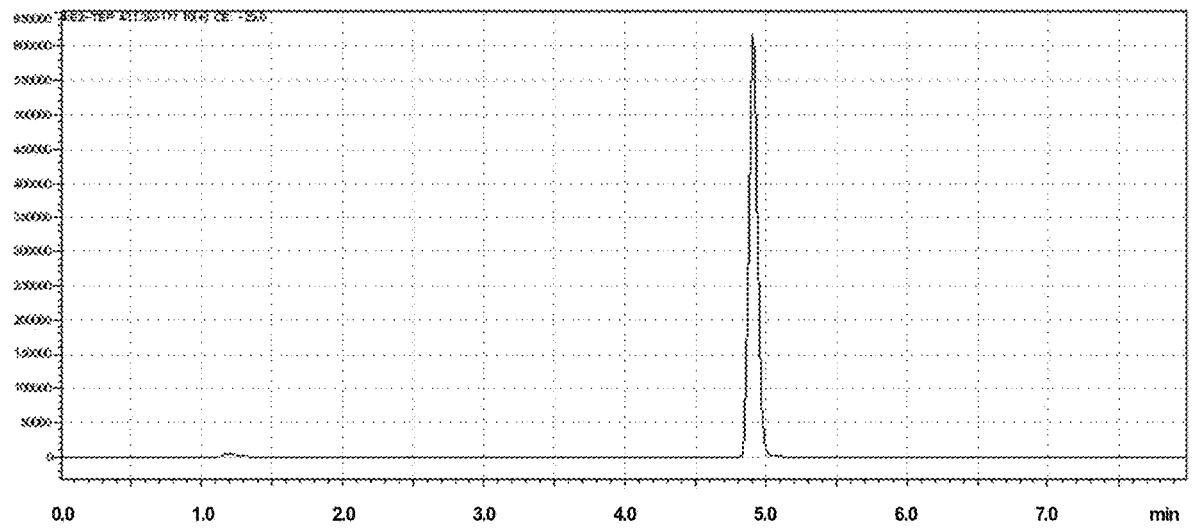
L: D23
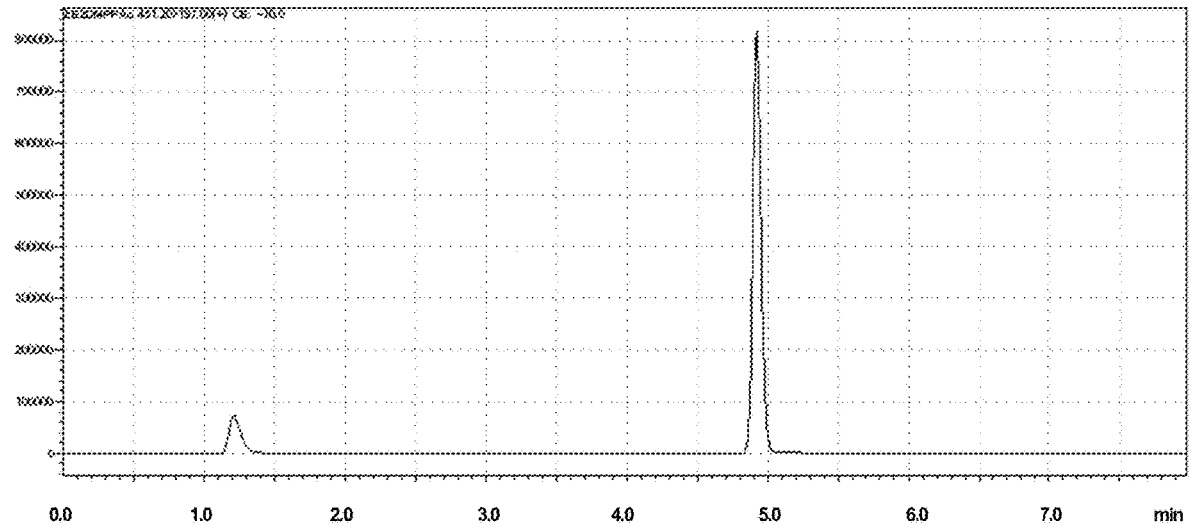

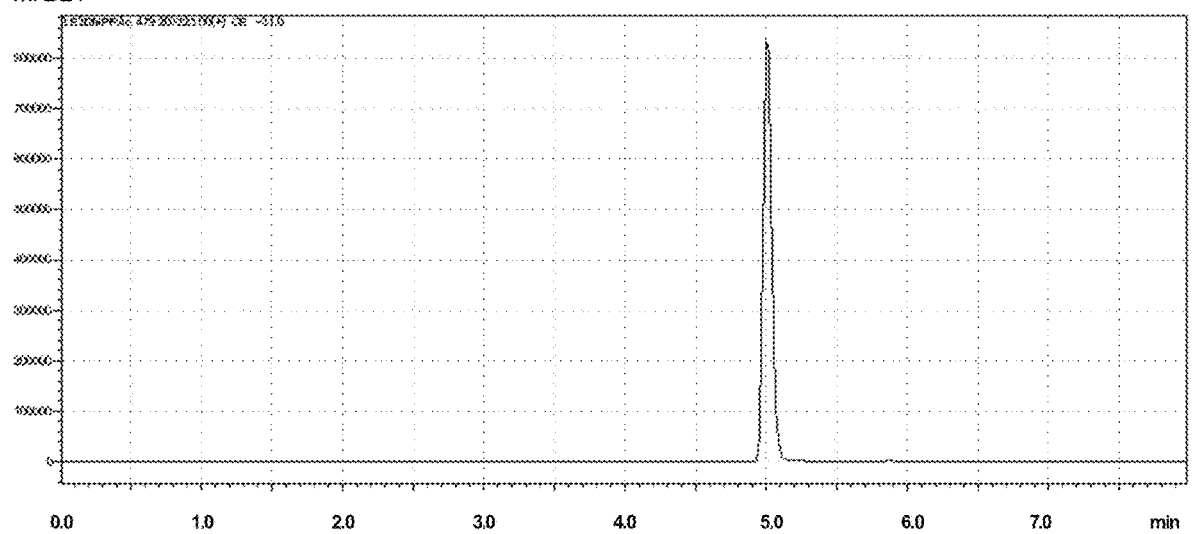
[Fig. 22-7]
M: D24

[Fig. 23]
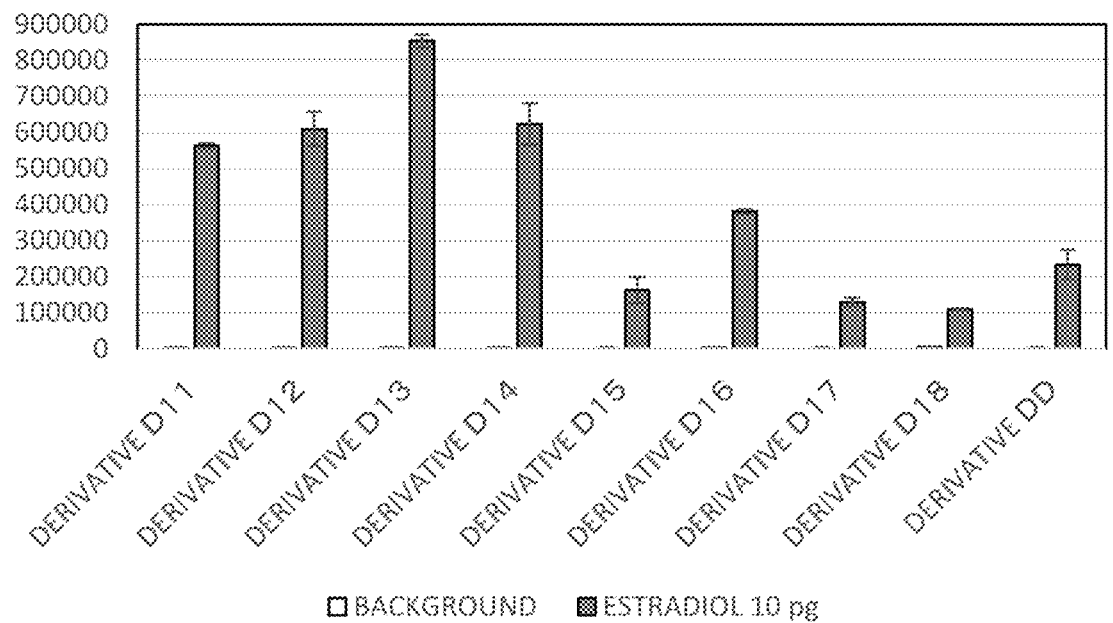
[Fig. 24]
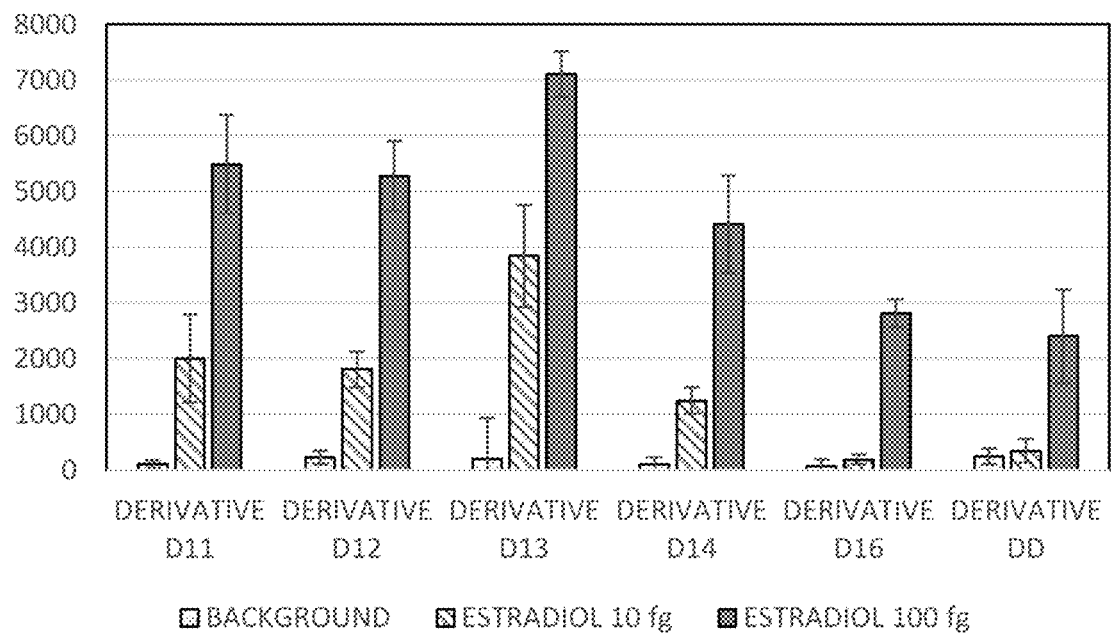

[Fig. 25]
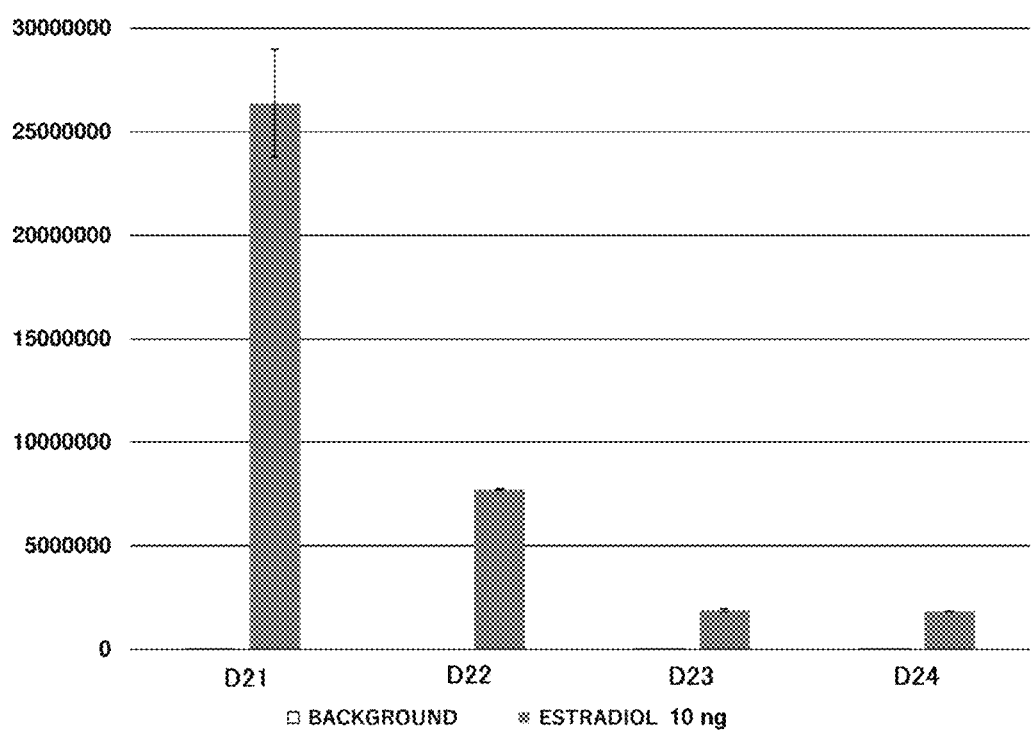

[Fig. 26-1]
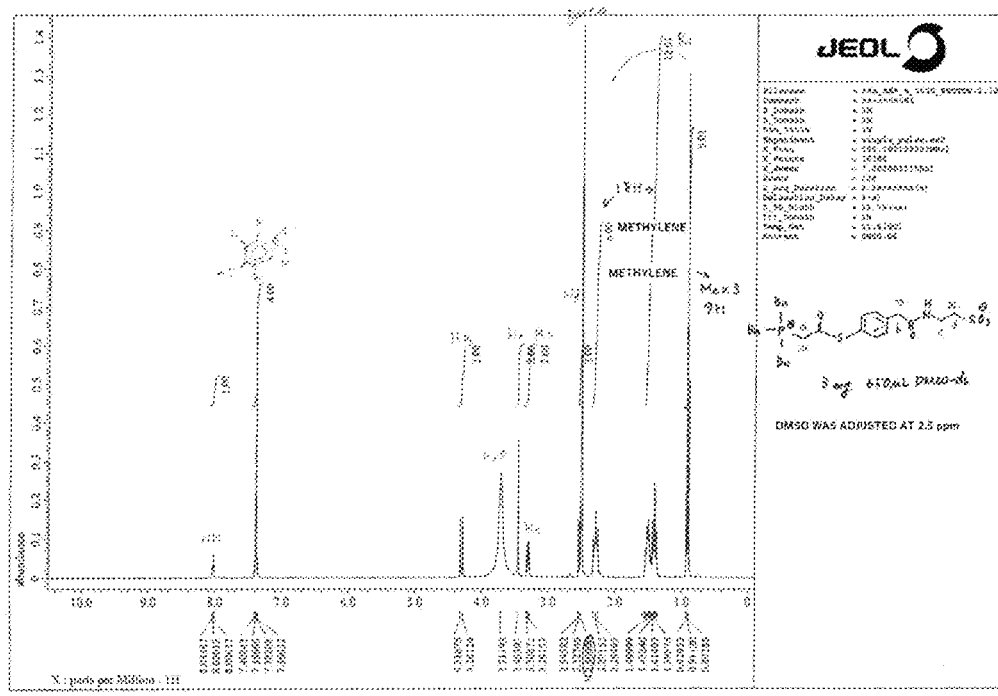

[Fig. 26-2]
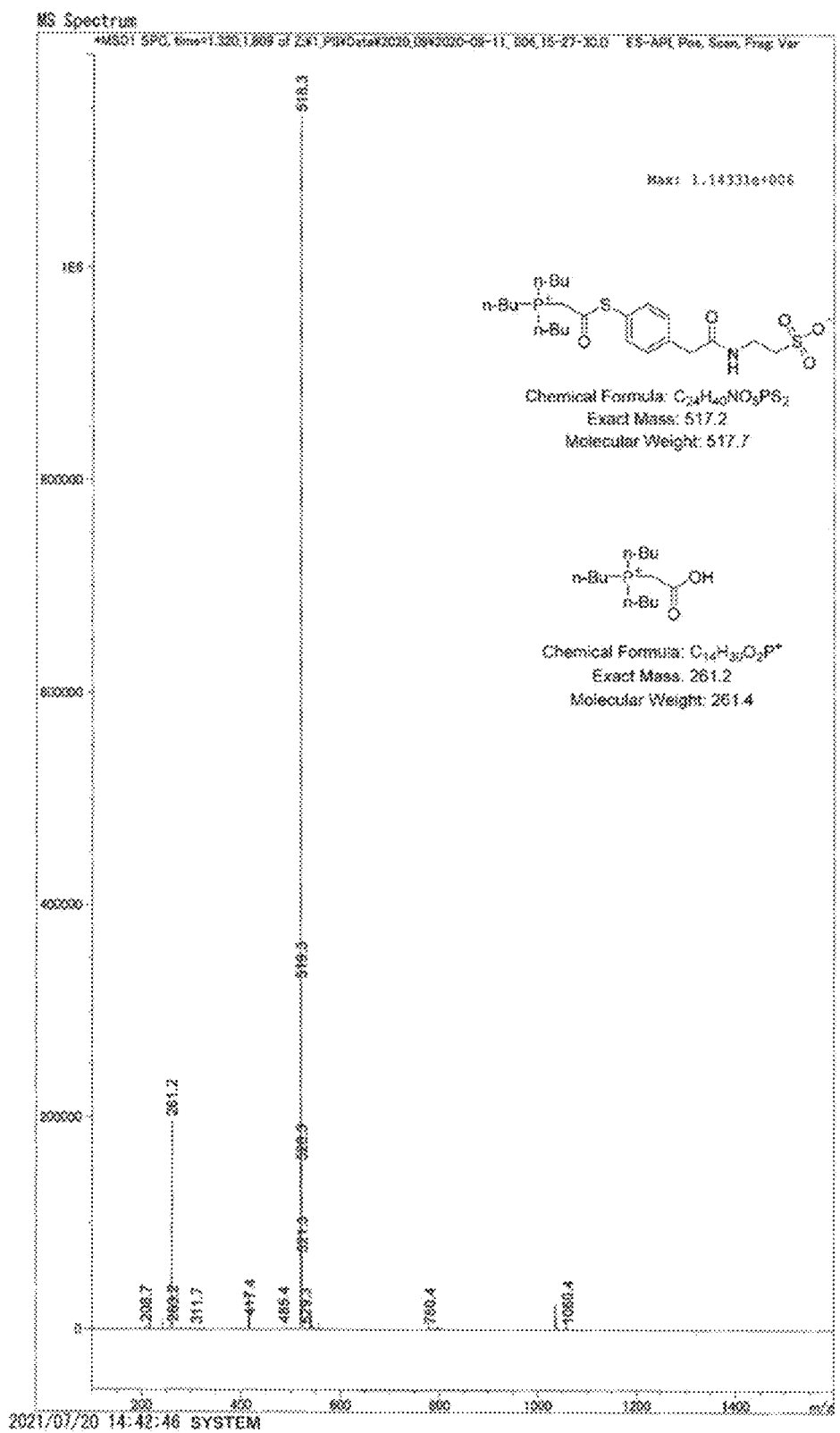

[Fig. 27]
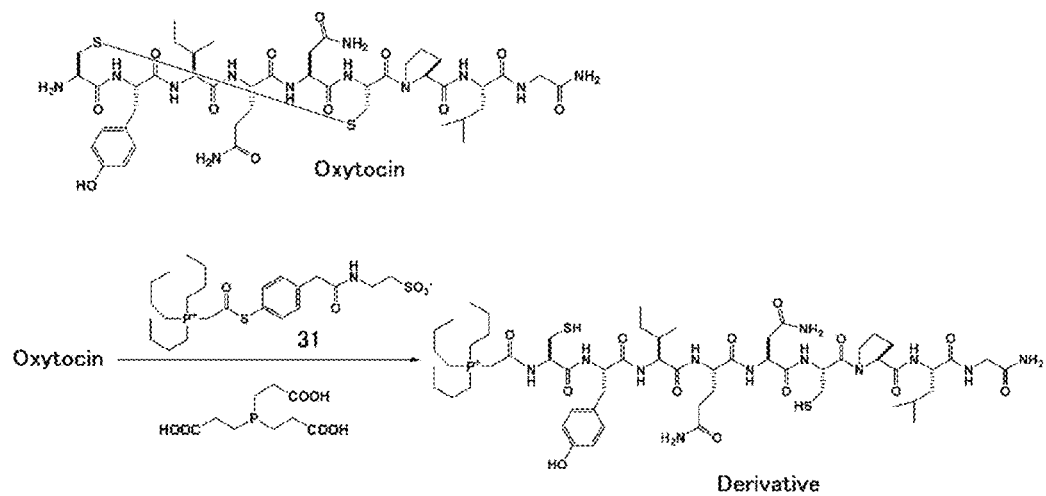
[Fig. 28]
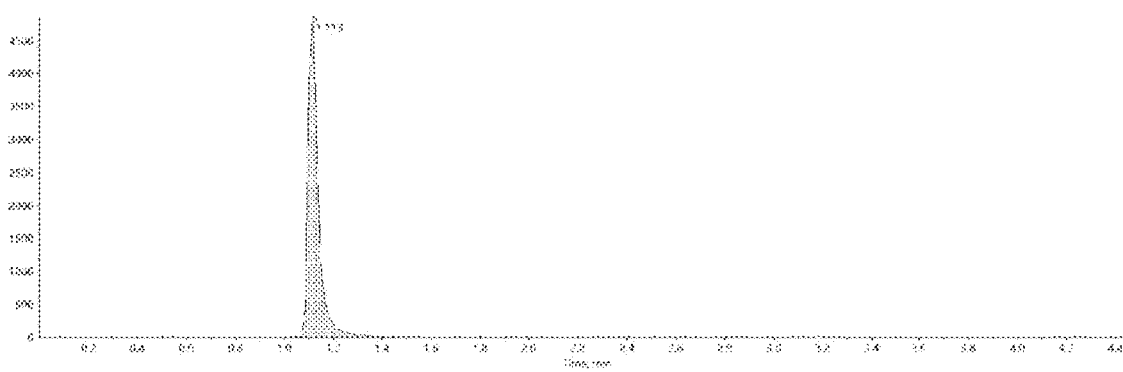
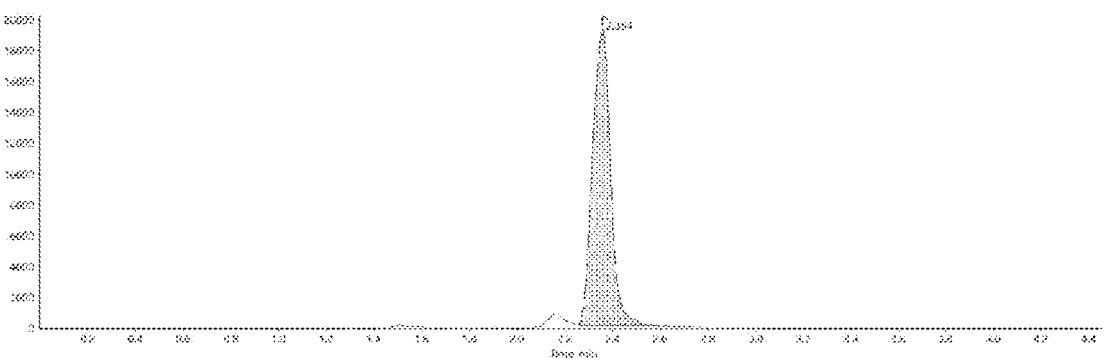

[Fig. 29]
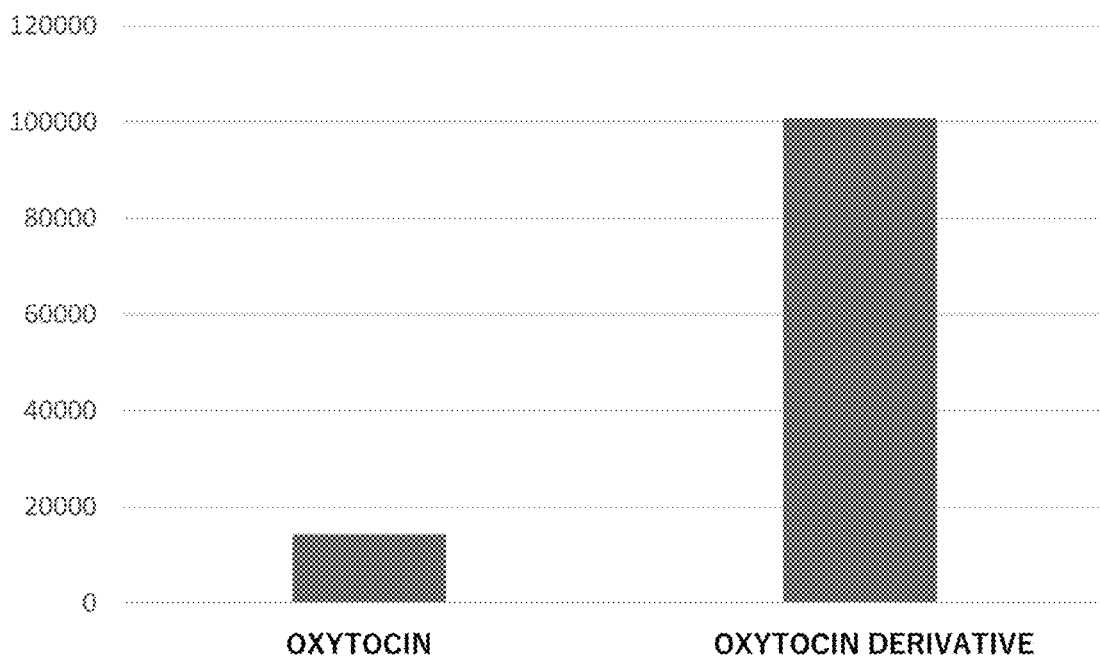

[Fig. 30A]
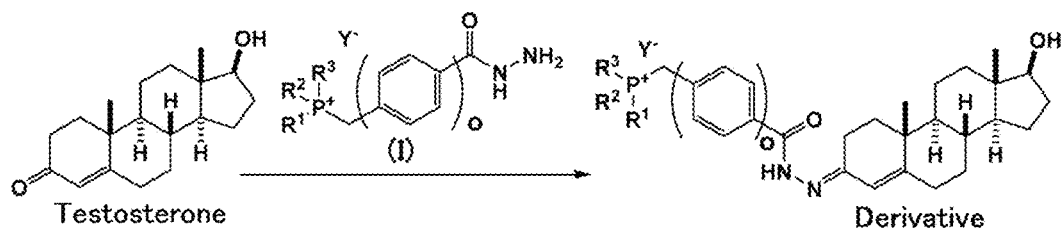
[Fig. 30B]
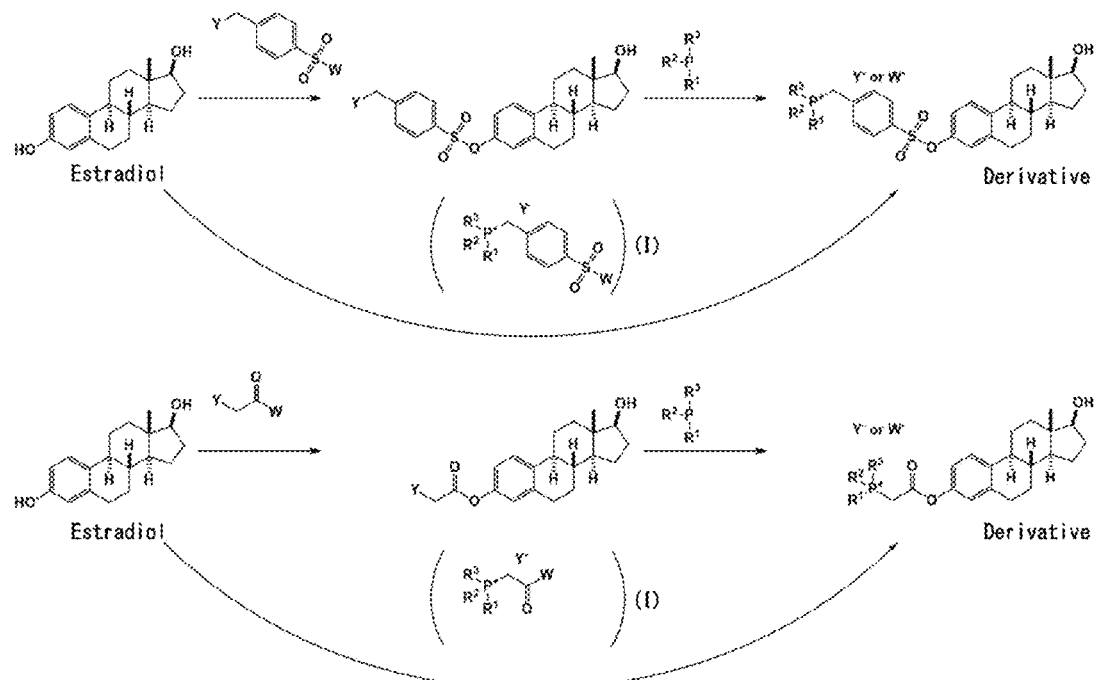

[Fig. 30C]
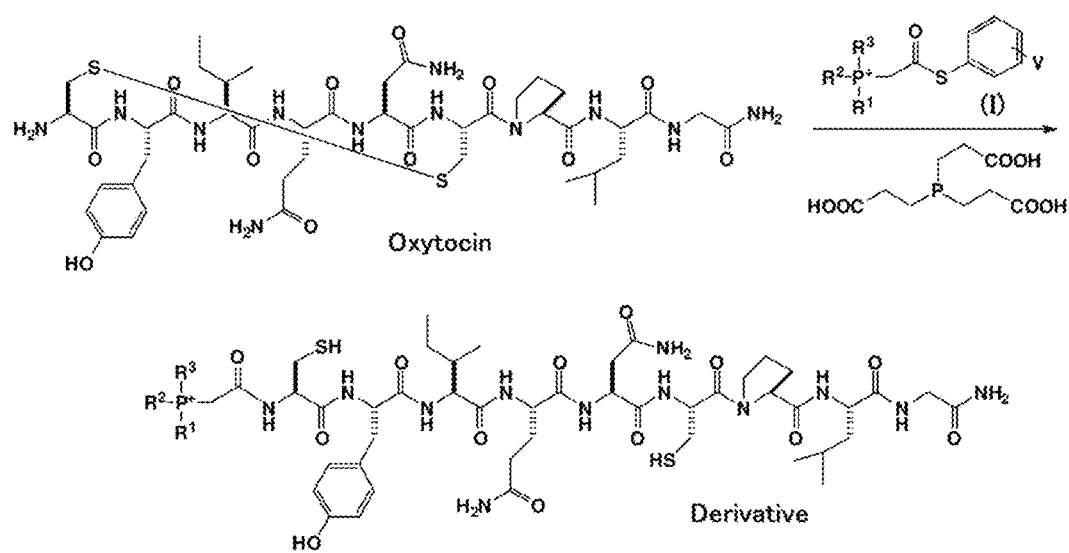

PHOSPHONIUM COMPOUND, REAGENT KIT FOR DERIVATIZATION, MASS SPECTROMETRIC METHOD, AND METHOD FOR PRODUCING PHOSPHONIUM COMPOUND

CROSS-REFERENCE TO RELATED APPLICATION

This application claims priority to Japanese Patent Application No. 2021-165739 filed Oct. 7, 2021, the disclosure of which is hereby incorporated by reference in its entirety.

BACKGROUND OF THE INVENTION

Field of the Invention

The present invention relates to a phosphonium compound, a reagent kit for derivatization, a mass spectrometric method, and a method for producing a phosphonium compound.

Description of Related Art

Liquid chromatography-tandem mass spectrometry (LC-MS/MS) and matrix-assisted laser desorption-ionization mass spectrometry (MALDI-MS) are extremely powerful analytical techniques for quantitatively determining trace amounts of metabolites or contents. In these analytical techniques, a target compound is ionized. In analysis in which a target compound is ionized, some target compounds may be ionized inefficiently and thus cannot be detected, or detection accuracy may be insufficient for quantitative determination in many cases. To address such problems, a target compound may be derivatized to improve ionization efficiency.

For example, J. Chromatogr. B 2011, 879, 1159-1165 and Biomed. Chromatogr. 2021, 35, e5036 disclose derivatization of lipophilic hormones containing no nitrogen atom (androgen or estrogen) with a derivatization reagent containing a nitrogen atom.

SUMMARY OF THE INVENTION

The present invention is intended to provide a novel technique for improving the ionization efficiency of a target compound.

It has been found as discussed in this disclosure that a particular phosphonium compound is suitable for derivatization to improve ionization efficiency.

The present invention provides a phosphonium compound represented by Formula (I):

[Chemical Formula I]

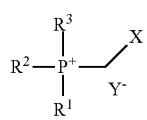

[in Formula (I),
$R^1$, $R^2$, and $R^3$ are independently from each other, an alkyl group or an aryl group, the alkyl group is a substituted or unsubstituted, linear or branched alkyl group having 1 to 20 carbon atoms or a substituted or unsubstituted cyclic alkyl group having 5 to 20 carbon atoms, the aryl group is a substituted or unsubstituted aryl group having 6 to 20 carbon atoms;

X is a reactive group having a hydrazide group, a halide group, a pseudohalide group, or a thioester group; and $Y^-$ is an anion having a total charge of $-1$, or $Y^-$ is absence].

In Formula (I), the alkyl group may be a substituted or unsubstituted, linear or branched alkyl group having 1 to 10 carbon atoms or a substituted or unsubstituted cyclic alkyl group having 5 to 10 carbon atoms, and the aryl group may be a substituted or unsubstituted aryl group having 6 to 10 carbon atoms In Formula (I), $R^1$, $R^2$, and $R^3$ may each independently be

[Chemical Formula 2]

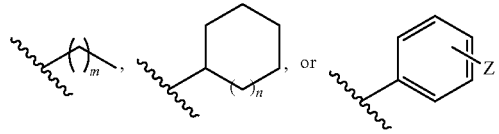

[in the formulae, m is any integer of 0 to 8; n is any integer of 0 to 5; Z is H, $NH_2$, $COO^-$, COOM, $SO_3^-$ (a sulfonate ion group), or $SO_3M$ (a sulfonic acid group or a sulfonate salt group); and M is a hydrogen atom, a lithium atom, a sodium atom, or a potassium atom].

In Formula (I),
when X is a reactive group having a hydrazide group, the reactive group may be

[Chemical Formula 3]

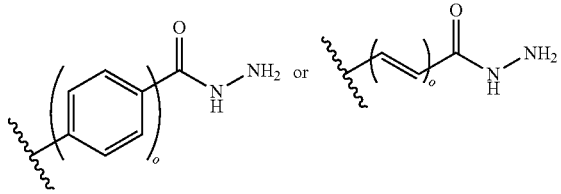

wherein o may be any integer of 0 to 6;

when X is a reactive group having a halide group or a pseudohalide group, the reactive group may be

[Chemical Formula 4]

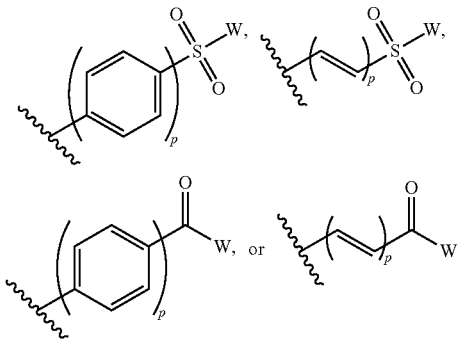

wherein W may be a halogen or a pseudohalogen, and p may be any integer of 0 to 6; or when X is a reactive group having a thioester group, the reactive group may be

[Chemical Formula 5]

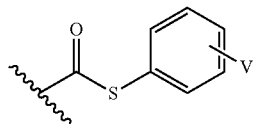

wherein V is H, NH$_2$, SO$_3^-$ (a sulfonate ion group), SO$_3$M, COO$^-$, COOM, or a hydrophilic tag, and M is a hydrogen atom, a lithium atom, a sodium atom, or a potassium atom.

The present invention also provides a phosphonium compound represented by Formula (I):

[Chemical Formula 6]

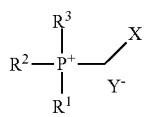

(I)

[in Formula (I),

R$^1$, R$^2$, and R$^3$ are an identical hydrophobic hydrocarbon group or different hydrophobic hydrocarbon groups;

X is a reactive group to react with an oxygen atom-containing functional group or a nitrogen atom-containing functional group; and Y$^-$ is a counter anion, or Y$^-$ is absence].

The present invention also provides a phosphonium compound represented by Formula (II):

[Chemical Formula 7]

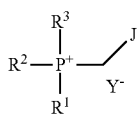

(II)

[in Formula (II),

R$^1$, R$^2$, and R$^3$ are independently from each other, an alkyl group or an aryl group, the alkyl group is a substituted or unsubstituted, linear or branched alkyl group having 1 to 20 carbon atoms or a substituted or unsubstituted cyclic alkyl group having 5 to 20 carbon atoms, the aryl group is a substituted or unsubstituted aryl group having 6 to 20 carbon atoms;

J represents a group formed by reaction of a reactive group having a hydrazide group, a halide group, a pseudohalide group, or a thioester group with a compound to be derivatized; and Y$^-$ is an anion having a total charge of −1, or Y$^-$ is absence].

J may be

[Chemical Formula 8]

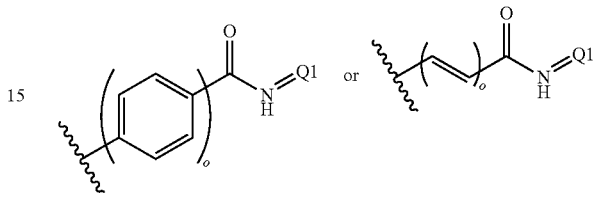

(wherein o is any integer of 0 to 6; and Q1 is a group formed by reaction of a hydrazide group with a carbonyl group contained in the compound to be derivatized);

J may be

[Chemical Formula 9]

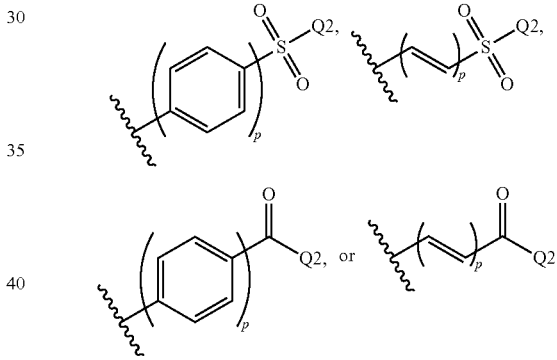

(wherein p is any integer of 0 to 6; and Q2 is a group formed by reaction of a halide group or a pseudohalide group with a phenol group or a hydroxy group contained in the compound to be derivatized); or J may be

[Chemical Formula 10]

(wherein Q3 is a group formed by reaction of a thioester group with an amino group contained in the compound to be derivatized).

The present invention further provides a reagent for derivatization comprising a phosphonium compound represented by Formula (I).

The present invention also provides a reagent kit for derivatization comprising a phosphine compound below:

[Chemical Formula 11]

(wherein $R^1$, $R^2$, and $R^3$ are independently from each other, an alkyl group or an aryl group, the alkyl group is a substituted or unsubstituted, linear or branched alkyl group having 1 to 20 carbon atoms or a cyclic alkyl group having 5 to 20 carbon atoms, and the aryl group is a substituted or unsubstituted aryl group having 6 to 20 carbon atoms), and a reactive compound having a hydrazide group, a halide group, a pseudohalide group, or a thioester group.

The present invention further provides a mass spectrometric method comprising derivatizing a compound to be analyzed by mass spectrometry using the phosphonium compound of Formula (I), the reagent for derivatization, or the reagent kit for derivatization.

The present invention also provides a method for producing the phosphonium compound according to the present invention, wherein X is a reactive group having a hydrazide group, the method comprising a first reaction step of reacting a phosphine compound below:

[Chemical Formula 12]

(wherein $R^1$, $R^2$, and $R^3$ are independently from each other, an alkyl group or an aryl group, the alkyl group is a substituted or unsubstituted, linear or branched alkyl group having 1 to 20 carbon atoms or a substituted or unsubstituted cyclic alkyl group having 5 to 20 carbon atoms, and the aryl group is a substituted or unsubstituted aryl group having 6 to 20 carbon atoms) with a halogenated ethyl carboxylate below:

[Chemical Formula 13]

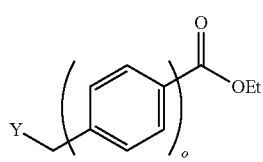

to give a compound below:

[Chemical Formula 14]

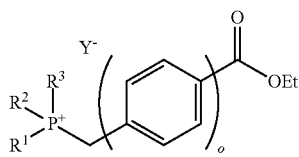

and, a second reaction step of reacting the compound formed in the first reaction step with hydrazine to form the phosphonium compound.

The present invention also provides a method for producing the phosphonium compound according the present invention, where X is a reactive group having a thioester group, the method comprising reacting a phosphonium acetic acid below:

[Chemical Formula 15]

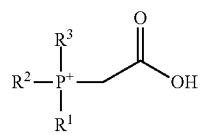

(wherein $R^1$, $R^2$, and $R^3$ are independently from each other, an alkyl group or an aryl group, the alkyl group is a substituted or unsubstituted, linear or branched alkyl group having 1 to 20 carbon atoms or a substituted or unsubstituted cyclic alkyl group having 5 to 20 carbon atoms, and the aryl group is a substituted or unsubstituted aryl group having 6 to 20 carbon atoms) with a thiol below:

[Chemical Formula 16]

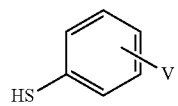

(wherein V is H, $NH_2$, $SO_3^-$ (a sulfonate ion group), $SO_3M$, $COO^-$, $COOM$, or a hydrophilic tag; and M is a hydrogen atom, a lithium atom, a sodium atom, or a potassium atom) to form the phosphonium compound.

Advantageous Effects of Invention

According to the present invention, ionization efficiency can be improved in an analytical method in which a target compound is ionized, such as a mass spectrometric method. This can improve the detection sensitivity of such an analytical method.

The effect of the invention is not limited to that described in this paragraph and may be any of the effect described in the present description.

BRIEF DESCRIPTION OF DRAWINGS

FIG. 1-1 shows NMR spectra of compound 1.
FIG. 1-2 shows NMR and ESI mass spectra of compound 1.

FIG. 2-1 shows NMR spectra of compound 2.
FIG. 2-2 shows NMR and ESI mass spectra of compound 2.
FIG. 3-1 shows NMR spectra of compound 3.
FIG. 3-2 shows NMR and ESI mass spectra of compound 3.
FIG. 4-1 shows NMR spectra of compound 4.
FIG. 4-2 shows NMR and ESI mass spectra of compound 4.
FIG. 5-1 shows NMR spectra of compound 5.
FIG. 5-2 shows NMR and ESI mass spectra of compound 5.
FIG. 6-1 shows NMR spectra of compound 6.
FIG. 6-2 shows NMR and ESI mass spectra of compound 6.
FIG. 7-1 shows NMR spectra of compound 7.
FIG. 7-2 shows NMR and ESI mass spectra of compound 7.
FIG. 8-1 shows NMR spectra of compound 8.
FIG. 8-2 shows NMR and ESI mass spectra of compound 8.
FIG. 9-1 shows NMR spectra of compound 9.
FIG. 9-2 shows NMR and ESI mass spectra of compound 9.
FIG. 10 is a view showing the structures of phosphonium compounds.
FIG. 11 is a view showing a reaction formula of derivatization of testosterone.
FIG. 12 is a view showing the chemical structures of testosterone derivatives.
FIG. 13 is a view showing the chemical structures of Girard's reagents T and P.
FIG. 14-1 shows SRM chromatograms of formed derivatives.
FIG. 14-2 shows SRM chromatograms of formed derivatives.
FIG. 14-3 shows SRM chromatograms of formed derivatives.
FIG. 14-4 shows SRM chromatograms of formed derivatives.
FIG. 14-5 shows SRM chromatograms of formed derivatives.
FIG. 14-6 shows SRM chromatograms of formed derivatives.
FIG. 15-1 is a graph showing observed peak areas.
FIG. 15-2 is a graph showing observed peak areas.
FIG. 16 is a view showing a reaction scheme of derivatization of estradiol.
FIG. 17 shows NMR spectra of a reaction intermediate.
FIG. 18-1 shows NMR spectra of derivative D11.
FIG. 18-2 shows NMR and ESI mass spectra of derivative D11.
FIG. 19 is a view showing the chemical structures of formed estradiol derivatives.
FIG. 20 is a view showing the chemical structure of a formed estradiol derivative.
FIG. 21 is a view showing the chemical structures of formed estradiol derivatives.
FIG. 22-1 shows SRM chromatograms of formed derivatives.
FIG. 22-2 shows SRM chromatograms of formed derivatives.
FIG. 22-3 shows SRM chromatograms of formed derivatives.
FIG. 22-4 shows SRM chromatograms of formed derivatives.
FIG. 22-5 shows SRM chromatograms of formed derivatives.
FIG. 22-6 shows SRM chromatograms of formed derivatives.
FIG. 22-7 shows an SRM chromatogram of a formed derivative.
FIG. 23 is a graph showing measured peak areas.
FIG. 24 is a graph showing measured peak areas.
FIG. 25 is a graph showing measured peak areas.
FIG. 26-1 shows NMR spectral data of compound 31.
FIG. 26-2 shows MS spectral data of compound 31.
FIG. 27 is a view showing a reaction scheme of derivatization of oxytocin.
FIG. 28 shows SRM chromatograms of formed derivatives.
FIG. 29 is a graph showing observed peak areas.
FIG. 30A is a view showing a reaction scheme of derivatization of testosterone.
FIG. 30B is a view showing reaction scheme of derivatization of estradiol.
FIG. 30C is a view showing a reaction scheme of derivatization of oxytocin.

DESCRIPTION OF THE INVENTION

Non-limiting embodiments of the present invention will be described below. However, the present invention is not limited to the following non-limiting embodiments, which can be arbitrarily changed within the scope of the invention.

1. Description of the Present Invention

The above-described mass spectrometry such as LC-MS/MS and MALDI-MS is an extremely powerful analytical technique for quantitatively determining trace amounts of metabolites or contents. Some compounds are, however, ionized inefficiently and thus cannot be detected or can be detected only at insufficient accuracy for quantitative determination.

For samples such as foods and supplements that are available in a certain amount, a larger amount of a sample can be used to compensate insufficient sensitivity. However, for such a sample, a smaller amount of a sample is desirably used to detect or quantitatively determine a target compound, and it is desirable to improve the ionization efficiency.

In analysis of a target compound such as a human metabolite, the amount of a sample containing the target compound cannot be easily increased in many cases. For such a target compound, it is very important to improve the ionization efficiency.

To improve the detection sensitivity, not only apparatus improvement such as higher sensitivity of a mass spectrometer but also modification (derivatization) of a target compound for higher ionization efficiency have been widely developed. A biometabolite is typically an organic compound mainly comprising carbon, hydrogen, oxygen, and nitrogen, and an oxygen atom or a nitrogen atom, which has a lone electron pair, is likely to be added with a hydrogen ion (proton) and has high ionization efficiency. In particular, a nitrogen atom has higher protonation properties than an oxygen atom, and a compound containing a nitrogen atom is more likely to be ionized than compounds containing no nitrogen atom.

As described above, a lipophilic hormone contains no nitrogen atom, and thus a derivatization reagent containing a nitrogen atom has been used to introduce a nitrogen atom and to improve the ionization efficiency. Meanwhile, peptides and proteins, which contain nitrogen atoms, are typically, more likely to be ionized than lipophilic hormones, and thus derivatization is not necessarily a typical method for peptides and proteins.

Trace metabolites and the like have been analyzed by using a mass spectrometer, but it is desirable to further improve the sensitivity for accurate quantitative determination.

In LC-MS/MS, which is a conventional method of quantitative mass spectrometry, a target compound is ionized by electrospray ionization (ESI), and thus easiness of ionization of a target compound depends on the polarity (easiness of protonation) of the target compound and the organic solvent composition of a mobile phase that volatilizes in ionization. Different compounds have different structures and different polarities, and thus further improvement of the detection sensitivity involves optimization of the ionization efficiency for each compound.

In LC-MS/MS, selective reaction monitoring (SRM) enables quantitative determination at higher sensitivity, and thus fragmentation to give a lower background is also important.

The inventors of the present invention have found that a specific phosphonium compound can improve ionization efficiency in an analytical method in which a target compound is ionized. In other words, the present invention provides a phosphonium compound that has a group for controlling the hydrophobicity of a target compound and a group to react with a target compound.

The phosphonium compound comprises a phosphorus atom. Phosphorus belongs to group 15 in the periodic table as with nitrogen, which is just above phosphorus. A phosphorus atom has a lone electron pair as with a nitrogen atom and thus is likely to be protonated.

In addition, a phosphorus atom has electrons in the d orbital and thus is softer than a nitrogen atom in accordance with HSAB (hard and soft acids and bases) rule and is likely to occur nucleophilic substitution reaction with an alkyl or a benzyl halide. Hence, a wide variety of hydrophobic substituents can be easily introduced onto a phosphorus atom. Accordingly, a hydrophobic substituent appropriate for a target compound can be bonded to a phosphorus atom, and a derivatization reagent optimum for a target compound can be provided.

A peptide or a protein has a plurality of reaction sites such as an amino group not only at the N-terminal but also on a lysine residue side chain. When derivatization reaction through an amino group is carried out, multiple types of reaction products may be formed, and this can adversely affect the sensitivity of quantitative analysis. According to the present invention, a peptide or a protein having a cysteine residue at the N-terminal (for example, a peptide hormone such as oxytocin and vasopressin) can be selectively derivatized, for example, by native chemical ligation. According to the present invention, multiple types of reaction products can be prevented from forming, and unintended derivatization reaction of compounds can also be prevented. This can reduce background noise in mass spectrometry to improve the detection sensitivity.

The phosphonium compound according to the present invention can be used to charge a target compound and to introduce appropriate hydrophobicity. This enables mass spectrometry of a target compound and can optimize the detection sensitivity of quantitative analysis.

According to the present invention, for example, in the clinical examination field, a trace metabolite can be detected by mass spectrometry at high sensitivity and can be quantitatively determined at high sensitivity. The present invention is applicable to any type of mass spectrometer. For example, to widely spread the quantitative determination of a trace metabolite by mass spectrometry in the clinical examination field, it is desirable to yield the same value regardless of the time, the place, and the apparatus from any manufacturer. The improvement in detection sensitivity by the present invention compensates the difference between apparatuses from various manufacturers and thus can help the spread of quantitative determination of a trace metabolite by mass spectrometry.

The present invention will next be described in further detail.

2. First Embodiment (Phosphonium Compound)

The present invention provides a phosphonium compound represented by Formula (I):

[Chemical Formula 17]

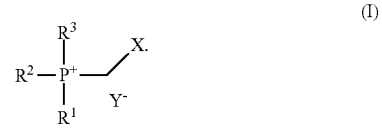

Components of Formula (I) will next be described.

In Formula (I), $R^1$, $R^2$, and $R^3$ may each independently be an alkyl group or an aryl group. The alkyl group is a substituted or unsubstituted, linear or branched alkyl group having 1 to 20 carbon atoms or a substituted or unsubstituted cyclic alkyl group having 5 to 20 carbon atoms. The aryl group is a substituted or unsubstituted aryl group having 6 to 20 carbon atoms. $R^1$, $R^2$, and $R^3$ can impart hydrophobicity to a target compound to be derivatized. The types of $R^1$, $R^2$, and $R^3$ may be appropriately selected by a person skilled in the art depending on a hydrophobicity to be imparted.

The alkyl group may be a substituted or unsubstituted, linear or branched alkyl group having 1 to 20 carbon atoms. The carbon number of the linear or branched alkyl group may preferably be 1 to 18 and may, for example, be 1 to 16, 1 to 14, 1 to 12, or 1 to 10. The carbon number excludes the number of carbon atoms of substituents.

In one embodiment, the linear or branched alkyl group may be an unsubstituted alkyl group or may be an alkyl group in which only hydrogen atoms are bonded to the carbon chain.

In another embodiment, the linear or branched alkyl group may be a substituted alkyl group, or one or more substituents may be bonded to the carbon chain in addition to hydrogen atoms. Examples of the substituent include, but are not limited to, an alkoxy group, an aryl group, a hydroxy group, an amino group, and a halogen atom. The position and the number of the substituents may be appropriately selected by a person skilled in the art depending on various factors such as hydrophobicity to be introduced. For a linear or branched alkyl group having two or more substituents, the substituents may be the same or different.

The alkyl group may be a substituted or unsubstituted cyclic alkyl group having 5 to 20 carbon atoms. The carbon number of the cyclic alkyl group may preferably be 5 to 18 and may, for example, be 5 to 16, 5 to 14, 5 to 12, or 5 to 10. The carbon number excludes the number of carbon atoms of substituents.

In one embodiment, the cyclic alkyl group may be an unsubstituted cyclic alkyl group or may be an alkyl group in which only hydrogen atoms are bonded to the carbon chain.

In another embodiment, the cyclic alkyl group may be a substituted alkyl group, or one or more substituents may be bonded to the carbon chain in addition to hydrogen atoms. Examples of the substituent include, but are not limited to, an alkoxy group, an aryl group, a hydroxy group, an amino group, and a halogen atom. The position and the number of the substituents may be appropriately selected by a person skilled in the art depending on various factors such as hydrophobicity to be introduced. For a cyclic alkyl group having two or more substituents, the substituents may be the same or different.

The aryl group is a substituted or unsubstituted aryl group having 6 to 20 carbon atoms. The carbon number of the aryl group is preferably 6 to 18 and may, for example, be 6 to 16, 6 to 14, 6 to 12, or 6 to 10. The carbon number excludes the number of carbon atoms of substituents.

In one embodiment, the aryl group may be an unsubstituted aryl group, may, for example, be a phenyl group or a naphthyl group, and may specifically be a phenyl group.

In another embodiment, the aryl group may be a substituted aryl group. Examples of the substituent of the substituted aryl group include an amino group, COO$^-$ (a carboxylate ion group), COOM (a carboxy group or a carboxylate salt group), SO$_3^-$ (a sulfonate ion group), SO$_3$M (a sulfonic acid group or a sulfonate salt group), an alkyl group, an alkoxy group, an aryl group, a hydroxy group, and a halogen atom. The number of the substituents may be one or two or more. When the substituted aryl group has two or more substituents, the substituents may be the same or different. In COOM and SO$_3$M, M may be a hydrogen atom or may be an alkali metal atom. The alkali metal atom may, for example, be a lithium atom, a sodium atom, or a potassium atom.

In one non-limiting embodiment of the present invention, $R^1$, $R^2$, and $R^3$ in Formula (I) may each independently be

[Chemical Formula 18]

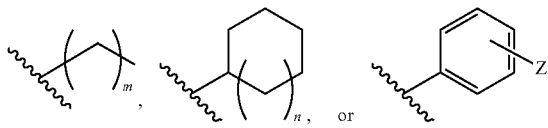

[wherein m may be any integer of 0 to 8 and may particularly be any integer of 0 to 6; n may be any integer of 0 to 5 and may, for example, be any integer of 0 to 4; Z is H, NH$_2$, COO$^-$, COOM, SO$_3^-$ (a sulfonate ion group), or SO$_3$M (a sulfonic acid group or a sulfonate salt group); and M is a hydrogen atom, a lithium atom, a sodium atom, or a potassium atom].

In Formula (I), X is a reactive group having a hydrazide group, a halide group, a pseudohalide group, or a thioester group. Through the reactive group, the phosphonium compound of Formula (I) can be bonded to a target compound. The type of the reactive group may be appropriately selected by a person skilled in the art depending on the type of a target compound. The reactive group may, for example, be a reactive group to react with a functional group having an oxygen atom (for example, a carbonyl group, a phenol group, or a hydroxy group) or may be a reactive group to react with a functional group having a nitrogen atom (for example, an amino group).

In one embodiment, X in Formula (I) may be a reactive group having a hydrazide group. In the embodiment, the reactive group may be a group to react with a functional group having an oxygen atom or, for example, may be a group to react with a carbonyl group.

In the embodiment, the reactive group is particularly preferably

[Chemical Formula 19]

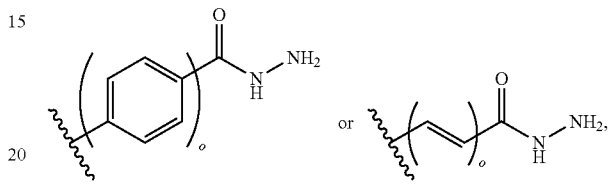

wherein o may be any integer of 0 to 6, o may, for example, be any integer of 0 to 4, and o may specifically be 0, 1, or 2.

In another embodiment, X in Formula (I) may be a reactive group having a halide group or a pseudohalide group (for example, a triflate group or a tosylate group) and may, for example, be a reactive group having a sulfonyl halide group, an acetyl halide group, a sulfonyl triflate group, an acetyl triflate group, a sulfonyl tosylate group, or an acetyl tosylate group. X in Formula (I) is particularly preferably a reactive group having a sulfonyl halide group, a sulfonyl triflate group, or a sulfonyl tosylate group and is more preferably a reactive group having a sulfonyl halide group or a sulfonyl triflate group. These groups are excellent from the viewpoint of improving the sensitivity of mass spectrometry. In the embodiment, the reactive group may be a group to react with a functional group having an oxygen atom and may specifically be a group to react with a phenol group or a hydroxy group.

In the embodiment, the reactive group is particularly preferably

[Chemical Formula 20]

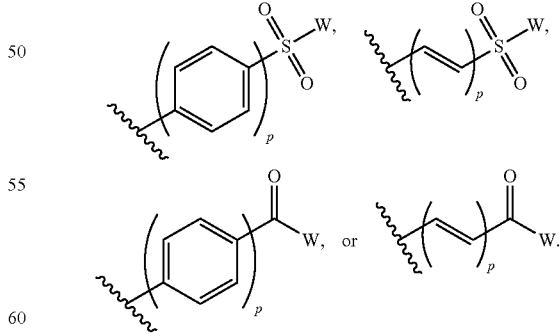

In the formulae, W is a halogen atom (for example, F, Cl, or Br) or a pseudohalogen (for example, a triflate group (TfO) or a tosylate group). p may be any integer of 0 to 6, p may, for example, be any integer of 0 to 4, and p may specifically be 0, 1, or 2.

In another embodiment, X in Formula (I) may be a reactive group having a thioester group. In the embodiment, the reactive group may be a group to react with a functional group having a nitrogen atom and may particularly be a group to react with an amine.

In the embodiment, the reactive group is particularly preferably

[Chemical Formula 21]

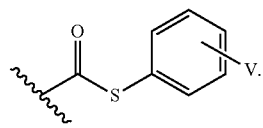

In the formula, V is H, $NH_2$, $SO_3^-$ (a sulfonate ion group), $SO_3M$, $COO^-$, COOM, or a hydrophilic tag, and M is a hydrogen atom, a lithium atom, a sodium atom, or a potassium atom.

In Formula (I), $Y^-$ is an anion having a total charge of −1, or $Y^-$ is absence. The anion may, for example, be a halogen ion (for example, $F^-$, $Cl^-$, or $BR^-$) or a pseudohalogen ion (for example, a triflate ion or a tosylate ion).

The phosphonium compound having such a structural feature as described above can be used to impart a permanent positive charge to a target compound.

The phosphonium compound of the present invention comprises a reactive group to react with a functional group having an oxygen atom or a nitrogen atom as described above.

When the reactive group comprises hydrazide, the target compound may be a compound having a carbonyl group. In this case, the target compound is, for example, androgen, specifically testosterone, but is not limited to them.

When the reactive group comprises a halide group or a pseudohalide group, the target compound may be a compound having a phenol group or a hydroxy group. In this case, the target compound is, for example, estrogen, specifically estradiol, but is not limited to them.

When the reactive group is a thioester, the target compound may be a compound having an amino group. In this case, the target compound is, for example, a peptide or a protein having a cysteine residue at the N-terminal, specifically oxytocin, but is not limited to them.

The target compound may be contained in a biological sample. The biological sample capable of containing a target compound that is to be derivatized with the phosphonium compound of the present invention may, for example, be a body fluid or a sample derived from a body fluid and more specifically be any of serum, plasma, blood, urine, spinal fluid, and saliva. Such a biological sample may be subjected to a certain pretreatment suitable for an analytical method as needed and then be subjected to derivatization treatment with the phosphonium compound of the present invention, which makes it possible to detect a target compound.

By reacting the phosphonium compound of the present invention with a target compound, the target compound is positively charged, and the hydrophobicity of the target compound can be controlled (especially, the hydrophobicity of the target compound can be increased or decreased). By positively charging a target compound to be analyzed by mass spectrometry and by controlling the hydrophobicity as described above, the ionization efficiency of the target compound can be increased to result in an improvement in detection sensitivity in mass spectrometry.

The reaction type between the phosphonium compound of the present invention and a target compound may be selected depending on the type of reactive group X of the phosphonium compound.

When the reactive group X is a hydrazide group, the reaction type may be dehydration condensation. In this case, derivatization as shown in FIG. 30A proceeds.

When the reactive group X is a halide group or a pseudohalide group, the reaction type may be electrophilic substitution. In this case, derivatization as shown in FIG. 30B proceeds. The upper reaction formula in the figure shows derivatization reaction when the halide group is a sulfonyl halide group. The lower reaction formula in the figure shows derivatization reaction when the halide group is an acetyl halide group.

When the reactive group X is a thioester group, the reaction type may be native chemical ligation (also referred to as NCL). In this case, derivatization as shown in FIG. 30C proceeds.

The present invention, for example, provides the following compounds, but the present invention is not limited to these compounds. $R^1$, $R^2$, $R^3$, X, and Y in Formula (I) may be appropriately selected, for example, depending on a target compound or the type of analytical method.

Examples of the phosphonium compound according to the present invention where X is a reactive group having a hydrazide group include the following compounds:
(2-hydrazinyl-2-oxoethyl)trimethylphosphonium bromide;
(4-(hydrazinecarbonyl)benzyl)trimethylphosphonium bromide;
benzyl(2-hydrazinyl-2-oxoethyl)dimethylphosphonium bromide;
(2-hydrazinyl-2-oxoethyl)triethylphosphonium bromide;
benzyl(2-hydrazinyl-2-oxoethyl)diethylphosphonium bromide;
(2-hydrazinyl-2-oxoethyl)triphenylphosphonium bromide;
tributyl(4-(hydrazinecarbonyl)benzyl)phosphonium bromide;
tributyl(2-hydrazinyl-2-oxoethyl)phosphonium bromide; and
(2-hydrazinyl-2-oxoethyl)diphenyl(3-sulfophenyl)phosphonium bromide.

Examples of the phosphonium compound according to the present invention where X is a reactive group having a halide group or a pseudohalide group include the following compounds:
(4-(chlorosulfonyl)benzyl)trimethylphosphonium bromide;
(4-(chlorosulfonyl)benzyl)triethylphosphonium bromide;
(4-(chlorosulfonyl)benzyl)dimethylphenylphosphonium bromide;
(4-(chlorosulfonyl)benzyl)diethylphenylphosphonium bromide;
(4-(chlorosulfonyl)benzyl)diphenylmethylphosphonium bromide;
(4-(chlorosulfonyl)benzyl)triphenylphosphonium bromide;
(4-(chlorosulfonyl)benzyl)tributylphosphonium bromide;
(4-(chlorosulfonyl)benzyl)tricyclohexylphosphonium bromide;
(2-bromo-2-oxoethyl)trimethylphosphonium bromide;
(2-bromo-2-oxoethyl)triethylphosphonium bromide;
(2-bromo-2-oxoethyl)dimethylphenylphosphonium bromide; and
(2-bromo-2-oxoethyl)diethylphenylphosphonium bromide.

Examples of the phosphonium compound according to the present invention where X is a reactive group having a thioester group include the following compound: 2-(2-(4-((tributylphosphonio)acetyl)thio)phenyl)acetamide)ethane-1-sulfonate.

3. Second Embodiment (Phosphonium Compound)

The present invention also provides a phosphonium compound represented by Formula (I):

[Chemical Formula 22]

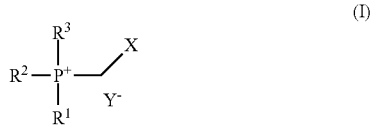

[in Formula (I),
$R^1$, $R^2$, and $R^3$ are an identical hydrophobic hydrocarbon group or different hydrophobic hydrocarbon groups;
X is a reactive group to react with an oxygen atom-containing functional group or a nitrogen atom-containing functional group; and
$Y^-$ is a counter anion, or $Y^-$ is absence].

The hydrophobic hydrocarbon group is a hydrocarbon group that controls the hydrophobicity of a target compound (for example, to increase or decrease the hydrophobicity, specifically to increase the hydrophobicity). The hydrophobic hydrocarbon group may, for example, be the alkyl group or the aryl group described for $R^1$, $R^2$, and $R^3$ in the section 2 above, but is not limited to them. The hydrophobic hydrocarbon group may be another hydrocarbon group that is designed to control the hydrophobicity of a target compound (for example, to increase or decrease the hydrophobicity, specifically to increase the hydrophobicity). The other hydrocarbon group may, for example, be an alkenyl group. The alkenyl group may be linear or branched. The alkenyl group may have a substituent. The carbon number of the alkenyl group may preferably be 1 to 20 and more preferably 1 to 18, and may, for example, be 1 to 16, 1 to 14, 1 to 12, or 1 to 10. The carbon number excludes the number of carbon atoms of substituents.

The reactive group to react with an oxygen atom-containing functional group or a nitrogen atom-containing functional group is a reactive group that reacts with the functional group contained in a target compound to form a bond between the target compound and the phosphonium compound of the present invention.

The reactive group to react with an oxygen atom-containing functional group may be a reactive group that react, for example, with a carbonyl group, a phenol group, or a hydroxy group. Examples of the reactive group include a hydrazide group, a halide group, or a pseudohalide group described for X in the section 2 above, but are not limited to them.

The reactive group to react with a nitrogen atom-containing functional group may, for example, be a reactive group to react with an amine. Examples of the reactive group include a thioester group described for X in the section 2 above, but are not limited to them.

The counter anion may be an anion having a total charge of −1. The anion may, for example, be a halogen ion (for example, $F^-$, $Cl^-$, or $Br^-$) or a pseudohalogen ion (for example, a triflate ion or a tosylate ion). The counter anion may be absence.

By using the phosphonium compound, the effect described in the section 2 above is exerted. For example, by using the phosphonium compound, a target compound can be permanently positively charged. By reacting the phosphonium compound with a target compound, the target compound can be positively charged, and the hydrophobicity of the target compound can be controlled (specifically, the hydrophobicity of the target compound can be increased or decreased).

4. Third Embodiment (Phosphonium Compound Bonded to Target Compound)

The present invention also provides a phosphonium compound prepared by bonding the phosphonium compound described in the section 2 or 3 to a target compound. The phosphonium compound is a compound represented by Formula (II).

[Chemical Formula 23]

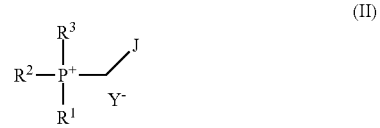

In Formula (II), $R^1$, $R^2$, $R^3$, and $Y^-$ are as described for Formula (I) in the section 2 or 3 above, and the description applies also to the present embodiment. Hence, explanation on $R^1$, $R^2$, $R^3$, and $Y^-$ are omitted.

In Formula (II), J is a group formed by reaction of a reactive group having a hydrazide group, a halide group, a pseudohalide group, or a thioester group with a compound to be derivatized.

The reactive group is as described for Formula (I) in the section 2 or 3 above, and the description applies also to the present embodiment. The compound to be derivatized is the target compound described in the section 2 above, and the description applies also to the present embodiment. A combination of the reactive group and the compound to be derivatized is selected depending on a target compound as described in the section 2 above.

Examples of J will be more specifically described below.
When the reactive group is a reactive group having a hydrazide group, J may be

[Chemical Formula 24]

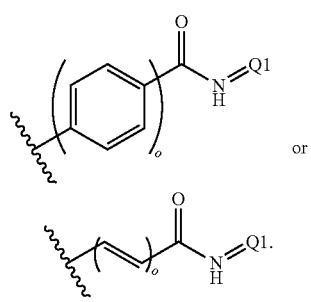

In the formulae, o is any integer of 0 to 6, o may, for example, be any integer of 0 to 4, and o may specifically be 0, 1, or 2. Q1 may be a group formed by reaction (specifically, dehydration condensation) of a hydrazide group with a carbonyl group contained in the compound to be derivatized.

When the reactive group is a reactive group having a halide group or a pseudohalide group, J may be

[Chemical Formula 25]

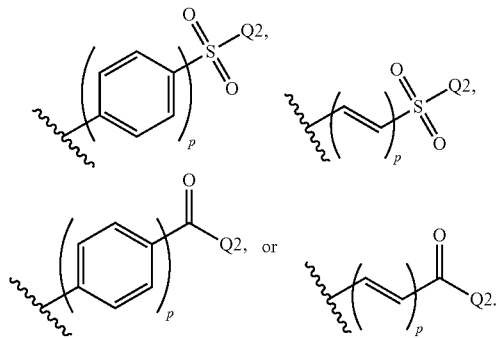

In the formulae, p may be any integer of 0 to 6, p may, for example, be any integer of 0 to 4, and p may specifically be 0, 1, or 2. Q2 is a group formed by reaction (specifically, electrophilic substitution) of a halide group or a pseudohalide group with a phenol group or a hydroxy group contained in the compound to be derivatized.

When the reactive group is a reactive group having a thioester group, J may be

[Chemical Formula 26]

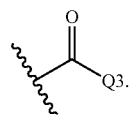

In the formula, Q3 is a group formed by reaction (native chemical ligation) of a thioester group with an amino group contained in the compound to be derivatized.

5. Fourth Embodiment (Reagent for Derivatization)

The present invention further provides a reagent for derivatization comprising the phosphonium compound of Formula (I) described in the section 2 or 3 above. The reagent for derivatization may be a reagent for derivatizing the target compound described in the section 2 above. More specifically, the reagent for derivatization may be a reagent used for positively charging the target compound, specifically for positively charging the target compound and for controlling the hydrophobicity of the target compound.

The reagent for derivatization may comprise a solvent in addition to the phosphonium compound. In other words, in the reagent for derivatization, the phosphonium compound may be present in a solvent. The solvent may be an organic solvent and may, for example, be an alcohol such as methanol, ethanol, and propanol but is not limited to them. The solvent may be water or a mixed solvent of water and the alcohol or acetonitrile.

6. Fifth Embodiment (Reagent Kit for Derivatization)

The present invention also provides a reagent kit for derivatization. The reagent kit is a reagent kit used for forming the compound represented by Formula (II) and described in the section 4 above.

In the derivatization of a target compound by using the phosphonium compound described in the section 2 or 3 above, the phosphonium compound that has $R^1$, $R^2$, and $R^3$ for controlling the hydrophobicity of a target compound and has a reactive group for forming a bond to a target compound is provided, and the phosphonium compound is used to derivatize a target compound.

To derivatize a target compound, the target compound may first be reacted with a reactive group-containing compound to give a coupled compound, and next the coupled compound may be bonded to a phosphine compound having $R^1$, $R^2$, and $R^3$. In this manner, a target compound may be derivatized by successively reacting the target compound with a reactive group-containing compound and then with a phosphine compound. The present invention also provides a reagent kit used for such derivatization.

To derivatize a target compound, the target compound, a reactive group-containing compound, and a phosphine compound having $R^1$, $R^2$, and $R^3$ may be reacted to derivatize the target compound. In this manner, a target compound may be bonded to a reactive group-containing compound and a phosphine compound by a single reaction treatment.

In other words, the reagent kit for derivatization of the present invention may comprise a phosphine compound:

[Chemical Formula 27]

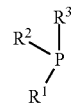

(wherein $R^1$, $R^2$, and $R^3$ are independently from each other, an alkyl group or an aryl group, the alkyl group is a substituted or unsubstituted, linear or branched alkyl group having 1 to 20 carbon atoms or a substituted or unsubstituted cyclic alkyl group having 5 to 20 carbon atoms, and the aryl group is a substituted or unsubstituted aryl group having 6 to 20 carbon atoms), and a reactive compound having a hydrazide group, a halide group, a pseudohalide group, or a thioester group.

To derivatize a target compound by using the reagent kit for derivatization of the present invention, the reactive compound having a hydrazide group, a halide group, a pseudohalide group, or a thioester group is first reacted with the target compound to give a coupled compound of the reactive compound and the target compound. Next, the coupled compound is bonded to the phosphine compound, and consequently the target compound is derivatized.

$R^1$, $R^2$, and $R^3$ contained in the phosphine compound may be as described for the compound of Formula (I) in the section 2 above, and the description applies also to the present embodiment.

The reactive compound may be a compound comprising the reactive group X and the anion $Y^-$ described for the compound of Formula (I) in the section 2 above, and may, for example, be a compound represented by X—Y.

The reactive group X is as described for the compound of Formula (I) in the section 2 above, and the description applies also to the present embodiment. Y is the anion atom described for the compound of Formula (I) in the section 2 above.

In a non-limiting embodiment, X is the reactive group having a halide group or a pseudohalide group or the reactive group having a thioester group described in the section 2 above. As for the derivatization of a target compound by using such a reactive group, the derivatization of a target compound by using the kit according to the present embodiment may yield a derivative at a higher efficiency than the derivatization by using the phosphonium compound described in the section 2.

7. Sixth Embodiment (Mass Spectrometric Method)

The present invention further provides a mass spectrometric method comprising a derivatization step of derivatizing a compound to be analyzed by mass spectrometry, by using the phosphonium compound described in the section 2 or 3, the reagent for derivatization described in the section 5, or the reagent kit for derivatization described in the section 6.

The compound to be analyzed by mass spectrometry may be the target compound described in the section 2.

The derivatized compound to be analyzed by mass spectrometry may be the phosphonium compound described in the section 4.

The derivatization can improve the ionization efficiency of a compound to be analyzed by mass spectrometry, and this can improve the detection sensitivity in mass spectrometry.

The mass spectrometric method comprises, after the derivatization step, a mass spectrometry step comprising ionizing a compound to be analyzed by mass spectrometry.

The ionization may, for example, be ionization by electrospray ionization (ESI), atmospheric pressure chemical ionization (APCI), or matrix-assisted laser desorption-ionization (MALDI), for more efficient ionization, but may be any ionization other than these methods.

By ionizing a target compound derivatized according to the present invention by such an ionization method, the target compound can be quantitatively determined, and the distribution (imaging) of the target compound in a tissue or in cells can be more accurately measured or observed at higher resolution.

The mass spectrometry step may be carried out, for example, by using a liquid chromatography tandem mass spectrometry (LC-MS/MS) or a matrix-assisted laser desorption-ionization mass spectrometry (MALDI-MS), but the apparatus for carrying out the mass spectrometry step is not limited to them.

The specific procedure in the mass spectrometry step may be appropriately designed by a person skilled in the art, for example, depending on a used ionization method and a used apparatus.

8. Seventh Embodiment (Method for Producing Phosphonium Compound)

The present invention further provides a method for producing the phosphonium compound of Formula (I) described in the section 2 or 3 above.

When X in Formula (I) is a reactive group having a hydrazide group, the production method comprises a first reaction step of reacting a phosphine compound below:

[Chemical Formula 28]

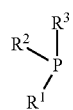

with a halogenated ethyl carboxylate below:

[Chemical Formula 29]

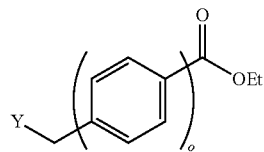

to form a compound below:

[Chemical Formula 30]

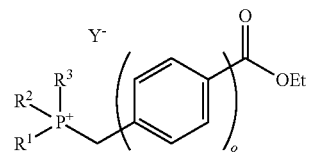

and a second reaction step of reacting the compound formed in the first reaction step with hydrazine to form the phosphonium compound.

In the phosphine compound used in the first reaction step, $R^1$, $R^2$, and $R^3$ may be as described in the section 2.

Y in the halogenated ethyl carboxylate used in the first reaction step may also be Y as described in the section 2.

When X in Formula (I) is a reactive group having a thioester group, the production method comprises reacting a phosphonium acetic acid below:

[Chemical Formula 31]

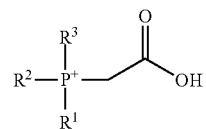

with a thiol below:

[Chemical Formula 32]

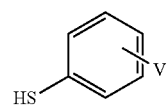

to form the phosphonium compound.

$R^1$, $R^2$, and $R^3$ in the phosphonium acetic acid may be as described in the section 2.

V in the thiol may also be V as described in the section 2.

EXAMPLES

9. Examples

The present invention will next be described in more detail with reference to examples, but the present invention is not limited to these examples.

Example 1

Synthesis of Phosphonium Compound having Hydrazide Group ((2-Hydrazinyl-2-Oxoethyl)Trimethylphosphonium Bromide)

Ethyl bromoacetate (64 µL, 0.6 mmol) was dissolved in 2 mL of acetonitrile, and a trimethylphosphine-tetrahydrofuran solution (3 M, 0.24 mL, trimethylphosphine amount: 0.72 mmol) was added to prepare a mixture. Immediately after the addition, a white precipitate was appeared in the mixture. After the mixture was stirred at room temperature for 1 hour, methanol was added to the mixture to dissolve the precipitate, and the solution was concentrated by using a rotary evaporator. The residue formed by the concentration was dissolved in 2 mL of ethanol, and hydrazine monohydrate (a purity of 80%, 59 µL, 0.96 mmol) was added to the solution. The mixture was stirred at room temperature for 1 hour and further stirred at 50° C. for 1.5 hours. After the stirring, the mixture was concentrated by using a rotary evaporator to yield a reaction product ((2-hydrazinyl-2-oxoethyl)trimethylphosphonium bromide, hereinafter also referred to as "compound 1") (139 mg, 0.6 mmol).

The compound 1 was subjected to $^1$H-NMR measurement, $^{13}$C-NMR measurement, $^{31}$P-NMR measurement, and mass spectrometry. The measurement results are as shown below. $^1$H-NMR (CD$_3$OD) δ 3.56 (d, $^2J_{PH}$=15.0 Hz, 2H), 2.07 (d, $^2J_{PH}$=12.0 Hz, 9H) (A in FIG. 1-1); $^{13}$C-NMR (CD$_3$OD) δ 165.9, 31.5, 9.8 (B in FIG. 1-1); $^{31}$P-NMR (CD$_3$OD) δ 31.1 (C in FIG. 1-2); ESI-MS calculated for C$_5$H$_{14}$N$_2$OP$^+$[M$^+$] 149.08383, found 149 (D in FIG. 1-2).

The structure of the compound 1 is as shown by sign 1 in FIG. 10.

Example 2

Synthesis of Phosphonium Compound having Hydrazide Group ((4-(Hydrazinecarbonyl)Benzyl)Trimethylphosphonium Bromide)

In 8 mL of acetonitrile, 4-methoxycarbonylbenzyl bromide (1 g, 4.4 mmol) was dissolved, and a trimethylphosphine-tetrahydrofuran solution (3 M, 1.7 mL, trimethylphosphine amount: 5.2 mmol) was added. The mixture was stirred at room temperature. After the stirring for 1.5 hours, a white precipitate was appeared. The precipitate was filtered, and the white solid was washed with chloroform and was dried to yield (4-(methoxycarbonyl)benzyl)trimethylphosphonium bromide (1.5 g, 4.4 mmol).

In 2 mL of methanol, (4-(methoxycarbonyl)benzyl)trimethylphosphonium bromide (115 mg, 0.37 mmol) was dissolved, and hydrazine monohydrate (a purity of 80%, 27 µL, 0.45 mmol) was added. The mixture was stirred on ice for 30 minutes and then was concentrated by using a rotary evaporator to yield a reaction product (((4-(hydrazinecarbonyl)benzyl)trimethylphosphonium bromide), hereinafter also referred to as "compound 2") (114 mg, 0.37 mmol).

The compound 2 was subjected to $^1$H-NMR measurement, $^{13}$C-NMR measurement, $^{31}$P-NMR measurement, and mass spectrometry. The measurement results are as shown below. $^1$H-NMR (CD$_3$OD) δ 8.04 (d, J=7.6 Hz, 2H), 7.53 (d, J=7.6 Hz, 2H), 3.98 (d, $^2J_{PH}$=16.8 Hz, 2H), 1.93 (d, $^2J_{PH}$=14.8 Hz, 9H) (A in FIG. 2-1); $^{13}$C-NMR (CD$_3$OD) δ 168.6, 136.4, 135.0, 132.2, 130.6, 53.6, 8.7 (B in FIG. 2-1); $^{31}$P-NMR (CD$_3$OD) δ 28.0 (C in FIG. 2-2); ESI-MS calculated for C$_{11}$H$_{18}$N$_2$OP$^+$[M$^+$] 225.11513, found 225 (D in FIG. 2-2).

The structure of the compound 2 is as shown by sign 2 in FIG. 10.

Example 3

Synthesis of Phosphonium Compound having Hydrazide Group (Benzyl(2-Hydrazinyl Oxoethyl)Dimethylphosphonium Bromide)

Dimethylphenylphosphine (103 µL, 0.72 mmol) and ethyl bromoacetate (76 µL, 0.72 mmol) was added to 1 mL of toluene, and the mixed liquid of them was clouded. To the liquid, 1 mL of acetonitrile was further added, and a white precipitate was immediately appeared. To the liquid, 1 mL of methanol was further added, and the precipitate was immediately dissolved. After the dissolving, the solution was stirred at room temperature for 1.5 hours and then was concentrated by using a rotary evaporator. The resultant residue after the concentration was dissolved in 3 mL of ethanol, and hydrazine monohydrate (a purity of 80%, 71 µL, 1.1 mmol) was added. The mixture was stirred at room temperature for 1 hour and then was concentrated by using a rotary evaporator to yield a reaction product (benzyl(2-hydrazinyl-2-oxoethyl)dimethylphosphonium bromide, hereinafter also referred to as "compound 3") (99 mg, 0.69 mmol).

The compound 3 was subjected to $^1$H-NMR measurement, $^{13}$C-NMR measurement, $^{31}$P-NMR measurement, and mass spectrometry. The measurement results are as shown below. $^1$H-NMR (CDCl$_3$) δ 7.68 (br. s, 2H), 7.47 (br. s, 3H), 3.40 (br. s, 2H), 1.69 (d, $^2J_{PH}$=13.2 Hz, 6H) (A in FIG. 3-1); $^{13}$C-NMR (CDCl$_3$) δ 170.8, 135.0, 134.0, 131.6, 129.5, 128.7, 50.3, 17.9 (B in FIG. 3-1); $^{31}$P-NMR (CDCl$_3$) δ 35.1 (C in FIG. 3-2); ESI-MS calculated for C$_{11}$H$_{18}$N$_2$OP$^+$[M$^+$] 225.11513, found 225 (D in FIG. 3-2).

The structure of the compound 3 is as shown by sign 3 in FIG. 10.

Example 4

Synthesis of Phosphonium Compound having Hydrazide Group ((2-Hydrazinyl-2-Oxoethyl)Triethylphosphonium Bromide)

Ethyl bromoacetate (64 µL, 0.6 mmol) was dissolved in 1 mL of acetonitrile, and a triethylphosphine-tetrahydrofuran solution (1 M, 1 mL, triethylphosphine amount: 1 mmol) was slowly added to the prepared solution. The mixture was stirred at room temperature for 30 minutes and then was concentrated by using a rotary evaporator. The resultant residue after the concentration was dissolved in 2 mL of ethanol, and hydrazine monohydrate (a purity of 80%, 59 µL, 0.96 mmol) was added. The mixture was heated and refluxed for 1 hour. After the heating and refluxing, the mixture was concentrated by using a rotary evaporator to give a reaction product ((2-hydrazinyl-2-oxoethyl)triethylphosphonium bromide, hereinafter also referred to as "compound 4") (139 mg, 0.51 mmol).

The compound 4 was subjected to $^1$H-NMR measurement, $^{13}$C-NMR measurement, $^{31}$P-NMR measurement, and mass spectrometry. The measurement results are as shown below. $^1$H-NMR (CDCl$_3$) δ 3.93 (d, $^2J_{PH}$=14.4 Hz, 6H), 2.45 (dq, $^2J_{PH}$=13.2 Hz, J=7.2 Hz, 6H), 1.30 (dt, $^3J_{PH}$=18.8 Hz, J=7.6 Hz, 9H) (A in FIG. 4-1); $^{13}$C-NMR (CDCl$_3$) δ 162.8, 50.6, 12.9, 5.9 (B in FIG. 4-1); $^{31}$P-NMR (CDCl$_3$) δ 38.9 (C in FIG. 4-2); ESI-MS calculated for C$_8$H$_{20}$N$_2$OP$^+$[M$^+$] 191.13078, found 191 (D in FIG. 4-2).

The structure of the compound 4 is as shown by sign 4 in FIG. 10.

Example 5

Synthesis of Phosphonium Compound having Hydrazide Group (Benzyl(2-Hydrazinyl-2-Oxoethyl)Diethylphosphonium Bromide)

Diethylphenylphosphine (105 µL, 0.6 mmol) and ethyl bromoacetate (64 µL, 0.6 mmol) were added to 2 mL of acetonitrile, and the resulting solution was stirred at room temperature for 1 hour. The solution was concentrated by using a rotary evaporator, and the resultant residue after the concentration was dissolved in 2 mL of toluene. To the resulting solution, hydrazine monohydrate (a purity of 80%, 59 µL, 1.2 mmol) was added, and the mixture was heated and refluxed for 4.5 hours. After the heating and refluxing, the mixture was concentrated by using a rotary evaporator to yield a reaction product (benzyl(2-hydrazinyl oxoethyl)diethylphosphonium bromide, hereinafter also referred to as "compound 5") (195 mg, 0.6 mmol).

The compound 5 was subjected to $^1$H-NMR measurement, $^{13}$C-NMR measurement, $^{31}$P-NMR measurement, and mass spectrometry. The measurement results are as shown below. $^1$H-NMR (CDCl$_3$) δ 10.16 (br. s, 1H), 7.95 (m, 2H), 7.57 (m, 3H), 6.77 (br. s, 2H), 4.23 (d, $^2J_{PH}$=14.4 Hz, 2H), 2.79 (m, 4H), 1.16 (m, 6H) (A in FIG. 5-1); $^{13}$C-NMR (CDCl$_3$) δ 162.5, 134.4, 132.3, 131.3, 130.3, 130.0, 128.4, 22.0, 14.4, 5.6 (B in FIG. 5-1); $^{31}$P-NMR (CDCl$_3$) δ 33.3 (C in FIG. 5-2); ESI-MS calculated for C$_{12}$H$_{20}$N$_2$OP$^+$[M$^+$] 239.13078, found 239 (D in FIG. 5-2).

The structure of the compound 5 is as shown by sign 5 in FIG. 10.

Example 6

Synthesis of Phosphonium Compound having Hydrazide Group ((2-Hydrazinyl-2-Oxoethyl)Triphenylphosphonium Bromide)

Triphenylphosphine (91 mg, 0.35 mmol) was dissolved in 2 mL of toluene to prepare a solution, and ethyl bromoacetate (41 µL, 0.38 mmol) was slowly added to the solution. The mixture was stirred at room temperature for 30 minutes. After the stirring, the mixture was heated and refluxed for 1 hour, and a white precipitate was appeared. After the precipitation, the mixture was concentrated by using a rotary evaporator, and then the resultant residue after the concentration was dissolved in 2 mL of ethanol to give a solution. To the solution, hydrazine monohydrate (a purity of 80%, 21 µL, 0.28 mmol) was added, and the mixture was heated and refluxed for 1 hour. After the heating and refluxing, the solution was concentrated by using a rotary evaporator to yield a reaction product ((2-hydrazinyl-2-oxoethyl)triphenylphosphonium bromide, hereinafter also referred to as "compound 6") (140 mg, 0.34 mmol).

The compound 6 was subjected to $^1$H-NMR measurement, $^{13}$C-NMR measurement, $^{31}$P-NMR measurement, and mass spectrometry. The measurement results are as shown below. $^1$H-NMR (CDCl$_3$) δ 10.36 (br. s, 1H), 7.6 (m, 15H), 5.01 (d, $^2J_{PH}$=14.0 Hz, 2H) (A in FIG. 6-1); $^{13}$C-NMR (CDCl$_3$) δ 161.6, 135.1, 134.0, 132.9, 132.0, 130.2, 128.5, 50.6 (B in FIG. 6-1); $^{31}$P-NMR (CDCl$_3$) δ 30.0 (C in FIG. 6-2); ESI-MS calculated for C$_{20}$H$_{20}$N$_2$O$_1$$^{3+}$[M$^+$] 335.13078, found 335 (D in FIG. 6-2).

The structure of the compound 6 is as shown by sign 6 in FIG. 10.

Example 7

Synthesis of Phosphonium Compound having Hydrazide Group (Tributyl(4-(Hydrazinecarbonyl)Benzyl)Phosphonium Bromide)

In 2 mL of acetonitrile, 4-methoxycarbonylbenzyl bromide (100 mg, 0.44 mmol) was dissolved to prepare a solution, and tributylphosphine (123 mL, 0.52 mmol) was added to the solution. The mixture was stirred at room temperature for 1 hour. After the stirring, the solution was concentrated by using a rotary evaporator. The resultant residue after the concentration was dissolved in 3 mL of toluene-acetonitrile (2:1 (v/v)), and hydrazine monohydrate (a purity of 80%, 102 µL, 1.7 mmol) was added. The mixture was heated and refluxed for 1 hour and then was concentrated by using a rotary evaporator to yield a reaction product (tributyl(4-(hydrazinecarbonyl)benzyl)phosphonium bromide, hereinafter also referred to as "compound 7") (206 mg, 0.44 mmol).

The compound 7 was subjected to $^1$H-NMR measurement, $^{13}$C-NMR measurement, $^{31}$P-NMR measurement, and mass spectrometry. The measurement results are as shown below. $^1$H-NMR (CDCl$_3$) δ 7.95 (d, J=8.0 Hz, 2H), 7.56 (dd, J=8.0, 2.4 Hz, 2H), 4.46 (d, $^2J_{PH}$=15.6 Hz, 2H), 3.43 (br. s, 1H), 2.36 (m, 6H), 1.41 (m, 12H), 0.87 (t, J=7.2 Hz, 9H) (A in FIG. 7-1); $^{13}$C-NMR (CDCl$_3$) δ 166.3, 134.1, 134.0, 130.39, 130.37, 130.3, 130.2, 52.3, 27.2, 23.8, 18.7, 13.4 (B in FIG. 7-1); $^{31}$P-NMR (CDCl$_3$) δ 32.5 (C in FIG. 7-2); ESI-MS calculated for C$_{20}$H$_{36}$N$_2$OP+[M$^+$] 351.25598, found 351 (D in FIG. 7-2).

The structure of the compound 7 is as shown by sign 7 in FIG. 10.

Example 8

Synthesis of Phosphonium Compound having Hydrazide Group (Tributyl(2-Hydrazinyl Oxoethyl)Phosphonium Bromide)

Tributylphosphine (118 µL, 0.5 mmol) was dissolved in 2 mL of toluene, and ethyl bromoacetate (55 µL, 0.5 mmol) was slowly added to the resulting solution. After the addition, the solution was heated and refluxed for 1 hour and then was concentrated by using a rotary evaporator. The resultant residue after the concentration was purified by silica gel column chromatography (column size: 1.5 cm in diameter, 5 cm in length; 10% (v/v) methanol-chloroform) to yield tributyl(2-ethoxy-2-oxoethyl)phosphonium bromide (171 mg, 0.46 mmol).

Tributyl(2-ethoxy-2-oxoethyl)phosphonium bromide (151 mg, 0.41 mmol) was dissolved in 2 mL of ethanol, and the resulting solution was stirred on ice. To the solution, hydrazine monohydrate (a purity of 80%, 20 μL, 0.33 mmol) was added, and the mixture was stirred for 30 minutes on ice and was further stirred at room temperature for 40 minutes. To the solution, hydrazine monohydrate (a purity of 80%, 20 μL, 0.33 mmol) was then added, and the mixture was stirred at room temperature for 1 hour and then was heated and refluxed for 15 minutes. After the heating and refluxing, the solution was cooled to room temperature, and then hydrazine monohydrate (a purity of 80%, 20 μL, 0.33 mmol) was further added. The mixture was stirred at room temperature for 1 hour. Subsequently, hydrazine monohydrate (a purity of 80%, 20 μL, 0.33 mmol) was further added to the solution, and the mixture was heated and stirred at 50° C. overnight and then was concentrated by using a rotary evaporator. The resultant residue after the concentration was purified by silica gel column chromatography (column size: 1.5 cm in diameter, 5 cm in length; 10% (v/v) methanol-chloroform) to yield a reaction product (tributyl(2-hydrazinyl-2-oxoethyl)phosphonium bromide, also referred to as "compound 8") (157 mg, 0.41 mmol).

The compound 8 was subjected to $^1$H-NMR measurement, $^{13}$C-NMR measurement, $^{31}$P-NMR measurement, and mass spectrometry. The measurement results are as shown below. $^1$H-NMR (CDCl$_3$) δ 11.0 (br. s, 1H), 4.11 (d, $^2J_{PH}$=14.0 Hz, 2H), 2.30 (m, 8H), 1.45 (m, 12H), 0.88 (m, 9H) (A in FIG. 8-1); $^{13}$C-NMR (CDCl$_3$) δ 159.2, 50.1, 27.1, 23.7, 19.4, 13.4 (B in FIG. 8-1); $^{31}$P-NMR (CDCl$_3$) δ 33.7 (C in FIG. 8-2); ESI-MS calculated for $C_{14}H_{32}N_2OP^+[M^+]$ 275.22468, found 275 (D in FIG. 8-2).

The structure of the compound 8 is as shown by sign 8 in FIG. 10.

Example 9

Synthesis of Phosphonium Compound having Hydrazide Group ((2-Hydrazinyl-2-Oxoethyl)Diphenyl(3-Sulfophenyl)Phosphonium Bromide)

Ethyl bromoacetate (29 μL, 0.27 mmol) was dissolved in 1 mL of toluene. To the solution, sodium diphenylphosphinobenzene-3-sulfonate (100 mg, 0.27 mmol) was added, and subsequently 1 mL of acetonitrile was added to prepare a suspension. To the suspension, 1 mL of methanol was added to completely dissolve the suspension, and the resulting solution was heated and refluxed for 1 hour. After the heating and refluxing, the solution was concentrated by using a rotary evaporator, and then the resultant residue after the concentration was dissolved in 3 mL of ethanol to prepare a solution. To the solution, hydrazine monohydrate (80%, 27 μL, 0.44 mmol) was added, and the mixture was heated and refluxed for 2 hours. After the heating and refluxing, hydrazine monohydrate (a purity of 80%, 27 μL, 0.44 mmol) was further added to the solution. The mixture was heated and refluxed for 2 hours and then was concentrated by using a rotary evaporator to yield a reaction product ((2-hydrazinyl-2-oxoethyl)diphenyl(3-sulfophenyl) phosphonium bromide, hereinafter also referred to as "compound 9") (122 mg, 0.25 mmol).

The compound 9 was subjected to $^1$H-NMR measurement, $^{13}$C-NMR measurement, $^{31}$P-NMR measurement, and mass spectrometry. The measurement results are as shown below. $^1$H-NMR (CD$_3$OD) δ 8.18 (ddd, J=12.0, 1.2, 1.2 Hz, 2H), 8.10 (ddd, J=12, 1.2, 1.2 Hz, 2H), 7.64 (m, 8H), 7.55 (m, 4H) (A in FIG. 9-1); $^{13}$C-NMR (CD$_3$OD) δ 173.3, 147.6, 135.4, 134.7, 133.7, 133.6, 130.9, 130.7, 120.3, 119.5, 21.4 (B in FIG. 9-1); $^{31}$P-NMR (CD$_3$OD) δ 32.1 (C in FIG. 9-2); ESI-MS calculated for $C_{20}H_{20}N_2O_4PS^+[Mt]$ 415.08759, found 415 (D in FIG. 9-2).

The structure of the compound 9 is as shown by sign 9 in FIG. 10.

Example 10

Derivatization of testosterone with phosphonium compound having hydrazide group

In a 2-mL microtube, 10 μL of a sample (standard testosterone, a pooled serum extract, or acetonitrile (for background validation)) was placed, and 10 μL of a methanol solution of a phosphonium compound (1 mg/mL) and 50 μL of 10% (v/v) acetic acid/methanol solution were further added to the microtube. The mixture was heated at 50° C. for 45 minutes in a block heater. Accordingly, testosterone was derivatized with the phosphonium compound. The above derivatization treatment was carried out by using each of the compounds 1 to 9 prepared in Examples 1 to 9. The testosterone derivatives prepared by the derivatization reaction with the compounds 1 to 9 are also referred to as derivatives D1 to D9, respectively.

The reaction formula of derivatization of testosterone with the phosphonium compound having a hydrazide group is shown in FIG. 11. As shown in the figure, testosterone is derivatized with the phosphonium compound of Formula (I). The chemical structures of the derivatives D1 to D9 are shown in FIG. 12. In FIG. 12, the upper part shows the testosterone moiety of the derivatives. The lower part shows moieties bonded to testosterone by derivatization.

As reference substances, Girard's reagents T and P (FIG. 13 shows the structures of these reagents) were used for a similar derivatization treatment. Testosterone derivatives prepared by derivatization treatment with the Girard's reagents T and P are also referred to as derivatives DT and DP, respectively. The structures of the derivatives DT and DP are also shown in FIG. 12.

The solution after heating in the block heater was centrifugally concentrated, and the product prepared by the centrifugal concentration was redissolved in 100 μL of 50% (v/v) aqueous acetonitrile solution. Next, 10 μL of the solution prepared by redissolution was used for LC-MS/MS analysis as described in Example 11.

Example 11

LC-MS/MS Analysis of Testosterone Derivatives

Under the following LC analysis conditions and the MS/MS analysis conditions, the testosterone derivatives (derivatives D1 to D9 and derivatives DT and DP) prepared by the derivatization reaction described in Example 10 were subjected to LC-MS/MS analysis. Testosterone without derivatization treatment was also subjected to LC-MS/MS analysis under substantially the same conditions.

<LC Analysis Conditions>

Apparatus: high-speed liquid chromatograph LC-20A (Shimadzu Corporation)

Analytical column: YMC Triart C$_{18}$ (column size: 2.1 mm in inner diameter, 100 mm in length; YMC)

Elution conditions: flow rate, 0.3 mL/min; solvent A, 0.1% (v/v) formic acid-water; solvent B, methanol

TABLE 1

Elution conditions

| Time (min) | | | | | |
|---|---|---|---|---|---|
| 0 | 3 | 5 | 6 | 6.01 | 8 |
| B (%) | | | | | |
| 30 | 70 | 90 | 90 | 30 | 30 |

<MS/MS Analysis Conditions>
Apparatus: liquid chromatograph-mass spectrometer (LCMS8040 triple-quadrupole mass spectrometer, Shimadzu Corporation)
Ionization conditions: ESI positive ion mode
SRM parameter (as shown in Table 2)
SRM chromatograms in analysis of the derivatives D1 to D9 and the derivatives DT and DP (100 pg of testosterone) are shown in FIG. 14-1 to FIG. 14-6.

TABLE 2

SRM parameter

| Testosterone derivative | m/z | CE |
|---|---|---|
| Derivative D1 | 419.2 > 303.2 | 32 |
| Derivative D2 | 495.4 > 192.05 | 47 |
| Derivative D3 | 481.3 > 303.2 | 38 |
| Derivative D4 | 461.3 > 303.2 | 36 |
| Derivative D5 | 509.4 > 303.2 | 37 |
| Derivative D6 | 605.2 > 303.1 | 42 |
| Derivative D7 | 621.5 > 318.2 | 53 |
| Derivative D8 | 545.3 > 243.1 | 42 |
| Derivative D9 | 685.3 > 383 | 45 |
| Derivative DT | 402 > 343.2 | 32 |
| Derivative DP | 422 > 343.2 | 29 |
| Not derivatized | 289.2 > 97.05 | 22 |

<Analytical Results>
FIG. 15-1 shows the analytical results of the background, the standard testosterone (10 pg of testosterone), and the pooled serum extract. In the figure, the vertical axis represents peak area value. Table 3 shows measured peak area values.

TABLE 3

Peak area value

| | Background | Testosterone (10 pg) | Pooled serum |
|---|---|---|---|
| Compound 1 | 9567 | 86573 | 91654 |
| Compound 2 | 471 | 15744 | 6583 |
| Compound 3 | 26969 | 329048 | 599732 |
| Compound 4 | 178409 | 2201141 | 367873 |
| Compound 5 | 87200 | 453642 | 671056 |
| Compound 6 | 45556 | 347278 | 654827 |
| Compound 7 | 1700 | 9799 | 45258 |
| Compound 8 | 2233193 | 2803681 | 3472905 |
| Compound 9 | 11894 | 59783 | 127440 |
| Reagent T | 8039 | 77320 | 108853 |
| Reagent P | 10765 | 130324 | 125519 |
| Not derivatized | 39215 | 41341 | 93564 |

From the analytical results, the compounds 1 to 9 each gave higher peak areas of the standard testosterone and the pooled serum than the peak area of the background. This reveals that the derivatization treatment with the compounds 1 to 9 enables appropriate detection of testosterone.

The analytical results also reveal that the testosterone derivatives with the compounds 1 to 9 were detected at substantially the same sensitivity as or higher sensitivity than those with the conventionally used reagents T and P.

When not derivatized, 10 pg of testosterone gave a peak area value that was almost equal to the peak area value of the background. This reveals that testosterone not derivatized is not appropriately detected. In consideration of these results, testosterone derivatized in accordance with the present invention can be detected at higher sensitivity than that not derivatized.

In the above analysis, standard samples containing 10 pg of testosterone were analyzed. Samples containing a smaller amount of testosterone were similarly analyzed. The analytical results are shown in FIG. 15-2. Table 4 shows observed peak area values. The amounts of testosterone in standard samples to be analyzed were 100 fg and 1 pg as shown in the figure.

As shown by the results, each compound according to the present invention enables detection of 1 pg of testosterone at good sensitivity.

When containing 100 fg of testosterone, a sample not derivatized gave almost the same peak area value as that of the background and was undetectable, but a sample derivatized with the compound 1, 3, or 4 according to the present invention gave a peak area value that sufficiently differed from that of the background. In other words, these compounds enable detection of 100 fg of testosterone at good sensitivity.

When containing 100 fg of testosterone, a sample derivatized with Girard's reagent P and a sample not derivatized gave almost the same peak area values as the area value of the background, and this indicates that these samples cannot be quantitatively determined. In contrast, a sample containing 100 fg of testosterone and derivatized with the compound according to the present invention gave a higher peak area value than the area value of the background.

Comparison between the sample containing 100 fg of testosterone and derivatized with the reagent T and the sample containing 100 fg of testosterone and derivatized with the compound 4 reveals that the compound according to the present invention can increase the sensitivity by a factor of about 2 as compared with the Girard's reagent T.

TABLE 4

Peak area value

| | Background | Testosterone (100 fg) | Testosterone (1 pg) |
|---|---|---|---|
| Compound 1 | 852 | 2137 | 8183 |
| Compound 3 | 1567 | 3074 | 5750 |
| Compound 4 | 1492 | 6903 | 29530 |
| Compound 5 | 1243 | 1701 | 5612 |
| Reagent T | 2156 | 3800 | 10377 |
| Reagent P | 5689 | 5681 | 16456 |
| Not derivatized | 4832 | 6603 | 13586 |

Example 12

Derivatization of Estradiol (11) with 4-Bromomethylbenzenesulfonyl Chloride and Trimethylphosphine (Synthesis of Estradiol-3-(4-Trimethylphosphoniummethyl)Benzenesulfonate)

In a 30-mL recovery flask, estradiol (100 mg, 0.37 mmol) and 4-bromomethylbenzenesulfonyl chloride (99 mg, 0.37 mmol) were placed, and 3 mL of acetone was added. The mixture was dissolved and stirred at room temperature. Sodium hydrogen carbonate (46 mg, 0.55 mmol) was dissolved in 1 mL of water to prepare an aqueous solution. The aqueous solution was added dropwise to the reaction mixture in the recovery flask, and the mixture was stirred at 60° C. for 24 hours. After the stirring, the reaction mixture was cooled to room temperature and was diluted with 4 mL of ethyl acetate. The mixture was washed with 2 mL of brine and then was concentrated by using a rotary evaporator. The resultant residue after the concentration was purified by silica gel column chromatography (column size: 1.5 cm×10 cm; 50% (v/v) ethyl acetate-hexane), and the purified fraction was concentrated by using a rotary evaporator. After the concentration, the residue was dried under reduced pressure to yield estradiol-3-(4-bromomethyl)benzenesulfonate (hereinafter also referred to as "reaction intermediate 1") (79 mg, 0.16 mmol). The structures of estradiol and the reaction intermediate 1 are shown at the left part and the center part, respectively, in FIG. 16.

The reaction intermediate 1 was subjected to $^1$H-NMR measurement, $^{13}$C-NMR measurement, and mass spectrometry. The measurement results are as shown below.

$^1$H-NMR (CDCl$_3$) δ 7.81 (d, J=8.8 Hz, 2H), 7.5 (d, J=8.8 Hz, 2H), 7.14 (d, J=8.8 Hz, 1H), 6.69 (s, 1H), 6.68 (d, J=8.8 Hz, 1H), 4.60 (s, 2H), 4.47 (s, 1H), 3.69 (t, J=8.0 Hz, 1H), 2.73 (m, 2H), 2.24 (m, 1H), 2.14 (m, 1H), 2.07 (m, 1H), 1.91 (dt, J=12.1, 3.4 Hz, 1H), 1.83 (m, 1H), 1.65 (m, 1H), 1.34 (m, 8H), 0.74 (s, 3H) (A in FIG. 17); $^{13}$C-NMR (CDCl$_3$) δ 147.1, 143.7, 139.5, 138.7, 135.4, 129.5, 129.0, 128.9, 128.8, 126.5, 122.1, 118.9, 81.6, 49.9, 44.6, 44.0, 43.1, 38.2, 36.5, 30.4, 29.3, 26.8, 26.0, 23.0, 11.0 (B in FIG. 17).

The reaction intermediate 1 was placed in a 30-mL recovery flask, and 2 mL of acetone was added to dissolve the intermediate. The solution was stirred at room temperature. To the solution in the recovery flask, a trimethylphosphine-tetrahydrofuran solution (3 M, 1 mL, trimethylphosphine amount: 3 mmol) was added dropwise. The mixture was stirred at room temperature for 5 minutes and was further stirred at 60° C. for 5 minutes while heated in an oil bath. Accordingly, a white precipitate was appeared. The solution containing the precipitate was concentrated by using a rotary evaporator, and the residue was dried under vacuum to yield a reaction product (estradiol-3-(4-trimethylphosphoniummethyl)benzenesulfonate, hereinafter also referred to as "derivative D11") (90 mg, 0.16 mmol). The structure of the derivative D11 is shown at the right part in FIG. 17.

The derivative D11 was subjected to $^1$H-NMR measurement, $^{13}$C-NMR measurement, $^{31}$P-NMR measurement, and mass spectrometry. The measurement results are as shown below.

$^1$H-NMR (CD$_3$OD) δ 7.87 (d, J=8.0 Hz, 2H), 7.63 (dd, J=8.0 Hz, $^4J_{PH}$=1.4 Hz, 2H), 7.18 (d, J=9.2 Hz, 1H), 6.69 (d, J=9.2 Hz, 1H), 6.68 (s, 1H), 3.97 (d, $^2J_{PH}$=16.8 Hz, 2H), 3.69 (t, J=8.8 Hz, 1H), 2.70 (m, 2H), 2.24 (br. d, J=13.2 Hz, 1H), 2.11 (m, 1H), 2.00 (m, 1H), 1.92 (m, 1H), 1.91 (d, $^2J_{PH}$=16.8 Hz, 6H), 1.83 (m, 1H), 1.65 (m, 1H), 1.55 (d, $^2J_{PH}$=16.8 Hz, 3H), 1.31 (m, 8H) (A in FIG. 18-1); $^{13}$C-NMR (CD$_3$OD) δ 149.4, 141.8, 140.8, 138.3, 137.5, 133.0, 131.4, 131.3, 130.8, 128.6, 124.0, 121.0, 83.1, 52.0, 46.2, 45.1, 40.6, 38.6, 31.5, 28.8, 28.1, 24.8, 18.3, 17.6, 12.5, 8.60 (B in FIG. 18-1); $^{31}$P-NMR (CD$_3$OD) δ 28.5 (C in FIG. 18-2); ESI-MS calculated for $C_{28}H_{38}O_4PS^+[M^+]$ 501.22229, found 501 (D in FIG. 18-2).

Example 13

Derivatization of Estradiol with 4-(Bromomethyl)Benzenesulfonyl Chloride and Various Phosphines In a 2-mL microtube, 10 μL of a sample (standard estradiol or acetonitrile (for background validation)) was placed, and 50 μL of a 4-(bromomethyl)benzenesulfonyl chloride-acetone solution (1 mg/mL) and 50 μL of an aqueous sodium hydrogen carbonate solution (100 mM) were added. The mixture was heated at 60° C. for 5 minutes in a block heater. After the heating, to the sample in the microtube, 50 μL of 1% (v/v) phosphine-acetonitrile solution was added, and the mixture was further heated at 60° C. for 2 minutes in a block heater. Accordingly, an estradiol derivative was formed. As the phosphine, not only the trimethylphosphine used in Example 12 but also other seven phosphines were used. Accordingly, eight estradiol derivatives (also referred to as derivatives D11 to D18) were formed.

The structures of the formed derivatives are shown in FIG. 19. The upper part in the figure shows the structure common to these derivatives. The lower part in the figure shows structures derived from used phosphines.

After the heating, centrifugal concentration was carried out, and the product of the centrifugal concentration was redissolved in 100 μL of 50% (v/v) aqueous acetonitrile solution. Next, 10 μL of the solution prepared by redissolution was used for LC-MS/MS analysis.

Comparative Example 14

Derivatization of Estradiol with Dansyl Chloride

In a 2-mL microtube, 10 μL of a sample (standard estradiol or acetonitrile (for background validation) was placed, and 50 μL of a dansyl chloride-acetone solution (1 mg/mL) and 50 μL of an aqueous sodium hydrogen carbonate solution (100 mM) were added. The mixture was heated at 60° C. for 5 minutes in a block heater. After the heating, centrifugal concentration was carried out, and the product of the centrifugal concentration was redissolved in 100 μL of 50% (v/v) aqueous acetonitrile solution. Next, 10 μL of the solution prepared by redissolution was used for LC-MS/MS analysis (the structure of the formed derivative is shown in FIG. 20; the derivative is also referred to as DD). The dansyl derivative is a reference substance.

Example 15

Derivatization of Estradiol with Bromoacetyl Bromide and Various Phosphines

In a 2-mL microtube, 10 μL of a sample (standard estradiol or acetonitrile (for background validation)) was placed, and 50 μL of a bromoacetyl bromide-acetone solution (1 mg/mL) and 50 μL of a triethylamine-acetonitrile solution (100 mM) were added. The mixture was heated at 60° C. for 5 minutes in a block heater. To the sample in the microtube after the heating, 50 μL of 1% (v/v) phosphine-acetonitrile solution was added, and the mixture was further heated at 60° C. for 2 minutes in a block heater. As the phosphine, not only trimethylphosphine but also other three phosphines were used. Accordingly, four estradiol derivatives (also referred to as derivatives D21 to D24) were formed.

The structures of the formed derivatives are shown in FIG. 21. The left part in the figure shows the structure common to these derivatives. The right part in the figure shows structures derived from used phosphines.

After the heating in the block heater, centrifugal concentration was carried out, and the product of the centrifugal concentration was redissolved in 100 μL of 50% (v/v)

aqueous acetonitrile solution. Next, 10 μL of the solution prepared by redissolution was used for LC-MS/MS analysis Example 16

LC-MS/MS Analysis of Estradiol Derivatives

Under the following LC analysis conditions and the MS/MS analysis conditions, the LC-MS/MS analyses described in Example 13, Comparative Example 14, and Example 15 were carried out.

<LC Analysis Conditions>

Apparatus: high-speed liquid chromatograph LC-20A (Shimadzu Corporation)

Analytical column: YMC Triart C18 (column size: 2.1 mm in inner diameter, 100 mm in length; YMC)

Elution conditions: flow rate, 0.3 mL/min; solvent A, 0.1% (v/v) formic acid-water; solvent B, methanol

TABLE 5

| Elution conditions | | | | | |
|---|---|---|---|---|---|
| | Time (min) | | | | |
| | 0 | 4 | 6 | 6.01 | 8 |
| B (%) | 30 | 100 | 100 | 30 | 30 |

<MS/MS Analysis Conditions>

Apparatus: liquid chromatograph-mass spectrometer (LCMS8040 triple-quadrupole mass spectrometer, Shimadzu Corporation)

Ionization conditions: ESI positive ion mode

SRM parameter (as shown in Table 6)

TABLE 6

| SRM parameter | | |
|---|---|---|
| Estradiol derivative | m/z | CE |
| Derivative 11 | 501 > 166 | 39 |
| Derivative 12 | 543 > 208 | 43 |
| Derivative 13 | 563.2 > 228 | 43 |
| Derivative 14 | 591.2 > 256.1 | 43 |
| Derivative 15 | 625.2 > 290.1 | 42 |
| Derivative 16 | 687.1 > 352.1 | 44 |
| Derivative 17 | 627.3 > 292.25 | 42 |
| Derivative 18 | 705.2 > 370.2 | 52 |
| Derivative DD (Comparative Example) | 506.1 > 171.1 | 36 |
| Derivative 21 | 389.3 > 135 | 27 |
| Derivative 22 | 431.3 > 177.1 | 29 |
| Derivative 23 | 451.2 > 197 | 30 |
| Derivative 24 | 479.2 > 225 | 31 |

SRM chromatograms of the derivatives (10 pg of estradiol as derivatives 11 to 18 and derivative DD; 10 ng of estradiol as derivatives 21 to 24) are shown in FIG. 22-1 to FIG. 22-7.

<Analytical Results>

FIG. 23 shows the analytical results of the background and the standard estradiol (10 pg of estradiol) as the derivatives 11 to 18 and the derivative DD. In the figure, the vertical axis represents peak area value. Table 7 shows observed peak area values.

TABLE 7

| | Peak area value | |
|---|---|---|
| | Background | Estradiol (10 pg) |
| Derivative D11 | 1420.4 | 562978.2 |
| Derivative D12 | 1982.4 | 609921.6 |
| Derivative D13 | 1554.6 | 853326.6 |
| Derivative D14 | 1554.6 | 623490.8 |
| Derivative D15 | 1096.6 | 162323 |
| Derivative D16 | 2952.8 | 379958.6 |
| Derivative D17 | 368.2 | 129077.4 |
| Derivative D18 | 5714 | 108640.6 |
| Derivative DD | 644.6 | 232395.2 |

From the analytical results, the standard estradiol as each of the derivatives 11 to 18 according to the present invention gave a much higher peak area than the peak area of the background. This indicates that the derivatization of estradiol according to the present invention enables appropriate detection of estradiol.

The analytical results also reveal that estradiol derivatives as the derivatives 11 to 18 were detected at substantially the same sensitivity as or higher sensitivity than the conventional derivative DD (dansyl derivative).

In the above analysis, a standard sample containing 10 pg of estradiol was analyzed. Samples containing a smaller amount of estradiol were similarly analyzed.

The analytical results are shown in FIG. 24. Table 8 shows measured peak area values. The amount of estradiol in the standard sample to be analyzed was 10 fg or 100 fg as shown in the figure.

TABLE 8

| | Peak area value | | |
|---|---|---|---|
| | Background | Estradiol (10 fg) | Estradiol (100 fg) |
| Derivative D11 | 105.6 | 2003 | 5493.8 |
| Derivative D12 | 227.4 | 1806.6 | 5277.8 |
| Derivative D13 | 205.75 | 3843 | 7110 |
| Derivative D14 | 101.4 | 1244.6 | 4412 |
| Derivative D16 | 78.2 | 189.8 | 2814.2 |
| Derivative DD | 243.6 | 343.2 | 2402.2 |

From the results shown in the figure, when the amount of estradiol was 100 fg, each derivative gave a much higher peak area value than that of the background. This indicates that even when the amount is 100 fg, which is much lower than 10 pg, estradiol can be detected.

From the analytical results, when the amount of estradiol was 10 fg, the derivative DD (Comparative Example) gave a slightly higher peak area value than the area value of the background. In contrast, when the amount of estradiol was 10 fg, the other derivatives according to the present invention gave much higher peak area values than the area value of the background. These results also indicate that the present invention can improve the sensitivity by a factor of about 10 as compared with a conventional reagent, dansyl chloride.

FIG. 25 shows analytical results of the background and the standard estradiol (10 ng of estradiol) as the derivatives D21 to D24. In the figure, the vertical axis represents peak area value. In the figure, the peak areas of the backgrounds are too small to observe their bars.

From the analytical results, the standard estradiol as each of the derivatives D21 to D24 according to the present invention gave a much higher peak area than the peak area of the background. This indicates that derivatization of estradiol according to the present invention enables appropriate detection of estradiol.

Example 17

Synthesis of Phosphonium Compound Having Thioester Group ((2-(2-(4-((Tributylphosphonio) Acetyl)Thio)Phenyl)Acetamide)Ethane-1-Sulfonate)

Trityl chloride (0.83 g, 3.0 mmol) was dissolved in 3 mL of chloroform, and 4-mercaptophenylacetic acid (500 mg, 3.0 mmol) was added to the prepared solution. The mixture was stirred for 1 hour. To the solution, an aqueous sodium hydroxide solution (1 M, 4.5 mL) was then added to neutralize the solution, and after the neutralization, ethyl acetate was added. After the addition, the solution was washed with brine, and the organic layer was dried over sodium sulfate and then concentrated under reduced pressure to give an oily residue. The resultant residue was purified by silica gel to give 4-(tritylthio)phenylacetic acid (hereinafter also referred to as "trityl product") (0.81 g, 2.0 mmol).

Taurine (0.46 g, 3.7 mmol) and triethylamine (0.51 mL, 3.7 mmol) were dissolved in 15 mL of water, and 24 mL of an N-methylpyrrolidone solution of the trityl product (0.76 g, 1.9 mmol) and 1-hydroxybenzotriazole (0.50 g, 3.7 mmol) was added. To the mixture, 1-ethyl-3-(3-dimethylaminopropyl)carbodiimide hydrochloride (0.39 g, 2.0 mmol) was added, and the whole was stirred for 2 days. The reaction solution was purified by silica gel to give 2-(2-(4-(tritylthio)phenyl)acetamide)ethane-1-sulfonic acid (hereinafter also referred to as "taurine conjugate") (1.2 g, 2.3 mmol).

The taurine conjugate (0.96 g, 1.9 mmol) and triethylsilane (0.32 mL, 2.0 mmol) were dissolved in 14 mL of chloroform, and 4.1 mL of trifluoroacetic acid was added. The mixture was stirred for 30 minutes. The reaction solution was concentrated to give an oily residue, 2-(2-(4-mercaptophenyl)acetamide)ethane-1-sulfonic acid (hereinafter also referred to as "thiol") (1.7 g, 1.9 mmol).

Tributylphosphine (0.52 mL, 2.1 mmol) and tert-butyl bromoacetate (0.29 mL, 2.0 mmol) were dissolved in 10 mL of toluene, and the solution was stirred for 3 hours. The reaction solution was diluted with toluene, washed with water, and then concentrated under reduced pressure. The resultant residue was dissolved in 8.8 mL of 90% (v/v) aqueous trifluoroacetic acid solution, and the solution was stirred for 1.5 hours. The reaction solution was concentrated under reduced pressure to give an oily residue, tributylphosphonium acetic acid (hereinafter also referred to as "carboxylic acid") (0.89 g, 2.0 mmol).

The thiol (0.70 g, 2.5 mmol) and the carboxylic acid (0.19 g, 0.56 mmol) were dissolved in 2 mL of N,N'-dimethylformamide, and diisopropylethylamine (0.14 mL, 0.80 mmol) and 1H-benzotriazol-1-yloxytripyrrolidinophosphonium hexafluorophosphate (0.42 g, 0.80 mmol) were added to the solution. N,N'-Diisopropylethylamine was added to adjust the pH at about 7, and then the mixture was stirred for 2 hours. The reaction solution was diluted with 0.1% (v/v) aqueous trifluoroacetic acid solution, and the solution was purified by reversed-phase HPLC. A fraction containing the target compound was freeze-dried to yield a thioester ((2-(2-(4-((tributylphosphonio)acetyl)thio)phenyl)acetamide) ethane-1-sulfonate, hereinafter also referred to as "compound 31") as a powder (80 mg, 0.15 mmol).

The compound 31 was subjected to $^1$H-NMR measurement and mass spectrometry. The measurement results are as shown below.

$^1$H-NMR (CD$_3$OD) (FIG. 26-1); ESI-MS calculated for $C_{24}H_{41}NO_5PS_2^+$[M+H$^+$] 518.21583, found 518 (FIG. 26-2).

Example 18

Derivatization of Oxytocin by NCL Method

In a TPX 1.5-mL AMR Proteosave Tube, 100 µL of 100 mM phosphate buffer (pH 8.0) was placed. To the buffer, 10 µL of an aqueous solution of acetic acid and acetonitrile containing oxytocin at a concentration of 100 ng/mL (an acetic acid concentration of 1% (v/v), an acetonitrile concentration of 10% (v/v)) was added. Next, to the tube, 5 µL of an aqueous tris(2-carboxyethyl)phosphine (TCEP) solution (100 mg/mL) prepared just before the use and 5 µL of 50% aqueous acetonitrile solution containing the compound 31 at a concentration of 0.2 mg/mL were added, and the mixture was stirred and then reacted for 15 minutes at room temperature. After the reaction, 5 µL of an aqueous MES solution was added, and the mixture was stirred and reacted for 15 minutes for derivatization. The reaction formula of the derivatization is shown in FIG. 27.

Example 19

Aftertreatment and LC-MS/MS Analysis of Oxytocin Derivatives

To remove a large amount of salt contained associated with derivatization and to enable concentration of the derivative, a disk-shaped solid phase of Empore™ 2215-C18 Octadecyl (CDS Analytical) was packed into the leading end of TORAST™-H Tip (Shimadzu Corporation) to prepare a self-made minicolumn for use. Through the minicolumn, 50 µL of acetonitrile was passed, and then 50 µL of an aqueous solution of acetic acid and acetonitrile (an acetic acid concentration of 1% (v/v), an acetonitrile concentration of 10% (v/v)) was passed for equilibrium. The whole sample after derivatization in Example 18 was then loaded. Through the minicolumn, 50 µL of the aqueous solution of acetic acid and acetonitrile was passed to wash the minicolumn, and the sample was eluted with 120 µL of an aqueous solution of acetic acid and acetonitrile (an acetic acid concentration of 0.1% (v/v), an acetonitrile concentration of 50% (v/v)). The eluate was used as a sample for LC-MS/MS analysis. The LC-MS/MS analysis was carried out under the following conditions.

<LC Analysis Conditions>
Apparatus: Agilent 1290 Infinity
Analytical column: Waters ACQUITY UPLC Peptide BEH C18, 2.1 mm×50 mm
Elution conditions: flow rate, 0.5 mL/min; solvent A, 0.05% (v/v) acetic acid-water; solvent B, 0.05% (v/v) acetic acid-acetonitrile
The elution conditions were as shown in Table 9.

TABLE 9

| | Elution conditions | | | | | |
|---|---|---|---|---|---|---|
| | Time (min) | | | | | |
| | 0 | 0.5 | 2.5 | 2.51 | 3.5 | 3.51 | 4.5 |
| B (%) | 10 | 25 | 37 | 90 | 90 | 10 | 10 |

<MS/MS Analysis Conditions>
Apparatus: SCIEX QTRAP 4500
Ionization conditions: ESI positive ion mode
SRM parameters were as shown in Table 10.

TABLE 10

| Compound | SRM parameter | |
| --- | --- | --- |
| | m/z | CE |
| Oxytocin | 1007.2 > 723.1 | 43 |
| Oxytocin derivative | 626.4 > 243.1 | 55 |
| Oxytocin derivative (identified ion) | 626.4 > 285.0 | 21 |

<Analytical Results>

The analytical results are shown in FIGS. 28 and 29. In FIG. 29, the vertical axis represents peak area. From the analytical results, an oxytocin derivatized in accordance with the present invention was detected at an intensity eight times higher than that of oxytocin not derivatized. This indicates that the present invention can improve the detection sensitivity of oxytocin.

The present invention may be configured as follows:

[Clause 1] A phosphonium compound represented by Formula (I):

[Chemical Formula 1]

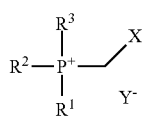

(I)

[in Formula (I), $R^1$, $R^2$, and $R^3$ are independently from each other, an alkyl group or an aryl group, the alkyl group is a substituted or unsubstituted, linear or branched alkyl group having 1 to 20 carbon atoms or a substituted or unsubstituted cyclic alkyl group having 5 to 20 carbon atoms, the aryl group is a substituted or unsubstituted aryl group having 6 to 20 carbon atoms;

X is a reactive group having a hydrazide group, a halide group, a pseudohalide group, or a thioester group; and $Y^-$ is an anion having a total charge of −1, or $Y^-$ is absence].

[Clause 2] The phosphonium compound according to [Clause 1], wherein in Formula (I), the alkyl group is a substituted or unsubstituted, linear or branched alkyl group having 1 to 10 carbon atoms or a substituted or unsubstituted cyclic alkyl group having 5 to 10 carbon atoms, and the aryl group is a substituted or unsubstituted aryl group having 6 to 10 carbon atoms.

[Clause 3] The phosphonium compound according to [Clause 1], wherein in Formula (I), $R^1$, $R^2$, and $R^3$ are independently from each other,

[Chemical Formula 2]

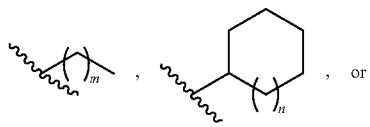

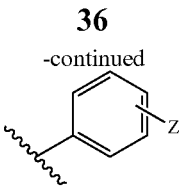

[wherein m is any integer of 0 to 8; n is any integer of 0 to 5; Z is H, $NH_2$, $COO^-$, COOM, $SO_3^-$ (a sulfonate ion group), or $SO_3M$ (a sulfonic acid group or a sulfonate salt group); and M is a hydrogen atom, a lithium atom, a sodium atom, or a potassium atom).

[Clause 4] The phosphonium compound according to any of [Clause 1] to [Clause 3], wherein in Formula (I), when X is a reactive group having a hydrazide group, the reactive group is

[Chemical Formula 3]

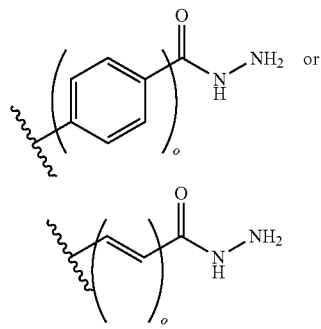

wherein o is any integer of 0 to 6;

when X is a reactive group having a halide group or a pseudohalide group, the reactive group is

[Chemical Formula 4]

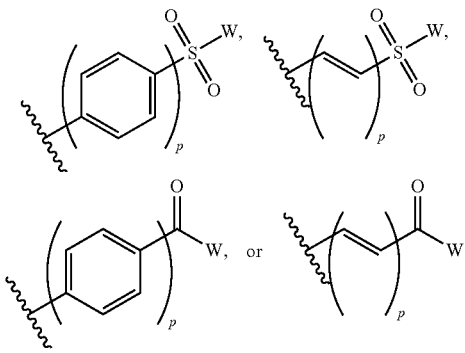

wherein W is a halogen or a pseudohalogen, and p is any integer of 0 to 6; or when X is a reactive group having a thioester group, the reactive group is

[Chemical Formula 5]

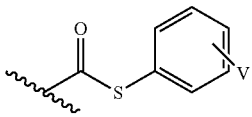

wherein V is H, NH$_2$, SO$_3^-$ (a sulfonate ion group), SO$_3$M, COO$^-$, COOM, or a hydrophilic tag, and M is a hydrogen atom, a lithium atom, a sodium atom, or a potassium atom.
[Clause 5] A phosphonium compound represented by Formula (I):

[Chemical Formula 6]

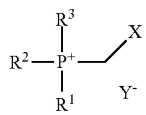
(I)

[in Formula (I),
R$^1$, R$^2$, and R$^3$ are an identical hydrophobic hydrocarbon group or different hydrophobic hydrocarbon groups;
X is a reactive group to react with an oxygen atom-containing functional group or a nitrogen atom-containing functional group; and
Y$^-$ is a counter anion, or Y$^-$ is absence].
[Clause 6] A phosphonium compound represented by Formula (II):

[Chemical Formula 7]

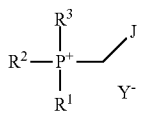
(II)

[in Formula (II),
R$^1$, R$^2$, and R$^3$ are independently from each other, an alkyl group or an aryl group, the alkyl group is a substituted or unsubstituted, linear or branched alkyl group having 1 to 20 carbon atoms or a substituted or unsubstituted cyclic alkyl group having 5 to 20 carbon atoms, the aryl group is a substituted or unsubstituted aryl group having 6 to 20 carbon atoms;
J represents a group formed by reaction of a reactive group having a hydrazide group, a halide group, a pseudohalide group, or a thioester group with a compound to be derivatized; and
Y$^-$ is an anion having a total charge of −1, or Y$^-$ is absence].
[Clause 7] The phosphonium compound according to [Clause 6], wherein
J is

[Chemical Formula 8]

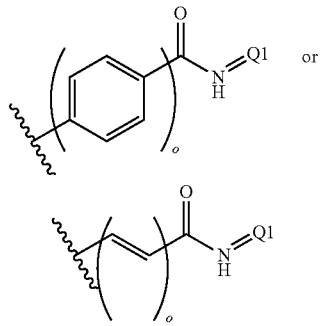

(wherein o is any integer of 0 to 6; and Q1 is a group formed by reaction of a hydrazide group with a carbonyl group contained in the compound to be derivatized);
J is

[Chemical Formula 9]

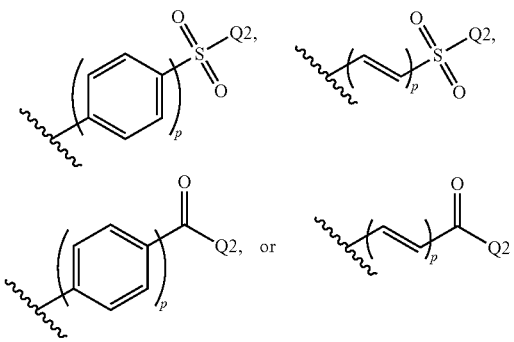

(wherein p is any integer of 0 to 6; and Q2 is a group formed by reaction of a halide group or a pseudohalide group with a phenol group or a hydroxy group contained in the compound to be derivatized); or
J is

[Chemical Formula 10]

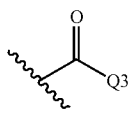

(wherein Q3 is a group formed by reaction of a thioester group with an amino group contained in the compound to be derivatized).
[Clause 8] A reagent for derivatization, the reagent comprising:
the phosphonium compound according to any of [Clause 1] to [Clause 5].
[Clause 9] A reagent kit for derivatization, the reagent kit comprising:
a phosphine compound below:

[Chemical Formula 11]

(wherein R$^1$, R$^2$, and R$^3$ are independently from each other, an alkyl group or an aryl group, the alkyl group is a substituted or unsubstituted, linear or branched alkyl group having 1 to 20 carbon atoms or a substituted or unsubstituted cyclic alkyl group having 5 to 20 carbon atoms, the aryl group is a substituted or unsubstituted aryl group having 6 to 20 carbon atoms); and
a reactive compound having a hydrazide group, a halide group, a pseudohalide group, or a thioester group.
[Clause 10] A mass spectrometric method comprising:
derivatizing a compound to be analyzed by mass spectrometry using the phosphonium compound according to any of [Clause 1] to [Clause 5], the reagent for derivatization according to [Clause 8], or the reagent kit for derivatization according to [Clause 9].

[Clause 11] A method for producing the phosphonium compound according to any of [Clause 1] to [Clause 5], X in the phosphonium compound being a reactive group having a hydrazide group, the method comprising:
  a first reaction step of reacting a phosphine compound below:

[Chemical Formula 12]

(wherein $R^1$, $R^2$, and $R^3$ are independently from each other, an alkyl group or an aryl group, the alkyl group is a substituted or unsubstituted, linear or branched alkyl group having 1 to 20 carbon atoms or a substituted or unsubstituted cyclic alkyl group having 5 to 20 carbon atoms, the aryl group is a substituted or unsubstituted aryl group having 6 to 20 carbon atoms), with a halogenated ethyl carboxylate below:

[Chemical Formula 13]

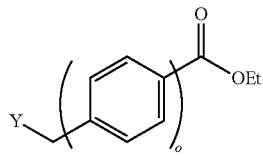

to form a compound below:

[Chemical Formula 14]

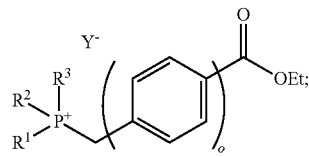

and
  a second reaction step of reacting the compound formed in the first reaction step with hydrazine to form the phosphonium compound.

[Clause 12] A method for producing the phosphonium compound according to any of [Clause 1] to [Clause 5], X in the phosphonium compound being a reactive group having a thioester group, the method comprising:
  reacting a phosphonium acetic acid below:

[Chemical Formula 15]

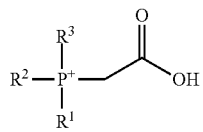

(wherein $R^1$, $R^2$, and $R^3$ are independently from each other, an alkyl group or an aryl group, the alkyl group is a substituted or unsubstituted, linear or branched alkyl group having 1 to 20 carbon atoms or a substituted or unsubstituted cyclic alkyl group having 5 to 20 carbon atoms, the aryl group is a substituted or unsubstituted aryl group having 6 to 20 carbon atoms) with a thiol below:

[Chemical Formula 16]

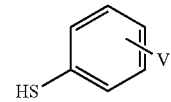

(wherein V is H, $NH_2$, $SO_3^-$ (a sulfonate ion group), $SO_3M$, $COO^-$, COOM, or a hydrophilic tag, and M is a hydrogen atom, a lithium atom, a sodium atom, or a potassium atom) to form the phosphonium compound.

The invention claimed is:

1. A phosphonium compound represented by Formula (I):

[Chemical Formula 1]

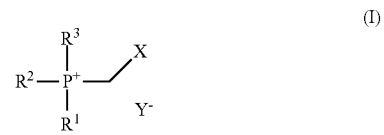

(I)

wherein in Formula (I), $R^1$ is an alkyl group, the alkyl group being a substituted or unsubstituted, linear or branched alkyl group having 1 to 20 carbon atoms or a substituted or unsubstituted cyclic alkyl group having 5 to 20 carbon atoms; and $R^2$ and $R^3$ are independently from each other, an alkyl group or an aryl group, the alkyl group is a substituted or unsubstituted, linear or branched alkyl group having 1 to 20 carbon atoms or a substituted or unsubstituted cyclic alkyl group having 5 to 20 carbon atoms, and the aryl group is a substituted or unsubstituted aryl group having 6 to 20 carbon atoms;

wherein X is a group having a hydrazide group, a halide group, a pseudohalide group, or a thioester group, and when X is the group having the hydrazide group, the group is

[Chemical Formula 3]

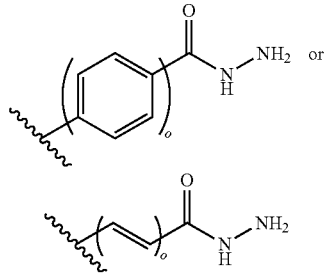

wherein o is any integer of 0 to 6;
when X is the group having the halide group or the pseudohalide group, the group is

[Chemical Formula 4]

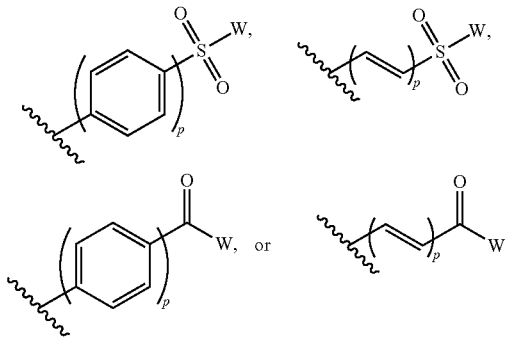

wherein W is a halogen or a pseudohalogen, and p is any integer of 0 to 6; or
when X is the group having the thioester group, the group is

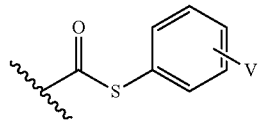

wherein V is H, $NH_2$, a sulfonate ion group $SO_3^-$, $SO_3M$, $COO^-$, or COOM, and M is a hydrogen atom, a lithium atom, a sodium atom, or a potassium atom; and
$Y^-$ is an anion having a total charge of −1, or $Y^-$ is absence.

2. The phosphonium compound according to claim 1, wherein in Formula (I),
the alkyl group is a substituted or unsubstituted, linear or branched alkyl group having 1 to 10 carbon atoms or a substituted or unsubstituted cyclic alkyl group having 5 to 10 carbon atoms, and
the aryl group is a substituted or unsubstituted aryl group having 6 to 10 carbon atoms.

3. The phosphonium compound according to claim 1, wherein in Formula (I),
$R^1$ is

[Chemical Formula 2a]

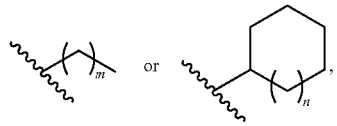

and $R^2$ and $R^3$ are independently from each other,

[Chemical Formula 2b]

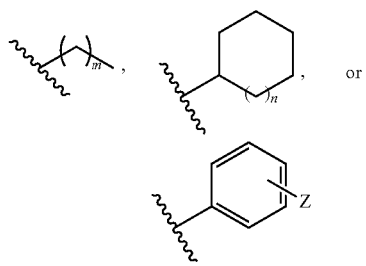

wherein m is any integer of 0 to 8; n is any integer of 0 to 5; Z is H, $NH_2$, $COO^-$, COOM, a sulfonate ion group $SO_3^-$, or a sulfonic acid group or a sulfonate salt group $SO_3M$; and M is a hydrogen atom, a lithium atom, a sodium atom, or a potassium atom.

4. A reagent for derivatization, the reagent comprising:
the phosphonium compound according to claim 1.

5. A mass spectrometric method comprising:
derivatizing a compound to be analyzed by mass spectrometry using the phosphonium compound according to claim 1.

* * * * *